US012721908B2

(12) United States Patent
Swaroop et al.

(10) Patent No.: US 12,721,908 B2
(45) Date of Patent: Sep. 1, 2026

(54) **GENE THERAPY FOR TREATMENT OF *CRX*-AUTOSOMAL DOMINANT RETINOPATHIES**

(71) Applicant: THE UNITED STATES OF AMERICA, as represented by the Secretary, Department of Health and Human Services, Bethesda, MD (US)

(72) Inventors: Anand Swaroop, Bethesda, MD (US); Zhijian Wu, Bethesda, MD (US); Suja D. Hiriyanna, Bethesda, MD (US); Kamil Kruczek, Bethesda, MD (US)

(73) Assignee: THE UNITED STATES OF AMERICA, as represented by the Secretary, Department of Health and Human Services, Bethesda, MD (US)

( * ) Notice: Subject to any disclaimer, the term of this patent is extended or adjusted under 35 U.S.C. 154(b) by 1034 days.

(21) Appl. No.: 17/789,729

(22) PCT Filed: Jan. 15, 2021

(86) PCT No.: PCT/US2021/013733
§ 371 (c)(1),
(2) Date: Jun. 28, 2022

(87) PCT Pub. No.: WO2021/146625
PCT Pub. Date: Jul. 22, 2021

(65) Prior Publication Data

US 2023/0066585 A1 Mar. 2, 2023

Related U.S. Application Data

(60) Provisional application No. 62/962,732, filed on Jan. 17, 2020.

(51) Int. Cl.

| | |
|---|---|
| ***C12N 15/85*** | (2006.01) |
| ***A61K 48/00*** | (2006.01) |
| ***A61P 27/02*** | (2006.01) |
| ***C07K 14/47*** | (2006.01) |
| ***C12N 15/86*** | (2006.01) |
| ***C12N 15/864*** | (2006.01) |

(52) U.S. Cl.
CPC ...... *A61K 48/0058* (2013.01); *A61K 48/0041* (2013.01); *A61P 27/02* (2018.01); *C07K 14/4705* (2013.01); *C12N 15/85* (2013.01); *C12N 15/86* (2013.01); *C12N 2750/14143* (2013.01); *C12N 2830/008* (2013.01)

(58) Field of Classification Search
CPC .... A61K 48/0058; C12N 15/79; C12N 15/85; C12N 15/86; C12N 15/864; C12N 15/8645; C12N 2750/14143; C12N 2830/008; A61P 27/02
See application file for complete search history.

(56) References Cited

U.S. PATENT DOCUMENTS

2004/0022766 A1* 2/2004 Acland .................. C12N 15/86 424/93.2
2012/0172419 A1* 7/2012 Neitz ...................... A61P 27/02 435/363
2015/0111955 A1* 4/2015 High ...................... C12N 15/86 435/456
2023/0103708 A1* 4/2023 Vetter ................ A61K 48/0075 424/93.21

FOREIGN PATENT DOCUMENTS

WO WO 2011/034947 A2 3/2011
WO WO 2018/172961 A1 9/2018
WO WO 2019/122425 A1 6/2019
WO WO 2020/182722 A1 9/2020

OTHER PUBLICATIONS

Kingdoms of Life, waynesword.palomar.edu/trfeb98.htm, last visited Apr. 8, 2021.*
Mammal, en.wikipedia.org/wiki/Mammal, last visited Aug. 31, 2022.*
www.calculator.net/exponent-calculator; last visited Aug. 11, 2025.*
Moreira et al., Hot spots—review of the protein-protein interface determinant amino-acid residues, Proteins 68: 803-812, 2007.*
Ng et al, Predicting the Effects of Amino Acid Substitutions on Protein Function, Annual Review Genomics Human Genetics 7: 61-80, 2006.*
Fumoto et al, Targeted Gene Delivery: Importance of Administration Routes, INTECH, Novel Gene Therapy Approaches, p. 3-31; editors Wei and Good, publisher Books on Demand, 2013.*
Daya et al, Gene Therapy Using Adeno-Associated Virus Vectors, Clin. Microbiol. Rev. 21(4): 583-593, 2008.*
Mingozzi and High, Immune responses to AAV vectors: overcoming barriers to successful gene therapy, Blood 122(1): 23-36, 2013.*

(Continued)

*Primary Examiner* — Kevin K Hill

(74) *Attorney, Agent, or Firm* — Klarquist Sparkman, LLP

(57) ABSTRACT

Methods are disclosed for treating a cone rod homeobox transcription factor (CRX) autosomal dominant retinopathy in a subject. These methods include administering to the subject an effective amount of a nucleic acid molecule comprising a retinal specific promoter operably linked to a nucleic acid molecule encoding a CRX protein. Compositions are disclosed that include an effective amount of a nucleic acid molecule comprising a retinal specific promoter operably linked to a nucleic acid molecule encoding CRX, for use in treating a CRX autosomal dominant retinopathy in a subject. A retinal specific promoter is disclosed that includes the nucleotide sequence of SEQ ID NO: 1.

11 Claims, 36 Drawing Sheets

Specification includes a Sequence Listing.

(56) References Cited

OTHER PUBLICATIONS

Kattenhorn et al, Adeno-Associated Virus Gene Therapy for Liver Disease, Human Gene Therapy 27(12): 947-961, Nov. 28, 2016.*
Wilson et al, Gene therapy for retinal ganglion cell neuroprotection in Glaucoma, Gene Therapy 19: 127-136, 2012.*
Watanabe et al, Tropisms of AAV for Subretinal Delivery to the Neonatal Mouse Retina and Its Application for In Vivo Rescue of Developmental Photoreceptor Disorders, PLoS ONE 8(1): e54146, doi.org/10.1371/journal.pone.0054146; available online Jan. 15, 2013.*
Roger et al, OTX2 loss causes rod differentiation defect in CRX-associated congenital blindness, J. Clin. Invest. 124(2): 631-643, 2014.*
Perrin, Make Mouse Studies Work, Nature (507): 423-425, 2014.*
Greenberg, Gene Therapy for heart failure, Trends in Cardiovascular Medicine 27: 216-222, 2017.*
Maguire et al, Viral vectors for gene delivery to the inner ear, Hearing Research 394: e107927, 13 pages, doi.org/10.1016/j.heares.2020.107927, 2020.*
Tobias, Mouse Study Used in Research, Multiple Sclerosis News Today, multiplesclerosisnewstoday.com/news-posts/2023/09/08/lets-not-get-overexcited-about-any-mice-study-used-research/; Sep. 8, 2023.*
Ferdowsian et al, Primates in Medical Research: A Matter of Convenience, not Sound Science, The Hastings Center, www.thehastingscenter.org/primates-in-medical-research-convenience-not-sound-science/; Jul. 8, 2022.*
Ibrahim et al, A complete, homozygous CRX deletion causing nullizygosity is a new genetic mechanism for Leber congenital amaurosis, Scientific Reports 8: e5034, DOI:10.1038/s41598-018-22704-z; available online Mar. 22, 2018.*
Sun et al, Generation of a transgenic mouse for inducible ectopic CRX expression, ARVO Annual Meeting Abstract, Invest. Ophtalmol. & Vis. Sci. 60: e2374, presented Apr. 28-May 2, 2019.*
Hodges et al, Characterization of the Genomic and Transcriptional Structure of the CRX Gene: Substantial Differences between Human and Mouse, Genomes 80(5): 531-542, 2002.*
GenBank AF335246.1, human CRX promoter region and exon1a, 2002.*
GenBank NG_008605.1, human CRX gene, 2018.*
Hodges et al., "Characterization of the Genomic and Transcriptional Structure of the CRX Gene: Substantial Differences between Human and Mouse," *Genomics* 80(5): 531-542, Nov. 2022.
Database EMBL accession No. AF024711, "*Homo sapiens* cone rod homeobox protein (CRX) gene, complete eds," (Dec. 9, 1997).
Database EMBL accession No. AF335246, "*Homo sapiens* cone rod homeobox protein (CRX) gene, promoter region and exon 1A," (Oct. 24, 2002).
Furukawa et al., "Retinopathy and attenuated circadian entrainment in Crx-deficient mice," *Nature Genetics* (4):466-470 (Dec. 1999).
International Search Report and Written Opinion from parent PCT Application No. PCT/US2021/013733, 21 pages (Jul. 2, 2021).
Kruczek et al., "Gene Therapy of Dominant CRX-Leber Congenital Amaurosis using Patient Stem Cell-Derived Retinal Organoids," *Stem Cell Report* 16(2): 252-263 (e-Pub Jan. 28, 2021).
Nichols et al., "Two novel CRX mutant proteins causing autosomal dominant Leber congenital amaurosis interact differently with NRL," *Human Mutation* 31(6): E1472-E1483 (Jun. 2010).
Occelli et al., "CrxRdy cat: A large animal model for CRX-associated Leber congenital amaurosis," *IOVS* 57(8): 3780-3791 (Jul. 2016).
Roger et al., "OTX2 loss causes rod differentiation defect in CRX-associated congenital blindness," *Journal of Clinical Investigation* 124(2): 631-643 (e-Pub Jan. 2, 2014).
Tran and Chen "Mechanisms of blindness: animal models provide insight into distinct CRX-associated retinopathies," *Developmental Dynamics* 243(10): 1153-1166 (e-Pub Jun. 27, 2014).
Tran et al., "Mechanistically distinct mouse models for CRX-associated retinopathy," *PLoS Genetics* 10(2): e1004111 (Feb. 2014).
Watanabe et al., "Tropisms of AAV for subretinal delivery to the neonatal mouse retina and its application for in vivo rescue of developmental photoreceptor disorders," *PLoS One* 8(1): e54146 (e-Pub Jan. 15, 2013).

* cited by examiner 299 amino acids
39 - 108 amino acids
113 - 284 amino acids
Healthy
N
Homeodomain DNA-binding
Transactivation domain
C
CRX-LCA
N
Homeodomain DNA-binding
C
I138fs48 (c.413delT mutation)

Floating EBs
Adherent culture
Retinal organoids in suspension culture
Plating on Matrigel
Dissection of optic vesicles
9cisRA 1 uM
9cisRA 500 nM
1:1 NIM
1:1 NIM
3:1 NIM
3:1 NIM + 10% FBS + IGF-1 + Tau
d0
d7
d16
D28-42
d90

S opsin

S opsin
p=0.003
S OPSIN+/mm2
60
40
20
0
Control
CRX-LCA
p<0.0001
Florescence intensity (AU)
20
15
10
5
0
Control
CRX-LCA
Control
CRX-LCA
CRX-LCA
median = 26
Control
median = 50
Number of values
15
10
5
0
15 20 25 30 35 40 45 50 55 60 65 70 75 80 85
Fluorescence intensity (binned)

Rhodopsin

CMV promoter
$1x10^{11}$ vg/organoid

Control

CRX promoter
$5x10^{10}$ vg/organoid

Control

CRX promoter
$1x10^{11}$ vg/organoid

Control

CRX promoter 1x10$^{11}$ vg/organoid

Control

+AAV-CRX
$10^{11}$ vg per organoid
Start of differentiation
d0
d120
d180
Analysis
B
Untreated
C
AAV2/2-CRX 1e11
D
AAV2/2-CRX 3e11
Rhodopsin DAPI FIG. 7A
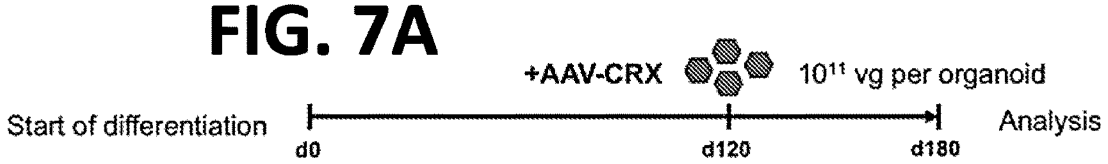
FIG. 7B FIG. 7C FIG. 7D
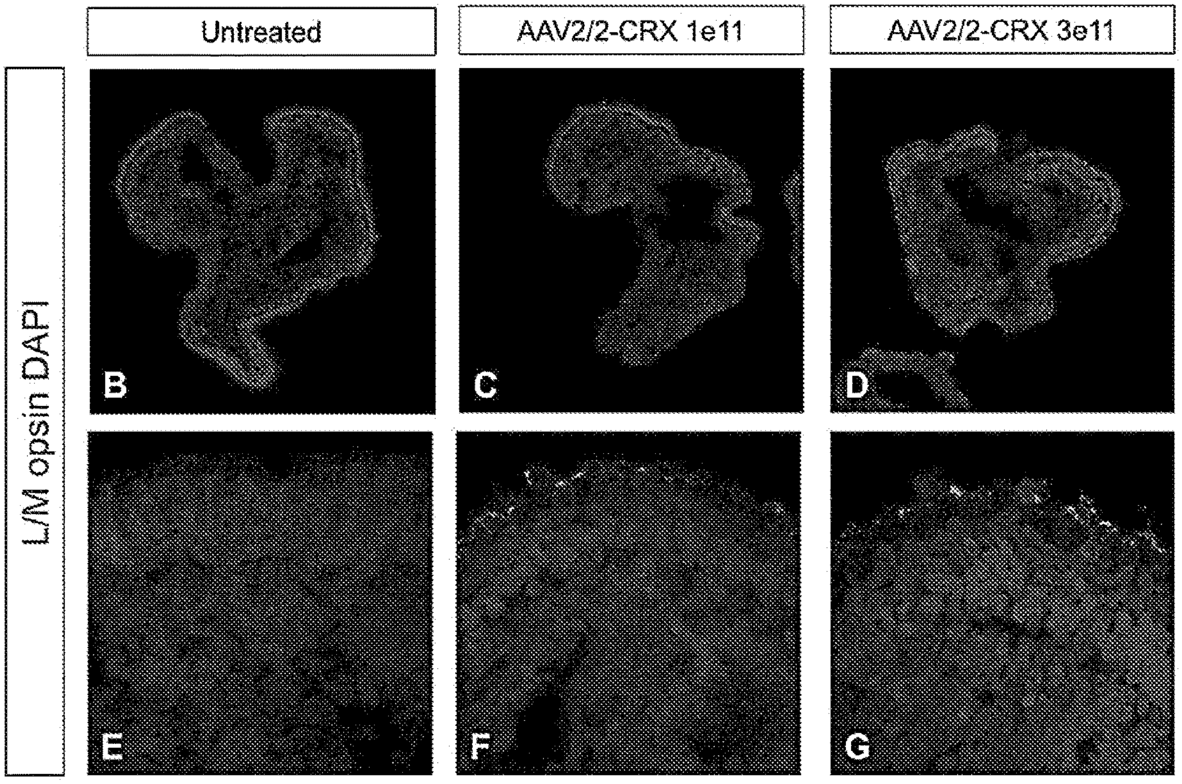
FIG. 7E FIG. 7F FIG. 7G CABP4
Rods
Expression Level
1.5
1.0
0.5
0.0
control
untreated
AAV-treated
Identity
CABP4
Cones
Expression Level
1.0
0.5
0.0
control
untreated
AAV-treated
Identity FIG. 12E
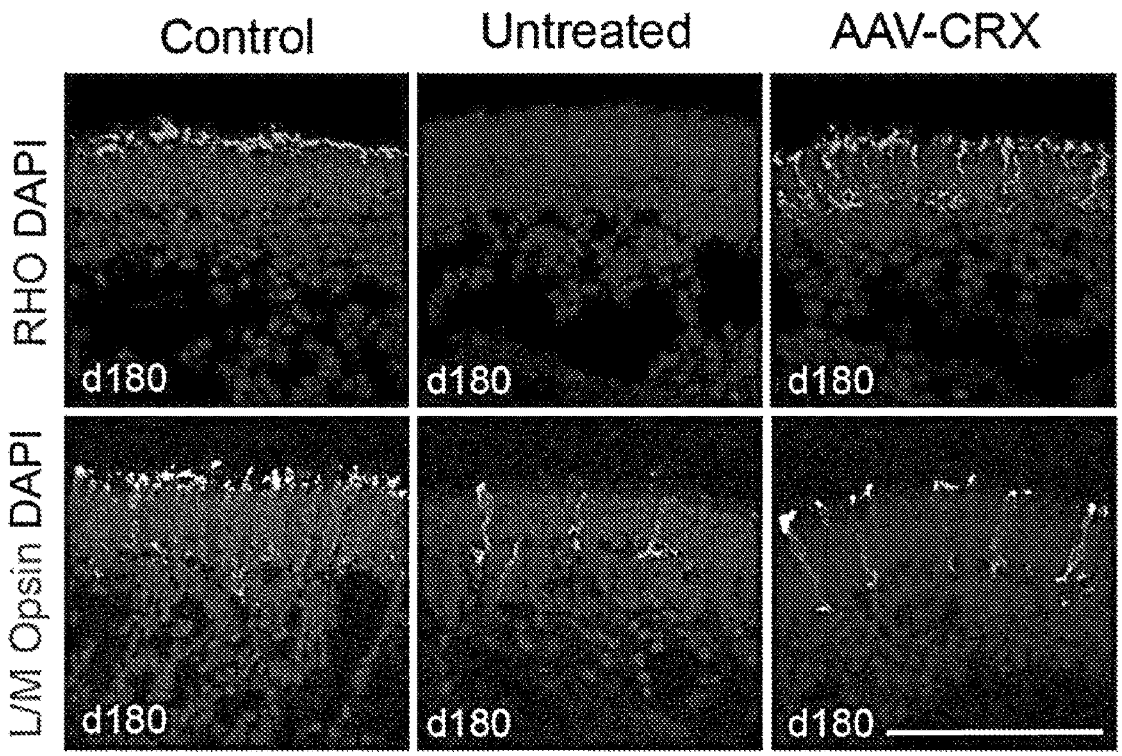
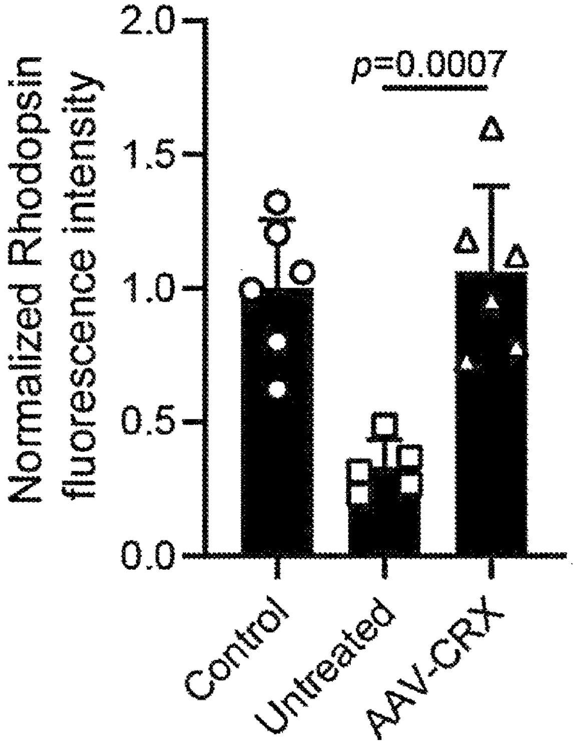
FIG. 12F
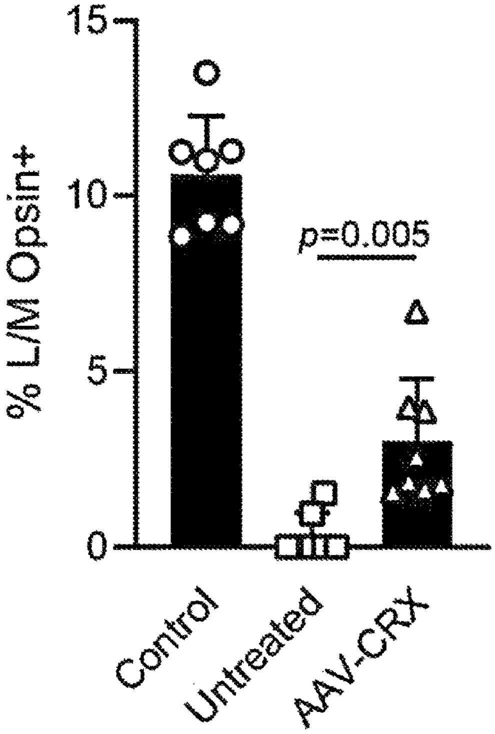
FIG. 12G

SEQUENCE LISTING

```
<160> NUMBER OF SEQ ID NOS: 2

<210> SEQ ID NO 1
<211> LENGTH: 631
<212> TYPE: DNA
<213> ORGANISM: Homo sapiens

<400> SEQUENCE: 1

cgtcgacggg tcagacggcc cctccctctc ttgctgtcat ccctggctct tcaagctaat      60

gagacctgtc ctgattcctc agccaggcct gtagccttaa tctctcctag caggggggttt    120

gggggaggga ggaggagaaa gaaagggccc cttatggctg agacacaatg acccagccac    180

aaggagggat taccggggaa gtgaaacaga cccgtgtggg acccaggagc tcagggacat    240

attaatatct agagagacag acggtcgaca gacaccagtt agacctaagg aaggacttcc    300

ctgaggagta ggggcttatg gtcaccggca ggagctgggg cctcccttcc ccatcagccc    360

taattgccaa gatgtcatgg ggggaagagg aggggattaa gcagacgggt gcccctcccc    420

ctcccagcca atgtcacctc ctggtgccca gtcgagtccc ccaccttggc cgggattacc    480

ctccgagttc caggccataa caagtgacat cactcccggc ccaggcttaa aatctcccca    540

cgtgagggga cgtgtttcct tcagcctctg ctgtctggcc gctctgtcta ggtcctgggc    600

cacgggagag ccccgtccct cctttctgaa g                                   631


<210> SEQ ID NO 2
<211> LENGTH: 299
<212> TYPE: PRT
<213> ORGANISM: Homo sapiens

<400> SEQUENCE: 2

Met Met Ala Tyr Met Asn Pro Gly Pro His Tyr Ser Val Asn Ala Leu
1               5                   10                  15

Ala Leu Ser Gly Pro Ser Val Asp Leu Met His Gln Ala Val Pro Tyr
            20                  25                  30

Pro Ser Ala Pro Arg Lys Gln Arg Arg Glu Arg Thr Thr Phe Thr Arg
        35                  40                  45

Ser Gln Leu Glu Glu Leu Glu Ala Leu Phe Ala Lys Thr Gln Tyr Pro
    50                  55                  60

Asp Val Tyr Ala Arg Glu Glu Val Ala Leu Lys Ile Asn Leu Pro Glu
65                  70                  75                  80

Ser Arg Val Gln Val Trp Phe Lys Asn Arg Arg Ala Lys Cys Arg Gln
                85                  90                  95

Gln Arg Gln Gln Gln Lys Gln Gln Gln Gln Pro Pro Gly Gly Gln Ala
            100                 105                 110

Lys Ala Arg Pro Ala Lys Arg Lys Ala Gly Thr Ser Pro Arg Pro Ser
        115                 120                 125
```

-continued

```
Thr Asp Val Cys Pro Asp Pro Leu Gly Ile Ser Asp Ser Tyr Ser Pro
    130                 135                 140

Pro Leu Pro Gly Pro Ser Gly Ser Pro Thr Thr Ala Val Ala Thr Val
145                 150                 155                 160

Ser Ile Trp Ser Pro Ala Ser Glu Ser Pro Leu Pro Glu Ala Gln Arg
                165                 170                 175

Ala Gly Leu Val Ala Ser Gly Pro Ser Leu Thr Ser Ala Pro Tyr Ala
            180                 185                 190

Met Thr Tyr Ala Pro Ala Ser Ala Phe Cys Ser Ser Pro Ser Ala Tyr
        195                 200                 205

Gly Ser Pro Ser Ser Tyr Phe Ser Gly Leu Asp Pro Tyr Leu Ser Pro
    210                 215                 220

Met Val Pro Gln Leu Gly Gly Pro Ala Leu Ser Pro Leu Ser Gly Pro
225                 230                 235                 240

Ser Val Gly Pro Ser Leu Ala Gln Ser Pro Thr Ser Leu Ser Gly Gln
                245                 250                 255

Ser Tyr Gly Ala Tyr Ser Pro Val Asp Ser Leu Glu Phe Lys Asp Pro
            260                 265                 270

Thr Gly Thr Trp Lys Phe Thr Tyr Asn Pro Met Asp Pro Leu Asp Tyr
        275                 280                 285

Lys Asp Gln Ser Ala Trp Lys Phe Gln Ile Leu
    290                 295
```

GENE THERAPY FOR TREATMENT OF *CRX*-AUTOSOMAL DOMINANT RETINOPATHIES

CROSS REFERENCE TO RELATED APPLICATION

This is a § 371 U.S. national stage of International Application No. PCT/US2021/013733, filed Jan. 15, 2021, which claims the benefit of U.S. Provisional Application No. 62/962,732, filed Jan. 17, 2020. The prior applications are incorporated by reference herein.

STATEMENT OF GOVERNMENT SUPPORT

This invention was made with Government support under project number: ZIAEY000474, ZIAEY000450, and ZIAEY000546 by the National Institutes of Health, National Eye Institute Intramural Research Program. The United States Government has certain rights in the invention.

FIELD OF THE DISCLOSURE

This relates to the field of cone rod homeobox transcription factor (CRX) autosomal dominant retinopathies, specifically to the use of a nucleic acid molecule comprising a retinal specific promoter operably linked to a nucleic acid molecule encoding a CRX protein for treatment of these retinopathies.

BACKGROUND

Inherited retinal diseases (IRDs) are a major cause of registered and largely incurable blindness worldwide. Mutations in as many as 300 genes can cause IRDs, with approximately 70 genes identified as causative for the most common condition retinitis pigmentosa (RP) (information available on the internet, see for example, sph.uth.edu/retnet/). IRDs are currently the most diverse of the described hereditary conditions in humans. Leber congenital amaurosis (LCA) constitutes a group of early onset blinding diseases (in young children) with at least 25 causal genes that overlap with RP genes. Typically, IRDs are characterized by gradual loss of light sensing photoreceptor cells in the retina at the back of the eye leading to reduced light detection capacity and eventually blindness. The most common modes of inheritance are autosomal recessive, autosomal dominant and X-linked, but digenic and mitochondrial etiology have also been observed. Frequently, patients with not only different mutations in the same gene but also with the exact same mutation demonstrate divergent clinical phenotypes, presenting a challenge to patient counseling and disease management. Many pathological mutations are found in genes that affect photoreceptor-specific functions within the retina (den Hollander et al., *Prog Retin Eye Res,* 27, 391-419; Wright et al., *Nat Rev Genet,* 11, 273-284). A need remains for gene therapy methods that can be used to teat autosomal dominant retinopathies.

SUMMARY OF THE DISCLOSURE

Methods are disclosed for treating a CRX autosomal dominant retinopathy in a subject. These methods include administering to the subject an effective amount of a nucleic acid molecule comprising a retinal specific promoter operably linked to a nucleic acid molecule encoding a CRX protein, thereby treating the CRX autosomal dominant retinopathy in the subject.

In additional embodiments, compositions are disclosed that include an effective amount of a nucleic acid molecule comprising a retinal specific promoter operably linked to a nucleic acid molecule encoding CRX protein, for use in treating a CRX autosomal dominant retinopathy in a subject.

In further embodiments, A promoter is disclosed that includes the nucleotide sequence of SEQ ID NO: 1. This promoter can be used in the disclosed methods.

The foregoing and other features and advantages of the invention will become more apparent from the following detailed description of several embodiments which proceeds with reference to the accompanying figures.

BRIEF DESCRIPTION OF THE FIGURES

FIGS. 7A-7G. Restoration of L/M Opsin expression following AAV-CRX treatment of c.413delT (p.I138fs48) patient retinal organoids. (A) Timeline of treatment. (B-G) Immunostaining for L/M Opsin in untreated (B,E), low AAV dose ($1\times10^{11}$; C,F) and high dose ($3\times10^{11}$; D,G). Nuclei were visualized by counterstaining with DAPI. (H) Quantification of L/M Opsin fluorescence intensity in relation to familial control sample. At least three organoids per group, Student's t-test, p values indicated.

FIGS. 12A-12G. Disease phenotype and gene augmentation therapy of CRX-K88N patient retinal organoids. (A) Brightfield images of control and CRX-K88N patient organoids showing reduced outer segment (OS) apical 'brush' layer (arrowheads). (B) Quantification of the outer segment-like layer thickness; n=6 organoids per group, 3 sections each; mean±SD, p values from one-way ANOVA. (C) Immunostaining of organoids at d200 for CRX, Recoverin and Opsin proteins Rhodopsin and L/M Opsins. Note diminished Rhodopsin and L/M Opsin staining in patient-derived organoids. (D) Heatmap comparing expression of genes (bulk RNA-seq) of d120 and d200 organoids. Expression of many photoreceptor-specific transcripts is either delayed or reduced in CRX-K88N patient samples. Normalized log 2 (CPM+1) values plotted. TFs—transcription factors, OS—outer segment. (E) AAV treatment assessment by immunostaining. Immunoreactivity for both Rhodopsin and L/M Opsin is partially restored following AAV treatment. All scale bars 100 μm. (F) Quantification of Rhodopsin fluorescence intensity in AAV-treated retinal organoids. Control n=6, untreated n=5 and AAV-treated n=6 organoids; 3 sections each; mean±SD, p values from one-way ANOVA. (G) Quantification of the percentage of L/M Opsin+ cones in AAV-treated retinal organoids. Control n=7, untreated n=7 and AAV-treated n=8 organoids; 3 sections each; mean±SD, p values from one-way ANOVA.

SEQUENCE LISTING

Figure 1A:
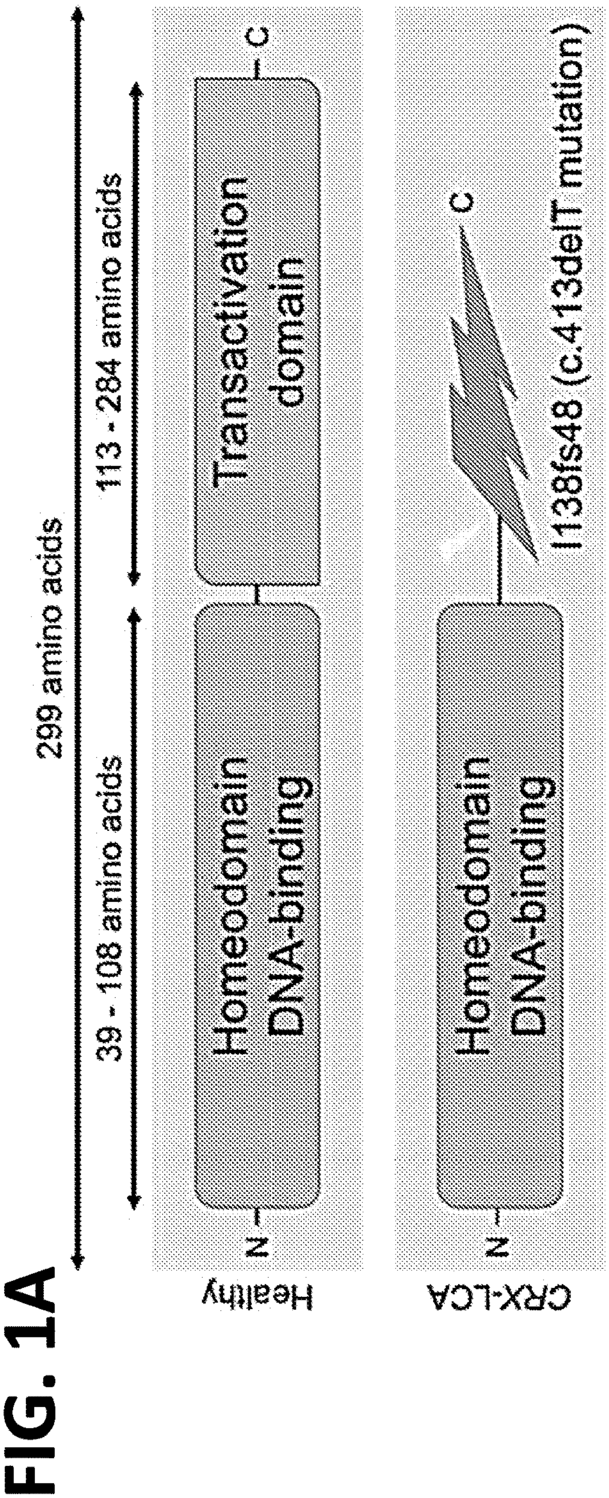
FIGS. 1A-1L. Impaired photoreceptor maturation in CRX-LCA retinal organoids with c.413delT (p.I138fs48) mutation. (A-B) Schematic representations of CRX domain structure and the effect of pathological mutation (A) and the retinal organoid differentiation protocol (B). (C) Immunostaining for Recoverin, S Opsin and Rhodopsin at day 125. Scale bar 50 μm. (D) Quantification of the number of S Opsin+ cells per organoid area. (E) Quantification of average S Opsin fluorescence intensity in individual cells. (F) Histogram of maximal fluorescence intensity values for samples in (E). (G) Quantification of Rhodopsin fluorescence intensity values. (H) Percentage of organoids showing discernible Rhodopsin immunostaining. Organoids in (D-H) all at day 125. (I) Wholemount immunostaining of Rhodopsin and L/M Opsin in control or CRX-I138fs patient organoids at day 230. Nuclei are counterstained with DAPI. Scale bar 200 μm. (J) Immunostaining for Peripherin2 and CTBP2 (Ribeye) at d200. Scale bar 20 μm. (K-L) Quantification of Peripherin2 puncta (K) and CTBP2 fluorescence intensity (L, n=3). Statistical significance determined by Student's t test.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file [Sequence_Listing, Jun. 22, 2022, 3.95 KB], which is incorporated by reference herein. In the accompanying sequence listing:

SEQ ID NO: 1 is the nucleic acid sequence of a recombinant human CRX promoter.

SEQ ID NO: 2 is an amino acid sequence of a human CRX protein.

DETAILED DESCRIPTION OF SEVERAL EMBODIMENTS

The CRX gene encodes a transcription regulatory protein that is essential for the development and function of retinal photoreceptors. Mutations in CRX cause dysfunction of photoreceptors resulting in distinct retinal disease phenotypes. Specific dominant mutations in CRX can lead to congenital blindness, whereas recessive mutations result in later onset photoreceptor dysfunction. A nucleic acid molecule including a recombinant CRX promoter operably linked to a nucleic acid sequence encoding a full-length human CRX protein was used to correct an autosomal dominant CRX retinopathy. The therapeutic potential of this construct was tested using human retinal organoid tissue differentiated from induced pluripotent stem cells derived from patients with two different dominant CRX mutations. The nucleic acid molecule was capable of transducing human stem cell-derived retinal tissues in vitro, and the administration restored patient photoreceptors including partial rescue of Rhodopsin and M/L Opsin expression, two proteins required for detection of light in human retina, in patients with autosomal dominant CRX retinopathy.

Cells from patient biopsy samples were reprogrammed into induced pluripotent stem cells (iPSCs). The iPSCs obtained from patients with a CRX mutation as well as familial healthy controls were differentiated into retinal organoids. These organoids represent a system showing key characteristics of native human retina such as expression of molecular markers and cell type composition and tissue architecture. Patients with different autosomal dominant CRX mutations presented a range of clinical phenotypes with varying severity, which could be treated using the presently disclosed methods.

Terms

The following explanations of terms and methods are provided to better describe the present disclosure and to guide those of ordinary skill in the art in the practice of the present disclosure. The singular forms “a,” “an,” and “the” refer to one or more than one, unless the context clearly dictates otherwise. For example, the term “comprising a cell” includes single or plural cells and is considered equivalent to the phrase “comprising at least one cell.” The term “or” refers to a single element of stated alternative elements or a combination of two or more elements, unless the context clearly indicates otherwise. Thus, “comprising A or B,” means “including A, B, or A and B,” without excluding additional elements. As used herein, “comprises” means “includes.” Unless otherwise indicated, “about” means within five percent. Dates of GENBANK® Accession Nos. referred to herein are the sequences available at least as early as Dec. 31, 2019. All references, patent applications and publications, and GENBANK® Accession numbers cited herein are incorporated by reference. In order to facilitate review of the various embodiments of the disclosure, the following explanations of specific terms are provided:

Adeno-associated Virus (AAV): AAV is a small virus that infects humans and some other primate species. AAV is not currently known to cause disease and consequently the virus causes a very mild immune response. AAV can infect both dividing and non-dividing cells and mainly exists as episomal forms in the host cell. The AAV genome is built of single-stranded deoxyribonucleic acid (ssDNA), either positive- or negative-sensed, which is about 4.7 kilobases (kb) long. The genome comprises inverted terminal repeats (ITRs) at both ends of the DNA strand, and two open reading frames (ORFs): rep and cap. Rep is composed of four overlapping genes encoding Rep proteins required for the AAV life cycle, and Cap contains overlapping nucleotide sequences of capsid proteins: VP1, VP2 and VP3, which interact together to form a capsid of an icosahedral symmetry. For gene therapy, ITRs seem to be the only sequences required in cis next to the therapeutic gene: structural (cap) and packaging (rep) genes can be delivered in trans.

Autosomal Dominant: A pattern of inheritance in which an individual affected with a disease has one copy of a mutant gene and one normal gene on a pair of autosomal chromosomes. In contrast, autosomal recessive diseases require that the individual have two copies of the mutant gene for the individual to be affected by the disease.

Cell Culture: Cells grown under controlled condition. A primary cell culture is a culture of cells, tissues or organs taken directly from an organism and before the first subculture. Cells are expanded in culture when they are placed in a growth medium under conditions that facilitate cell growth and/or division, resulting in a larger population of the cells. An “organoid” is an organ that is produced in vitro, such as from iPSCs.

Cone-Rod Dystrophy: The first signs and symptoms of cone-rod dystrophy, which often occur in childhood, are usually decreased sharpness of vision (visual acuity) and increased sensitivity to light (photophobia). These features are typically followed by impaired color vision (dyschromatopsia), blind spots (scotomas) in the center of the visual field, and partial side (peripheral) vision loss. Over time, affected individuals develop night blindness and a worsening of their peripheral vision, which can limit independent mobility. The cone dystrophy is characterized by progressive dysfunction of the photopic system, with preservation of scotopic function. Abnormal rod function may be part of the initial presentation, but rod involvement may be less severe, or occur later than the cone dysfunction. There are more than 30 types of cone-rod dystrophy, which are distinguished by their genetic cause and their pattern of inheritance: autosomal recessive, autosomal dominant, and X-linked. Mutations in more than 30 genes are known to cause cone-rod dystrophy. Approximately 20 of these genes are associated with the form of cone-rod dystrophy that is inherited in an autosomal recessive pattern. Mutations in the GUCY2D and CRX genes account for about half of the autosomal dominant form of this disease.

Cone rod homeobox transcription factor (CRX) Retinopathy: A retinopathy that results from a mutation in the CRX gene. These mutations have been identified in dystrophies ranging from severe early-onset Leber congenital amaurosis (LCA, LCA7, MIM #613829) through adult-onset cone-rod dystrophy (CORD2, MIM #120970), retinitis pigmentosa (RP, MIM #268000) to mild late-onset macular dystrophy. Approximately 50 likely pathological mutations that cause CRX retinopathy have been described, half of these co-segregate with the disease phenotype. Reported mutations are 39% missense, 4% nonsense, 37% deletion, 16% insertion and 4% indel (insertion and deletion) sequence changes. A CRX retinopathy can be autosomal dominant, autosomal recessive, or X-linked. Three main inherited retinal dystrophies associated with mutations in CRX are Leber congenital amaurosis (LCA), retinitis pigmentosa (RP) and cone-rod dystrophy (CORD). A common feature in CRX retinopathies is macular atrophy.

Dendrimer: Synthetic three-dimensional macromolecules that are prepared in a step-wise fashion from simple branched monomer units, the nature and functionality of which can be easily controlled and varied. Dendrimers are synthesized from the repeated addition of building blocks to a multifunctional core (divergent approach to synthesis), or towards a multifunctional core (convergent approach to synthesis) and each addition of a three-dimensional shell of building blocks leads to the formation of a higher generation of the dendrimers. Dendrimers can be used for deliver of nucleic acid molecules.

Downstream: A relative position on a polynucleotide, wherein the "downstream" position is closer to the 3' end of the polynucleotide than the reference point. In the instance of a double-stranded polynucleotide, the orientation of 5' and 3' ends are based on the sense strand, as opposed to the antisense strand.

Effective Amount: A quantity of a specified pharmaceutical or therapeutic agent sufficient to achieve a desired effect in a subject, or in a cell, being treated with the agent. The effective amount of the agent, such as a nucleic acid molecule, will be dependent on several factors, including, but not limited to the subject or cells being treated, and the manner of administration of the therapeutic composition. An effective amount can be the amount sufficient to treat a subject with a retinopathy.

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

Heterologous: A heterologous sequence is a sequence that is not normally (in the wild-type sequence) found adjacent to a second sequence. In one embodiment, the sequence is from a different genetic source, such as a virus or organism, than the second sequence. In another embodiment, the heterologous sequence is a recombinant sequence that is not normally next to the wild-type sequence.

Inhibiting or treating a disease: Inhibiting the full development of a disease or condition, for example, in a subject who is at risk for a disease such as a autosomal dominant retinopathy, such as, but not limited to, an autosomal dominant CRX retinopathy, such as, but not limited to, LCA. "Treatment" refers to a therapeutic intervention that ameliorates a sign or symptom of a disease or pathological condition after it has begun to develop. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease, such as improved vision. Treatment may be assessed by objective or subjective parameters; including, but not limited to, the results of a physical examination, neurological examination, or vision test. A "prophylactic" treatment is a treatment administered to a subject who does not exhibit signs of a disease or exhibits only early signs for the purpose of decreasing the risk of developing pathology.

Intraocular administration: Administering agents locally, directly into the eye, for example by delivery into the vitreous or anterior chamber, or sub-retinally. Indirect intraocular delivery (for example by diffusion through the cornea) is not direct administration into the eye.

Intravitreal administration: Administering agents into the vitreous cavity. The vitreous cavity is the space that occupies most of the volume of the core of the eye with the lens and its suspension system (the zonules) as its anterior border and the retina and its coating as the peripheral border. Intravitreal administration can be accomplished by injection, pumping, or by implants.

Isolated: An "isolated" biological component has been substantially separated, produced apart from, or purified away from other biological components in the cell of the organism in which the component naturally occurs, such as, other chromosomal and extrachromosomal DNA and RNA, and proteins. Nucleic acids, peptides and proteins that have been "isolated" thus include nucleic acids and proteins purified by standard purification methods. The term also embraces nucleic acids, peptides, and proteins prepared by recombinant expression in a host cell as well as chemically synthesized nucleic acids.

Leber congenital amaurosis (LCA): A rare inherited eye disease that appears at birth or in the early stages of life (infancy or early childhood) and primarily affects the retina. The presentation can vary because is it associated with multiple genes. However, it is characterized by characterized by nystagmus, photophobia, sluggish or absent pupillary response, and severe vision loss or blindness. The common modes of inheritance are autosomal recessive and autosomal dominant.

The pupils, which usually expand and contract in response to the amount of light entering the eye, do not react normally to light. Instead, they expand and contract more slowly than normal, or they may not respond to light at all. Additionally, the clear front covering of the eye (the cornea) may be cone-shaped and abnormally thin, a condition known as keratoconus.

A specific behavior called Franceschetti's oculo-digital sign is characteristic of Leber congenital amaurosis. This sign consists of poking, pressing, and rubbing the eyes with a knuckle or finger.

Nanoparticle: A particle between 1 and 100 nanometers (nm) in size with a surrounding interfacial layer. The interfacial layer is an integral part of nanoscale matter, fundamentally affecting all of its properties. The interfacial layer typically consists of ions, inorganic and/or organic molecules.

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Recombinant nucleic acid" refers to a nucleic acid having nucleotide sequences that are not naturally joined together. This includes nucleic acid vectors comprising an amplified or assembled nucleic acid which can be used to transform a suitable host cell. A host cell that comprises the recombinant nucleic acid is referred to as a "recombinant host cell." The gene is then expressed in the recombinant host cell to produce, such as a "recombinant polypeptide." A recombinant nucleic acid may serve a non-coding function (such as a promoter, origin of replication, ribosome-binding site, etc.) as well.

A first sequence is an "antisense" with respect to a second sequence if a polynucleotide whose sequence is the first sequence specifically hybridizes with a polynucleotide whose sequence is the second sequence.

Terms used to describe sequence relationships between two or more nucleotide sequences or amino acid sequences include "reference sequence," "selected from," "comparison window," "identical," "percentage of sequence identity," "substantially identical," "complementary," and "substantially complementary."

For sequence comparison of nucleic acid sequences, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are used. Methods of alignment of sequences for comparison are well known in the art. Optimal alignment of sequences for comparison can be conducted, for example, by the local homology algorithm of Smith & Waterman, *Adv. Appl. Math.* 2:482, 1981, by the homology alignment algorithm of Needleman & Wunsch, *J. Mol. Biol.* 48:443, 1970, by the search for similarity method of Pearson & Lipman, *Proc. Nat'l. Acad. Sci. USA* 85:2444, 1988, by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see for example, *Current Protocols in Molecular Biology* (Ausubel et al., eds 1995 supplement)).

One example of a useful algorithm is PILEUP. PILEUP uses a simplification of the progressive alignment method of Feng & Doolittle, *J. Mol. Evol.* 35:351-360, 1987. The method used is similar to the method described by Higgins & Sharp, *CABIOS* 5:151-153, 1989. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, such as version 7.0 (Devereaux et al., *Nuc. Acids Res.* 12:387-395, 1984.

Another example of algorithms that are suitable for determining percent sequence identity and sequence similarity are the BLAST and the BLAST 2.0 algorithm, which are described in Altschul et al., *J. Mol. Biol.* 215:403-410, 1990 and Altschul et al., *Nucleic Acids Res.* 25:3389-3402, 1977. Software for performing BLAST analyses is publicly available through the National Center for Biotechnology Information on the ncbi.nlm.nih.gov webiste. The BLASTN program (for nucleotide sequences) uses as defaults a word length (W) of 11, alignments (B) of 50, expectation (E) of 10, M=5, N=−4, and a comparison of both strands. The BLASTP program (for amino acid sequences) uses as defaults a word length (W) of 3, and expectation (E) of 10, and the BLOSUM62 scoring matrix (see Henikoff & Henikoff, *Proc. Natl. Acad. Sci. USA* 89:10915, 1989).

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Pharmaceutically acceptable carriers: The pharmaceutically acceptable carriers useful in this invention are conventional. *Remington's Pharmaceutical Sciences*, by E. W. Martin, Mack Publishing Co., Easton, PA, 15th Edition (1975), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutical agent: A chemical compound or composition, such as including a nucleic acid molecule, capable of inducing a desired therapeutic or prophylactic effect when properly administered to a subject or a cell. "Incubating" includes a sufficient amount of time for a drug to interact with a cell. "Contacting" includes incubating a drug in solid or in liquid form with a cell.

Protein: Three or more covalently attached amino acids. The term encompasses polypeptides, protein fragments, and protein domains. A "DNA-binding" polypeptide is a polypeptide with the ability to specifically bind DNA.

The terms "protein" and "polypeptide" are specifically intended to cover naturally occurring proteins, as well as those which are recombinantly or synthetically produced. The terms "functional fragments of a protein" and "functional fragments of a polypeptide" refers to all fragments of a polypeptide that retain an activity of the polypeptide. Biologically functional fragments, for example, can vary in size from a polypeptide fragment as small as an epitope capable of binding an antibody molecule to a large polypeptide capable of participating in the characteristic induction or programming of phenotypic changes within a cell. An "epitope" is a region of a polypeptide capable of binding an immunoglobulin generated in response to contact with an antigen. Thus, smaller peptides containing the biological activity of insulin, or conservative variants of the insulin, are thus included as being of use.

Conservative substitutions replace one amino acid with another amino acid that is similar in size, hydrophobicity, etc. Examples of conservative substitutions are shown below.

| Original Residue | Conservative Substitutions |
|---|---|
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Variations in the cDNA sequence that result in amino acid changes, whether conservative or not, should be minimized in order to preserve the functional and immunologic identity of the encoded protein. The immunologic identity of the protein may be assessed by determining whether it is recognized by an antibody; a variant that is recognized by such an antibody is immunologically conserved. Any cDNA sequence variant will preferably introduce no more than twenty, and preferably fewer than ten amino acid substitutions into the encoded polypeptide. Variant amino acid sequences may, for example, be 80%, 90% or even 95% or 98% identical to the native amino acid sequence.

Promoter: A promoter is an array of nucleic acid control sequences which direct transcription of a nucleic acid. A promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription.

A promoter can be a constitutively active promoter (i.e., a promoter that is constitutively in an active/"ON" state), an inducible promoter (i.e., a promoter whose state, active/"ON" or inactive/"OFF", is controlled by an external stimulus, e.g., the presence of a particular temperature, compound, or protein.), a spatially restricted promoter (e.g., tissue specific promoter, cell type specific promoter, etc.), or it may be a temporally restricted promoter (i.e., the promoter is in the "ON" state or "OFF" state during specific stages of embryonic development or during specific stages of a biological process). A "retinal specific" promoter directs transcription of an operably linked nucleic acid in cells the retina, as compared to cells in different tissues. Inducible promoters can be regulated by molecules including, but not limited to, doxycycline; RNA polymerase, e.g., T7 RNA polymerase; an estrogen receptor; an estrogen receptor fusion; etc.

Purified: The term "purified" does not require absolute purity; rather, it is intended as a relative term. Thus, for example, a purified protein preparation is one in which the protein referred to is purer than the protein in its natural environment within a cell. For example, a preparation of a protein is purified such that the protein represents at least 50% of the total protein content of the preparation. Similarly, a purified nucleic acid molecule preparation is one in which the nucleic acid molecule is purer than in an environment including a complex mixture. A purified population of nucleic acids or proteins is greater than about 90%, 91%, 92%, 93%, 94%, 95%, 96%, 97%, 98%, 99% or 100% pure, or free other nucleic acids or proteins, respectively.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques. Similarly, a recombinant protein is one coded for by a recombinant nucleic acid molecule.

Retina: The light (photon) sensitive portion of the eye, that contains the photoreceptors (cones and rods) for light. Rods and cones perform light perception through the use of light sensitive pigments. The light sensitive pigments are made of protein called Opsin and a chromophore called retinene, which the variant is of vitamin A. The rods contain Rhodopsin while the cones contain iodopsin. Rods and cones transmit signals through successive neurons that trigger a neural discharge in the output cells of the retina and the ganglion cells. The visual signals are conveyed by the optic nerve to the lateral *geniculate* bodies from where the visual signal is passed to the visual cortex (occipital lobe) and registered as a visual stimulus. “Rod cells”, or “rods,” are photoreceptor cells in the retina of the eye that can function in less intense light than the other type of visual photoreceptor, cone cells. Rods are concentrated at the outer edges of the retina and are used in peripheral vision. Rods are a little longer and leaner than cones but have the same structural basis. The Opsin or pigment is on the outer side, lying on the retinal pigment epithelium, completing the cell’s homeostasis. This epithelium end contains many stacked disks. Rods have a high area for visual pigment and thus substantial efficiency of light absorption. Like cones, rod cells have a synaptic terminal, an inner segment, and an outer segment. The synaptic terminal forms a synapse with another neuron, for example a bipolar cell. The inner and outer segments are connected by a cilium, which lines the distal segment. The inner segment contains organelles and the cell’s nucleus, while the rod outer segment, which is pointed toward the back of the eye, contains the light-absorbing materials. Activation of photopigments by light sends a signal by hyperpolarizing the rod cell, leading to the rod cell not sending its neurotransmitter, which leads to the bipolar cell then releasing its transmitter at the bipolar-ganglion synapse and exciting the synapse. “Cone cells,” or “cones,” are responsible for color vision and function best in relatively bright light. Cone cells are densely packed in the fovea centralis, a 0.3 mm diameter rod-free area with very thin, densely packed cones which quickly reduce in number towards the periphery of the retina. There are about six to seven million cones in a human eye and are most concentrated towards the macula. Cones are less sensitive to light than the rod cells in the retina (which support vision at low light levels) but allow the perception of color. They are also able to perceive finer detail and more rapid changes in images, because their response times to stimuli are faster than those of rods. In humans, cones are normally one of the three types, each with different pigment, namely: S-cones, M-cones and L-cones. Each cone is therefore sensitive to visible wavelengths of light that correspond to short-wavelength, medium-wavelength and long-wavelength light. The three types have peak wavelengths near 420-440 nm, 534-545 nm and 564-580 nm, respectively, depending on the individual.

Retinal Pigment Epithelium: The pigmented layer of hexagonal cells, present in vivo in mammals, just outside of the neurosensory retinal that is attached to the underlying choroid. These cells are densely packed with pigment granules, and shield the retinal from incoming light. The retinal pigment epithelium also serves as the limiting transport factor that maintains the retinal environment by supplying small molecules such as amino acid, ascorbic acid and D-glucose while remaining a tight barrier to choroidal blood borne substances.

Retinitis pigmentosa (RP): An inherited, degenerative eye disease that causes severe vision impairment due to the progressive degeneration of the rod photoreceptor cells in the retina. This form of retinal dystrophy manifests initial symptoms independent of age. The initial retinal degenerative symptoms of Retinitis pigmentosa are characterized by decreased night vision (nyctalopia) and the loss of the mid-peripheral visual field. The rod photoreceptor cells, which are responsible for low-light vision and are orientated in the retinal periphery, are the retinal processes affected first during non-syndromic forms of this disease. Visual decline progresses relatively quickly to the far peripheral field, eventually extending into the central visual field as tunnel vision increases. Visual acuity and color vision can become compromised due to accompanying abnormalities in the cone photoreceptor cells, which are responsible for color vision, visual acuity, and sight in the central visual field. The progression of disease symptoms occurs in a symmetrical manner, with both the left and right eyes experiencing symptoms at a similar rate. There are multiple genes that, when mutated, can cause the retinitis pigmentosa phenotype. Inheritance patterns of RP have been identified as autosomal dominant, autosomal recessive, X-linked, and maternally (mitochondrially) acquired, and are dependent on the specific RP gene mutations present in the parental generation.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a FGF polypeptide will possess a relatively high degree of sequence identity when aligned using standard methods.

Methods of alignment of sequences for comparison are well known in the art. Various programs and alignment algorithms are described in Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. USA* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. USA* 85:2444, 1988. Altschul, et al., *Nature Genet.,* 6:119, 1994 presents a detailed consideration of sequence alignment methods and homology calculations.

The NCBI Basic Local Alignment Search Tool (BLAST) (Altschul, et al., *J. Mol. Biol.* 215:403, 1990) is available from several sources, including the National Center for Biotechnology Information (NCBI, Bethesda, MD) and on the internet, for use in connection with the sequence analysis programs blastp, blastn, blastx, tblastn and tblastx. A description of how to determine sequence identity using this program is available on the NCBI website on the internet.

Homologs and variants of a polypeptide are typically characterized by possession of at least about 75%, for example at least about 80%, sequence identity counted over the full-length alignment with the amino acid sequence of the factor using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Subject: Human and non-human animals, including all vertebrates, such as mammals and non-mammals, such as non-human primates, mice, rabbits, sheep, dogs, cats, horses, cows, chickens, amphibians, and reptiles. In many embodiments of the described methods, the subject is a human.

Transactivator: A factor that acts to increase gene expression from a promoter. A transactivator gene expresses a transcription regulatory protein (generally a transcription factor) that binds directly or through interaction with another protein to one or more specific promoter regions. By binding to the promoter region, the transcription regulatory factor enhances the expression of a sequence operably linked to the promoter. The expression of one transactivator can activate the expression of several proteins, as long as all are operably linked to the specific promoter region.

Transgene: An exogenous gene.

Upstream: A relative position on a polynucleotide, wherein the "upstream" position is closer to the 5' end of the polynucleotide than the reference point. In the instance of a double-stranded polynucleotide, the orientation of 5' and 3' ends are based on the sense strand, as opposed to the antisense strand.

Vector: A nucleic acid molecule as introduced into a host cell, thereby producing a transformed host cell. A vector may include nucleic acid sequences that permit it to replicate in the host cell, such as an origin of replication. A vector may also include one or more therapeutic genes and/or selectable marker genes and other genetic elements known in the art. A vector can transduce, transform or infect a cell, thereby causing the cell to express nucleic acids and/or proteins other than those native to the cell. A vector optionally includes materials to aid in achieving entry of the nucleic acid into the cell, such as a viral particle, liposome, protein coating or the like.

Virus: Microscopic infectious organism that reproduces inside living cells. A virus consists essentially of a core of a single nucleic acid surrounded by a protein coat and has the ability to replicate only inside a living cell. "Viral replication" is the production of additional virus by the occurrence of at least one viral life cycle. Viral vectors are known in the art, and include, for example, adenovirus, AAV, lentivirus and herpes virus.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting.

Overview

It is disclosed herein that, surprisingly, the delivery of a gene encoding a CRX protein to retinal cells can be used to treat CRX autosomal dominant retinopathies. The method disclosed herein include administering to a subject an effective amount of a nucleic acid molecule comprising a retinal specific promoter operably linked to a nucleic acid molecule encoding the CRX protein, thereby treating the CRX autosomal dominant retinopathy. The subject can be a human.

In some embodiments, the CRX autosomal dominant retinopathy is Leber congenital amaurosis (LCA), retinitis pigmentosa, or cone rod dystrophy. In one non-limiting example, the CRX autosomal dominant retinopathy is the LCA.

In additional embodiments, the methods can include administering to the subject a viral vector comprising the retinal specific promoter operably linked to the nucleic acid molecule encoding a CRX protein. In some non-limiting examples, the vector can be a lentiviral vector or an adeno-associated virus (AAV) vector, such as an AAV2, AAV5, or AAV8 virus vector. In more embodiments, the methods include administering to the subject a nanoparticle or a dendrimer comprising the nucleic acid molecule.

In further embodiments, the promoter is a human CRX promoter. In a specific non-limiting example, the human CRX promoter comprises SEQ ID NO: 1.

In yet other embodiments, the CRX protein includes an amino acid sequence at least 95% identical to SEQ ID NO: 2. In a specific non-limiting example, the CRX protein includes the amino acid sequence of SEQ ID NO: 2.

In more embodiments, the nucleic acid molecule is administered sub-retinally or to the retina of the subject.

In additional embodiments, the method increases Rhodopsin expression in the retina of the subject. The disclosed methods can include selecting the subject of interest, such as a subject with a CRX autosomal dominant retinopathy.

Compositions for use in the disclosed methods are provided. Also disclosed is a promoter comprising, or consisting of, the nucleotide sequence of SEQ ID NO: 1. The promoter can be operably linked to a heterologous nucleic acid encoding a polypeptide. Vectors are also disclosed that include the promoter, such as, but not limited to, viral vectors. In specific non-limiting example, the viral vector is an AAV vector.

CRX Polypeptides, Polynucleotides Encoding CRX, and CRX Promoters

CRX is an OTX-family homeodomain transcription factor required for appropriate development of retinal photoreceptor cells (Chen et al., Neuron, 19, 1017-1030 Furakawa et al., *Cell,* 91, 531-541). In vivo, CRX is specifically expressed in the retina and the pineal gland. Its function is primarily related to regulating gene expression in retinal photoreceptor cells necessary for proper vision and pinealocytes involved in circadian rhythms. Loss of CRX in mice results in loss of visual function (Furakawa et al., *Nature genetics,* 23, 466-470.) as the photoreceptors don't express necessary phototransduction genes and do not elaborate outer segments, specialized organelles containing visual pigments Opsins and phototransduction-related proteins.

In humans, in vivo the CRX gene (Gene ID: 1406; Ensembl: ENSG00000105392; MIM #602225, Dec. 31, 2019, incorporated herein by reference) is located on chromosome 19q13.33 and encodes a 299 amino-acid DNA binding protein. An exemplary amino acid sequence of human CRX is provided below, see UniProtKB No. 043186, as available on Dec. 31, 2019, incorporated herein by reference:

```
                                            (SEQ ID NO: 2)
MMAYMNPGPH YSVNALALSG PSVDLMHQAV PYPSAPRKQR

RERTTFTRSQ LEELEALFAK TQYPDVYARE EVALKINLPE

SRVQVWFKNR RAKCRQQRQQ QKQQQQPPGG QAKARPAKRK

AGTSPRPSTD VCPDPLGISD SYSPPLPGPS GSPTTAVATV

SIWSPASESP LPEAQRAGLV ASGPSLTSAP YAMTYAPASA

FCSSPSAYGS PSSYFSGLDP YLSPMVPQLG GPALSPLSGP

SVGPSLAQSP TSLSGQSYGA YSPVDSLEFK DPTGTWKFTY

NPMDPLDYKD QSAWKFQIL
```

In some embodiments, the CRX protein comprises the amino acid sequence set forth as SEQ ID NO: 2. In other embodiments, the CRX protein comprises an amino acid sequence at least about 90%, 91%, 92%, 93%, 94%, 95%, 96%, 97%, 98% or 99% identical to SEQ ID NO: 2. In some non-limiting examples, the CRX protein is at least 95% identical to SEQ ID NO: 2. The CRX protein can function as a transactivator.

CRX is a transcription factor that regulates the expression of a large number of rod and cone photoreceptor genes. Transactivation by CRX can be tested in vitro (using promoters that are CRX regulated to drive the expression of GFP or other reporter genes) or in vivo using models (including Crx-ko mice). This transcriptional activation function is needed for photoreceptor development and function.

SEQ ID NO: 2 is 299 amino acids in length. The DNA binding domain is at the N terminus and comprises residues 39 to 108, whereas transcriptional activation domain of the protein is located towards the C terminus (from residues 113 to 284). In some embodiments, a CRX protein of use is at least about 95%, 96%, 97%, 98%, or 99% identical to SEQ ID NO: 2, and includes residues 39 to 108 of SEQ ID NO: 2. In other embodiments, a CRX protein of use is at least about 95%, 96%, 97%, 98%, or 99% identical to SEQ ID NO: 2, and includes amino acids, and includes residues 113 to 284 of SEQ ID NO: 2. In further embodiments, a CRX protein of use is at least about 95% identical to SEQ ID NO: 2, and includes residues 39 to 108 and residues 113 to 284 of SEQ ID NO: 2. In more embodiments, a CRX protein of use is at least about 96%, 97%, 98% or 99% identical to SEQ ID NO: 2, and includes residues 39 to 108 and residues 113 to 284 of SEQ ID NO: 2. This CRX protein can funcation as a transactivator.

In some embodiments, the CRX protein includes the OTX tail, residues 284 to 299 of SEQ ID NO: 2. In other embodiments, a CRX protein of use is at least about 95%, 96%, 97%, 98%, or 99% identical to SEQ ID NO: 2, and includes residues 284 to 299 of SEQ ID NO: 2. In further embodiments, a CRX protein of use is at least about 95% identical to SEQ ID NO: 2, and includes residues 39 to 108, residues 113 to 284 of SEQ ID NO: 2 and residues 284 to 299 of SEQ ID NO: 2. In more embodiments, a CRX protein of use is at least about 96%, 97%, 98% or 99% identical to SEQ ID NO: 2, and includes residues 39 to 108, residues 113 to 284, and residues 284 to 299 of SEQ ID NO: 2. This CRX protein can funcation as a transactivator.

CRX protein exhibits high sequence homology in primates (chimpanzee 99%, crab-eating macaque 100%, gorilla 100%, marmoset 98%) and in model organisms (cat 93%, chicken 57%, dog 97%, mouse 89%, rat 97%, zebrafish 57%). Thus, in some embodiments, the CRX protein can include the corresponding amino acid from the CRX protein of another species. This CRX protein can funcation as a transactivator.

Polynucleotides encoding a CRX protein are of use in the disclosed methods. These polynucleotides include DNA, cDNA, and RNA sequences that encode the CRX protein. Silent mutations in the coding sequence result from the degeneracy (i.e., redundancy) of the genetic code, whereby more than one codon can encode the same amino acid residue. Thus, for example, leucine can be encoded by CTT, CTC, CTA, CTG, TTA, or TTG; serine can be encoded by TCT, TCC, TCA, TCG, AGT, or AGC; asparagine can be encoded by AAT or AAC; aspartic acid can be encoded by GAT or GAC; cysteine can be encoded by TGT or TGC; alanine can be encoded by GCT, GCC, GCA, or GCG; glutamine can be encoded by CAA or CAG; tyrosine can be encoded by TAT or TAC; and isoleucine can be encoded by ATT, ATC, or ATA. Tables showing the standard genetic code can be found in various sources (e.g., L. Stryer, 1988, Biochemistry, 3.sup.rd Edition, W.H. 5 Freeman and Co., NY). Degenerate variants are also of use in the methods disclosed herein.

Nucleic acid molecules encoding a CRX protein can readily be produced by one of skill in the art using the amino acid sequences provided herein and the genetic code. Nucleic acid sequences encoding the CRX protein can be prepared by any suitable method including, for example, cloning of appropriate sequences or by direct chemical synthesis by methods such as the phosphotriester method of Narang et al., *Meth. Enzymol.* 68:90-99, 1979; the phosphodiester method of Brown et al., *Meth. Enzymol.* 68:109-151, 1979; the diethylphosphoramidite method of Beaucage et al., *Tetra. Lett.* 22:1859-1862, 1981; the solid phase phosphoramidite triester method described by Beaucage & Caruthers, *Tetra. Letts.* 22 (20): 1859-1862, 1981, for example, using an automated synthesizer as described in, for example, Needham-VanDevanter et al., *Nucl. Acids Res.* 12:6159-6168, 1984 and the solid support method of U.S. Pat. No. 4,458,066. Chemical synthesis produces a single-strand (ss) oligonucleotide, which can be converted into double-strand (ds) DNA by hybridization with a complementary sequence or by polymerization with a DNA polymerase using the single strand as a template. Exemplary nucleic acids that include sequences encoding a CRX protein can be prepared by cloning techniques.

A nucleic acid molecule encoding a CRX protein can be cloned or amplified by in vitro methods, such as the polymerase chain reaction (PCR), the ligase chain reaction (LCR), the transcription-based amplification system (TAS), the self-sustained sequence replication system (3SR), and the QB replicase amplification system (QB). For example, a polynucleotide encoding the protein can be isolated by a polymerase chain reaction of cDNA using primers based on the DNA sequence of the molecule. A wide variety of cloning and in vitro amplification methodologies are well-known to persons skilled in the art. PCR methods are described in, for example, U.S. Pat. No. 4,683,195; Mullis et al., *Cold Spring Harbor Symp. Quant. Biol.* 51:263, 1987; and Erlich, ed., *PCR Technology*, (Stockton Press, NY, 1989). Polynucleotides also can be isolated by screening genomic or cDNA libraries with probes selected from the sequences of the desired polynucleotide under stringent hybridization conditions.

Typically, a polynucleotide sequence encoding a CRX protein is operably linked to transcriptional control sequences including, for example a promoter and a polyadenylation signal. Any promoter can be used that is a polynucleotide sequence recognized by the transcriptional machinery of the host cell (or introduced synthetic machinery) that is involved in the initiation of transcription. A polyadenylation signal is a polynucleotide sequence that directs the addition of a series of nucleotides on the end of the mRNA transcript for proper processing and trafficking of the transcript out of the nucleus into the cytoplasm for translation.

Exemplary promoters include viral promoters, such as cytomegalovirus immediate early gene promoter ("CMV"), herpes simplex virus thymidine kinase ("tk"), SV40 early transcription unit, polyoma, retroviruses, papilloma virus, hepatitis B virus, and human and simian immunodeficiency viruses. Other promoters include promoters isolated from mammalian genes, such as the immunoglobulin heavy chain, immunoglobulin light chain, T cell receptor, HLA DQ α and DQ β, β-interferon, interleukin-2, interleukin-2 receptor, MHC class II, HLA-DRα, β-actin, muscle creatine kinase, prealbumin (transthyretin), elastase I, metallothionein, collagenase, albumin, fetoprotein, β-globin, c-fos, c-HA-ras, neural cell adhesion molecule (NCAM), α1-antitrypsin, H2B (TH2B) histone, type I collagen, glucose-regulated proteins (GRP94 and GRP78), rat growth hormone, human serum amyloid A (SAA), troponin I (TNI), platelet-derived growth factor, and dystrophin, as well as promoters specific for retinal cells.

The promoter can be either inducible or constitutive. An inducible promoter is a promoter that is inactive or exhibits low activity except in the presence of an inducer substance. Additional examples of promoters include, but are not limited to, MT II, MMTV, collagenase, stromelysin, SV40, murine MX gene, α-2-macroglobulin, MHC class I gene h-2 kb, HSP70, proliferin, tetracycline inducible, tumor necrosis factor, or thyroid stimulating hormone gene promoter. One example of an inducible promoter is the interferon inducible ISG54 promoter (see Bluyssen et al., Proc. Natl Acad. Sci. 92:5645-5649, 1995, herein incorporated by reference). In some embodiments, the promoter is a constitutive promoter that results in high levels of transcription upon introduction into a host cell in the absence of additional factors.

In some embodiments, the promoter is a retinal specific promoter. Exemplary retinal photoreceptor specific promoters are: Rhodopsin kinase, NRL, IRBP, cone Opsin or Rhodopsin promoters, and the CRX promoter.

In some embodiments, the promoter is a CRX promoter. The CRX promoters disclosed herein can be operably linked to a nucleotide molecule encoding any protein, to obtain expression of the protein in the retina. In some embodiments, the CRX promoter is operably linked to a nucleic acid molecule encoding the CRX protein.

The CRX 5' untranslated region of human CRX is provided in NCBI Reference sequence NG_008605.1, as available on Dec. 31, 2019, incorporated herein by reference.

In some embodiments, a CRX promoter is provided that includes, or consists of:

(SEQ ID NO: 1)

CGTCGACGGGTCAGACGGCCCCTCCCTCTCTTGCTGTCATCCCTGGCTCT

TCAAGCTAATGAGACCTGTCCTGATTCCTCAGCCAGGCCTGTAGCCTTAA

TCTCTCCTAGCAGGGGGTTTGGGGGAGGGAGGAGGAGAAAGAAAGGGCCC

CTTATGGCTGAGACACAATGACCCAGCCACAAGGAGGGATTACCGGGGAA

GTGAAACAGACCCGTGTGGGACCCAGGAGCTCAGGGACATATTAATATCT

AGAGAGACAGACGGTCGACAGACACCAGTTAGACCTAAGGAAGGACTTCC

CTGAGGAGTAGGGGCTTATGGTCACCGGCAGGAGCTGGGGCCTCCCTTCC

CCATCAGCCCTAATTGCCAAGATGTCATGGGGGGAAGAGGAGGGGATTAA

GCAGACGGGTGCCCCTCCCCCTCCCAGCCAATGTCACCTCCTGGTGCCCA

GTCGAGTCCCCCACCTTGGCCGGGATTACCCTCCGAGTTCCAGGCCATAA

CAAGTGACATCACTCCCGGCCCAGGCTTAAAATCTCCCCACGTGAGGGGA

CGTGTTTCCTTCAGCCTCTGCTGTCTGGCCGCTCTGTCTAGGTCCTGGGC

CACGGGAGAGCCCCGTCCCTCCTTTCTGAAG

Three fragments from the human CRX 5' untranslated region (NCBI: NG_008605.1) were amplified from human genomic DNA and combined to produce 631 base pair length promoter element that specifically expresses the reporter gene in rod and cone photoreceptors. In SEQ ID NO: 1, 189 nucleotides correspond to positions 3085-3274 of NCBI Reference sequence NG_008605.1; 69 correspond to 3323-3392 of NCBI Reference sequence NG_008605.1, and 361 correspond to 4808-5169 of NCBI Reference sequence NG_008605.1. The NCBI Reference Sequences are incorporated herein by reference as available on Jan. 27, 2020. Note that 4999-5169 is exon 1; therefore, this human CRX promoter element contains 1st exon of the human CRX gene.

In other embodiments, the promoter can be at least about 95%, 96%, 97%, 98%, or 99% identical to SEQ ID NO: 1, wherein the promoter provides expression in cells of the retina.

SEQ ID NO: 1 includes five CRX binding sites, which bind CRX, as follows:

| Start | Stop | Strand |
|---|---|---|
| 393 | 401 | negative |
| 391 | 403 | negative |
| 96 | 104 | positive |
| 388 | 403 | positive |
| 467 | 482 | positive |

In some embodiments the CRX promoter is at least about 95%, 96%, 97%, 98% or 99% identical to SEQ ID NO: 1, and includes at least 1, 2, 3, 4 or all 5 CRX binding sites. In more embodiments, the CRX promoter is at least about 95%, 96%, 97%, 98% or 99% identical to SEQ ID NO: 1, and includes all 5 CRX binding sites. In some specific non-limiting examples, the CRX promoter is at least about 95%, 96%, 97%, 98% or 99% identical to SEQ ID NO: 1 and includes nucleotides 96-104, 388-403 and 467-482 of SEQ ID NO: 1.

The disclosed promoters include AP-2Beta, FOXO1, NRF2, PBX3, and ZIC1 binding sites. Thus, in some embodiments, the promoter is at least about 95%, 96%, 97%, 98% or 99% identical to SEQ ID NO: 1, and retains the AP-2Beta, FOXO1, NRF2, PBX3, and/or ZIC1 binding sites. In some embodiments, the promoter retains all of these binding sites.

Optionally, transcription control sequences include one or more enhancer elements, which are binding recognition sites for one or more transcription factors that increase transcription above that observed for the minimal promoter alone, and also be operably linked to the polynucleotide encoding the CRX promoter and/or the nucleic acid molecule encoding the CRX protein. With regard to the nucleic acid molecule encoding the CRX protein, introns can also be included that help stabilize mRNA and increase expression.

In some embodiments of the compositions and methods described herein, a nucleic acid sequence that encodes a CRX protein is incorporated into a vector capable of expression in a host cell, using established molecular biology procedures. For example, nucleic acids, such as cDNAs, that encode a CRX protein can be manipulated with standard procedures, such as restriction enzyme digestion, fill-in with DNA polymerase, deletion by exonuclease, extension by terminal deoxynucleotide transferase, ligation of synthetic or cloned DNA sequences, site-directed sequence-alteration via single-stranded bacteriophage intermediate, or use of specific oligonucleotides in combination with PCR or other in vitro amplification. These vectors can include a CRX promoter operably linked to a nucleic acid molecule encoding a CRX protein.

Exemplary procedures sufficient to guide one of ordinary skill in the art through the production of a vector capable of expression in a host cell that includes a CRX promoter, and/or a polynucleotide sequence encoding a CRX protein can be found, for example, in Sambrook et al., *Molecular Cloning: A Laboratory Manual,* 2d ed., Cold Spring Harbor Laboratory Press, 1989; Sambrook et al., *Molecular Cloning: A Laboratory Manual,* 3d ed., Cold Spring Harbor Press, 2001; Ausubel et al., *Current Protocols in Molecular Biology*, Greene Publishing Associates, 1992 (and Supplements to 2003); and Ausubel et al., *Short Protocols in Molecular Biology: A Compendium of Methods from Current Protocols in Molecular Biology,* 4th ed., Wiley & Sons, 1999.

It may be desirable to include a polyadenylation signal to effect proper termination and polyadenylation of the gene transcript. Exemplary polyadenylation signals have been isolated from beta globin, bovine growth hormone, SV40, and the herpes simplex virus thymidine kinase genes.

The disclosed nucleic acid molecules can be included in a nanodispersion system, see, e.g., U.S. Pat. No. 6,780,324; U.S. Pat. Publication No. 2009/0175953. For example, a nanodispersion system includes a biologically active agent and a dispersing agent (such as a polymer, copolymer, or low molecular weight surfactant). Exemplary polymers or copolymers include polyvinylpyrrolidone (PVP), poly(D,L-lactic acid) (PLA), poly(D,L-lactic-co-glycolic acid (PLGA), poly (ethylene glycol). Exemplary low molecular weight surfactants include sodium dodecyl sulfate, hexadecyl pyridinium chloride, polysorbates, sorbitans, poly(oxyethylene) alkyl ethers, poly(oxyethylene) alkyl esters, and combinations thereof. In one example, the nanodispersion system includes PVP and ODP or a variant thereof (such as 80/20 w/w). In some examples, the nanodispersion is prepared using the solvent evaporation method, see for example, Kanaze et al., *Drug Dev. Indus. Pharm.* 36:292-301, 2010; Kanaze et al., *J. Appl. Polymer Sci.* 102:460-471, 2006.

Dendrimers are synthetic three-dimensional macromolecules that are prepared in a step-wise fashion from simple branched monomer units, the nature and functionality of which can be easily controlled and varied. Dendrimers consist of an initiator core, surrounded by a layer of a selected polymer that is grafted to the core, forming a branched macromolecular complex. Dendrimers are typically produced using polymers such as poly(amidoamine) or poly(L-lysine). A dendrimer can be synthesized from the repeated addition of building blocks to a multifunctional core (divergent approach to synthesis), or towards a multifunctional core (convergent approach to synthesis) and each addition of a three-dimensional shell of building blocks leads to the formation of a higher generation of the dendrimers. Polypropylenimine dendrimers contain 100% protonable nitrogens and up to 64 terminal amino groups. Protonable groups are usually amine groups which are able to accept protons at neutral pH. For nucleic acid molecules, dendrimers can be formed from polyamidoamine and phosphorous containing compounds with a mixture of amine/amide or N—P($O_2$) S as the conjugating units. Dendrimers of use for delivery of nucleic acid molecules is disclosed, for example, in PCT Publication No. 2003/033027, imported herein by reference.

The CRX promoter, and/or the polynucleotides encoding the CRX protein, include a recombinant DNA which is incorporated into a vector in an autonomously replicating plasmid or virus or into the genomic DNA of a prokaryote or eukaryote, or which exists as a separate molecule (such as a cDNA) independent of other sequences. Viral vectors that include the CRX promoter, and/or the CRX protein, can also be prepared. Numerous viral vectors are known in the art, including polyoma; SV40 (Madzak et al., 1992, J. Gen. Virol., 73:15331536); adenovirus (Berkner, 1992, Cur. Top. Microbiol. Immunol., 158:39-6; Berliner et al., 1988, Bio Techniques, 6:616-629; Gorziglia et al., 1992, J. Virol., 66:4407-4412; Quantin et al., 1992, Proc. Nad. Acad. Sci. USA, 89:2581-2584; Rosenfeld et al., 1992, Cell, 68:143-155; Wilkinson et al., 1992, Nucl. Acids Res., 20:2233-2239; Stratford-Perricaudet et al., 1990, Hum. Gene Ther., 1:241-256); vaccinia virus (Mackett et al., 1992, Biotechnology, 24:495-499); adeno-associated virus (Muzyczka, 1992, Curr. Top. Microbiol. Immunol., 158:91-123; On et al., 1990, Gene, 89:279-282); herpes viruses, including HSV and EBV (Margolskee, 1992, Curr. Top. Microbiol. Immunol., 158:67-90; Johnson et al., 1992, J. Virol., 66:29522965; Fink et al., 1992, Hum. Gene Ther. 3:11-19; Breakfield et al., 1987, Mol. Neurobiol., 1:337-371; Fresse et al., 1990, Biochem. Pharmacol., 40:2189-2199); Sindbis viruses (H. Herweijer et al., 1995, Human Gene Therapy 6:1161-1167; U.S. Pat. Nos. 5,091,309 and 5,2217,879); alphaviruses (S. Schlesinger, 1993, Trends Biotechnol. 11:18-22; I. Frolov et al., 1996, Proc. Natl. Acad. Sci. USA 93:11371-11377); and retroviruses of avian (Brandyopadhyay et al., 1984, Mol. Cell Biol., 4:749-754; Petropouplos et al., 1992, J. Virol., 66:3391-3397), murine (Miller, 1992, Curr. Top. Microbiol. Immunol., 158:1-24; Miller et al., 1985, Mol. Cell Biol., 5:431-437; Sorge et al., 1984, Mol. Cell Biol., 4:1730-1737; Mann et al., 1985, J. Virol., 54:401-407), and human origin (Page et al., 1990, J. Virol., 64:5370-5276; Buchschalcher et al., 1992, J. Virol., 66:2731-2739). Baculovirus (*Autographa californica* multinuclear polyhedrosis virus; AcMNPV) vectors are also known in the art and may be obtained from commercial sources (such as PharMingen, San Diego, Calif.; Protein Sciences Corp., Meriden, Conn.; Stratagene, La Jolla, Calif.).

Thus, in one embodiment, the CRX promoter, and/or the nucleic acid molecule encoding the CRX protein, is included in a viral vector. Suitable vectors include retrovirus vectors, orthopox vectors, avipox vectors, fowlpox vectors, capripox vectors, suipox vectors, adenoviral vectors, herpes virus vectors, alpha virus vectors, baculovirus vectors, Sindbis virus vectors, vaccinia virus vectors, lentivirus vectors and poliovirus vectors. Specific exemplary vectors are poxvirus vectors, such as vaccinia virus, fowlpox virus and a highly attenuated vaccinia virus (MVA), adenovirus, baculovirus, yeast, and the like. Adeno-associated virus vectors (AAV) are disclosed in additional detail below, and are of use in the disclosed methods.

AAV Vectors

Disclosed herein are methods and compositions that include utilize one or more vectors, such as a viral vector, such as a retroviral vector or an adenoviral vector, or an AAV vector that includes a CRX promoter, optionally operably linked to a nucleic acid molecule including a CRX protein. Defective viruses, that entirely or almost entirely lack viral genes, can be used. Use of defective viral vectors allows for administration to specific cells without concern that the vector can infect other cells. The adenovirus vectors of use include replication competent, replication deficient, gutless forms thereof. The AAV vectors of use are replication deficient. Without being bound by theory, adenovirus vectors are known to exhibit strong expression in vitro, excellent titer, and the ability to transduce dividing and non-dividing cells in vivo (Hitt et al., Adv in Virus Res 55:479-505, 2000). When used in vivo these vectors lead to strong but transient gene expression due to immune responses elicited to the vector backbone. In some non-limiting examples, a vector of use is an attenuated adenovirus vector, such as the vector described by Stratford-Perricaudet et al. (*J. Clin. Invest.,* 90:626-630 1992; La Salle et al., Science 259:988-990, 1993); or a defective AAV vector (Samulski et al., *J. Virol.,* 61:3096-3101, 1987; Samulski et al., *J. Virol.,* 63:3822-3828, 1989; Lebkowski et al., *Mol. Cell. Biol.,* 8:3988-3996, 1988).

Recombinant AAV vectors are characterized in that they are capable of directing the expression and the production of the selected transgenic products in targeted cells. Thus, the recombinant vectors comprise at least all of the sequences of AAV essential for encapsidation and the physical structures for infection of target cells.

AAV belongs to the family Parvoviridae and the genus Dependovirus. AAV is a small, non-enveloped virus that packages a linear, single-stranded DNA genome. Both sense and antisense strands of AAV DNA are packaged into AAV capsids with equal frequency. In some embodiments, the AAV DNA includes a nucleic acid including a recombinant CRX promoter, as disclosed herein, operably linked to a nucleic acid molecule encoding a CRX protein, such as a human CRX protein. Further provided are recombinant vectors, such as recombinant adenovirus vectors and recombinant adeno-associated virus (rAAV) vectors comprising a nucleic acid molecule(s) disclosed herein. In some embodiments, the AAV is rAAV8, and/or AAV2. However, the AAV serotype can be any other suitable AAV serotype, such as AAV1, AAV2, AAV3, AAV4, AAV5, AAV6, AAV7, AAV9, AAV10, AAV11 or AAV12, or a hybrid of two or more AAV serotypes.

The AAV genome is characterized by two inverted terminal repeats (ITRs) that flank two open reading frames (ORFs). In the AAV2 genome, for example, the first 125 nucleotides of the ITR are a palindrome, which folds upon itself to maximize base pairing and forms a T-shaped hairpin structure. The other 20 bases of the ITR, called the D sequence, remain unpaired. The ITRs are cis-acting sequences important for AAV DNA replication; the ITR is the origin of replication and serves as a primer for second-strand synthesis by DNA polymerase. The double-stranded DNA formed during this synthesis, which is called replicating-form monomer, is used for a second round of self-priming replication and forms a replicating-form dimer. These double-stranded intermediates are processed via a strand displacement mechanism, resulting in single-stranded DNA used for packaging and double-stranded DNA used for transcription. Located within the ITR are the Rep binding elements and a terminal resolution site (TRS). These features are used by the viral regulatory protein Rep during AAV replication to process the double-stranded intermediates. In addition to their role in AAV replication, the ITR is also essential for AAV genome packaging, transcription, negative regulation under non-permissive conditions, and site-specific integration (Daya and Berns, *Clin Microbiol Rev* 21 (4): 583-593, 2008). In some embodiments, these elements are included in the AAV vector.

The left ORF of AAV contains the Rep gene, which encodes four proteins—Rep78, Rep 68, Rep52 and Rep40. The right ORF contains the Cap gene, which produces three viral capsid proteins (VP1, VP2 and VP3). The AAV capsid contains 60 viral capsid proteins arranged into an icosahedral symmetry. VP1, VP2 and VP3 are present in a 1:1:10 molar ratio (Daya and Berns, *Clin Microbiol Rev* 21 (4): 583-593, 2008). In some embodiments, these elements are included in the AAV vector.

AAV vectors can be used for gene therapy. Exemplary AAV of use are AAV2, AAV5, AAV6, AAV8 and AAV9. Adenovirus, AAV2 and AAV8 are capable of transducing cells in the retina. Thus, any of a rAAV2 or rAAV8 vector can be used in the methods disclosed herein. However, rAAV6 and rAAV9 vectors are also of use.

Although AAV infects humans and some other primate species, it is not known to cause disease and elicits a very mild immune response. Gene therapy vectors that utilize AAV can infect both dividing and quiescent cells and persist in an extrachromosomal state without integrating into the genome of the host cell. AAV2 preferentially infects cells of the human retina. Because of the advantageous features of AAV, the present disclosure contemplates the use of an rAAV for the methods disclosed herein.

AAV possesses several additional desirable features for therapy, including the ability to bind and enter target cells, enter the nucleus, the ability to be expressed in the nucleus for a prolonged period of time, and low toxicity. AAV can be used to transfect cells, and suitable vector are known in the art, see for example, U.S. Published Patent Application No. 2014/0037585, incorporated herein by reference. Methods for producing rAAV suitable for gene therapy are well known in the art (see, for example, U.S. Published Patent Application Nos. 2012/0100606; 2012/0135515; 2011/0229971; and 2013/0072548; and Ghosh et al., *Gene Ther* 13 (4): 321-329, 2006), and can be utilized with the methods disclosed herein.

In some embodiments, the vector is a rAAV8 vector, a rAAV2 vector, a rAAV9 vector. In a specific non-limiting example, the vector is an AAV8 vector. AAV8 vectors are disclosed, for example, in U.S. Pat. No. 8,692,332, which is incorporated by reference herein. The location and sequence of the capsid, rep 68/78, rep 40/52, VP1, VP2 and VP3 are disclosed in this U.S. Pat. No. 8,692,332. The location and hypervariable regions of AAV8 are also provided. In some embodiments, the vector is an AAV2 variant vector, such as AAV7m8.

The vectors of use in the methods disclosed herein can contain nucleic acid sequences encoding an intact AAV capsid which may be from a single AAV serotype (e.g., AAV2, AAV6, AAV8 or AAV9). As disclosed in U.S. Pat. No. 8,692,332, vectors of use can also be recombinant, and thus can contain sequences encoding artificial capsids which contain one or more fragments of the AAV8 capsid fused to heterologous AAV or non-AAV capsid proteins (or fragments thereof). These artificial capsid proteins are selected from non-contiguous portions of the AAV2, AAV6, AAV8 or AAV9 capsid or from capsids of other AAV serotypes. For example, a rAAV vector may have a capsid protein comprising one or more of the AAV8 capsid regions selected from the VP2 and/or VP3, or from VP1, or fragments thereof selected from amino acids 1 to 184, amino acids 199 to 259; amino acids 274 to 446; amino acids 603 to 659; amino acids 670 to 706; amino acids 724 to 738 of the AAV8 capsid, which is presented as SEQ ID NO: 2 in U.S. Pat. No. 8,692,332. In another example, it may be desirable to alter the start codon of the VP3 protein to GTG. Alternatively, the rAAV may contain one or more of the AAV serotype 8 capsid protein hypervariable regions, for example aa 185-198; aa 260-273; aa447-477; aa495-602; aa660-669; and aa707-723 of the AAV8 capsid which is presented as SEQ ID NO: 2 in U.S. Pat. No. 8,692,332.

In some embodiments, a recombinant adeno-associated virus (rAAV) is generated having an AAV serotype 2 capsid. To produce the vector, a host cell which can be cultured that contains a nucleic acid sequence encoding an AAV serotype 2 capsid protein, or fragment thereof, as defined herein; a functional rep gene; a minigene composed of, at a minimum, AAV inverted terminal repeats (ITRs) and a transgene, such as encoding a CRX protein, optionally operably linked to a CRX promoter; and sufficient helper functions to permit packaging in the AAV2 capsid protein. The components required to be cultured in the host cell to package an AAV minigene in an AAV capsid may be provided to the host cell in trans. Alternatively, any one or more of the required components (e.g., minigene, rep sequences, cap sequences, and/or helper functions) may be provided by a stable host cell which has been engineered to contain one or more of the required components using methods known to those of skill in the art. In some embodiments, a stable host cell will contain the required component(s) under the control of an inducible promoter or a tissue specific promoter. Similar methods can be used to generate a rAAV2, rAAV8 or rAAV9 vector and/or virion.

A retinal specific promoter can be included in the AAV vectors. In some embodiments, the promoter is a Rhodopsin Kinase (RK) promoter. The Rhodopsin kinase promoter directs expression in rod and cone cells. This promoter has been optimized for expression (see Khani et al., Invest. Opthamol. Vis. Science, 48:3954-3961, 2007, incorporated herein by reference). The sequence of this promoter is provided in FIG. 1 of this reference. Additional promoters include, but are not limited to, the NRL, CRX, IRBP, or Rhodopsin promoters. In specific non-limiting examples, a CRX promoter, as disclosed above, is operably linked to a nucleic acid molecule encoding the CRX protein and included in the AAV vector.

In other embodiments, component(s), such as, but not limited to, a transgene encoding a CRX protein, can be under the control of a constitutive promoter. A non-limiting example of a suitable constitutive promoter is the cytomegalovirus promoter. Additional non-limiting examples are the ubiquitin or a chicken β-actin promoter. Promoters of use are also disclosed in the section above. Additional promoters are disclosed above.

In still another alternative, a selected stable host cell may contain selected component(s) under the control of a constitutive promoter and other selected component(s) under the control of one or more inducible promoters, such as for the production of rAAV in a packaging host cell. For example, a stable host cell may be generated which is derived from 293 cells (which contain E1 helper functions under the control of a constitutive promoter), but which contains the rep and/or cap proteins under the control of inducible promoters. Still other stable host cells may be generated by one of skill in the art.

The minigene, rep sequences, cap sequences, and helper functions required for producing a rAAV can be delivered to the packaging host cell in the form of any genetic element which transfer the sequences carried thereon. The selected genetic element may be delivered by any suitable method, including those described herein. The methods used to construct vectors are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y. Similarly, methods of generating rAAV virions are well known and the selection of a suitable method is not a limitation on the present invention. See, e.g., K. Fisher et al, J. Virol., 70:520-532 (1993) and U.S. Pat. No. 5,478,745. In some embodiments, selected AAV components can be readily isolated using techniques available to those of skill in the art from an AAV serotype, including AAV8. Such AAV may be isolated or obtained from academic, commercial, or public sources (e.g., the American Type Culture Collection, Manassas, Va.). Alternatively, the AAV sequences may be obtained through synthetic or other suitable means by reference to published sequences such as are available in the literature or in databases such as, e.g., GENBANK®.

Pharmaceutical Compositions and Methods of Treatment

Methods are disclosed herein for treating a CRX autosomal dominant retinopathy in a subject. These methods include administering to the subject an effective amount of a nucleic acid molecule comprising a retinal specific promoter, such as a CRX promoter, operably linked to a nucleic acid molecule encoding a CRX protein. In some embodiments, the CRX autosomal dominant retinopathy is Leber congenital amaurosis (LCA), retinitis pigmentosa, or cone rod dystrophy. In a specific non-limiting example, the CRX autosomal dominant retinopathy is LCA. The methods can include selecting a subject that has the CRX autosomal dominant retinopathy, such as a subject with LCA, retinitis pigmentosa, or cone rod dystrophy. In a specific non-limiting example, the method includes selecting and treating a subject with LCA. In some embodiments, the methods can include selecting a subject that does not have a CRX autosomal recessive retinopathy and/or a CRX X-linked retinopathy. In any of the embodiments, the retinal specific promoter can be a CRX promoter, as disclosed above. In some embodiments, the disclosed methods increase Rhodopsin and cone L/M Opsin expression in the retina of the subject.

Mutations in the CRX gene were identified in patients with retinal dystrophies ranging from severe early-onset LCA (LCA7, MIM #613829) through adult-onset cone-rod dystrophy (CORD2, MIM #120970), retinitis pigmentosa (RP, MIM #268000) to mild late-onset macular dystrophy (Swain et al., 1997, Neuron, 19, 1329-1336., Freund et al., 1997, *Cell,* 91, 543-553; Freund et al., 1998, *Nature genetics,* 18, 311-312; Huang et al., 2012, *Biochem Biophys Res Commun,* 426, 498-503). CRX is the only gene associated with all three of LCA, RP and CORD. A majority of mutations arise de novo and are present in heterozygous form, thereby showing autosomal dominant inheritance. Approximately 50 likely pathological mutations have been described to date, half of these co-segregate with the disease phenotype. Reported mutations are 39% missense, 4% nonsense, 37% deletion, 16% insertion and 4% indel (insertion and deletion) sequence changes. Classes of mutations are summarized in the table below:

| Mutation class | Mutation type | Allele type | DNA binding |
|---|---|---|---|
| I | Missense | hypomorphic | Reduced |
| II | Missense | antimorphic | Variable |
| III | Frameshift or nonsense | antimorphic | Preserved |
| IV | Frameshift | antimorphic | Reduced |

Any autosomal dominant mutation, including those in mutation class I-IV, can be treated using the methods disclosed herein. Thus, a subject can be selected that has an autosomal dominant CRX mutation from one of Class I-IV.

For retinal degeneration, diagnosis can utilize tests which examine the fundus of the eye and/or evaluate the visual field. These include electroretinogram, fluorangiography, and visual examination. The fundus of the eye examination aims to evaluate the condition of the retina and to evaluate for the presence of the characteristic pigment spots on the retinal surface. Examination of the visual field makes possible to evaluate the sensitivity of the various parts of the retina to light stimuli. An electroretinogram (ERG) can be used, which records the electrical activity of the retina in response to particular light stimuli and allows distinct valuations of the functionality of the two different types of photoreceptors (i.e. cone cells and rod cells).

Following administration, the subject can be evaluated for response using any methods known in the art. These include, but are not limited to, ophthalmoscopy, perimetry, gonioscopy, pachymetry, or nerve fiber analysis. In some embodiments, retinal ganglion cell number and/or viability can be assessed. One of skill in the art can readily determine that the disclosed methods are effective. For example, it can be determined by whether the cup-to-disc ratio has stabilized. Scanning laser polarimetry or optical coherence tomography could be used, for example to perform retinal nerve fiber layer analysis. A visual field test could be used to monitor progression of glaucoma. For any of the disclosed methods, therapeutic efficacy in treating a vision deficiency can as an alteration in the individual's vision.

Measures of therapeutic efficacy will be applicable to the particular disease being modified and will recognize the appropriate detection methods to use to measure therapeutic efficacy. For example, therapeutic efficacy can be observed by fundus photography or evaluation of the ERG response. The method can include comparing test results after administration of the subject composition to test results before administration of the subject composition. As another example, therapeutic efficacy in treating a progressive cone dysfunction may be observed as a reduction in the rate of progression of cone dysfunction, as a cessation in the progression of cone dysfunction, or as an improvement in cone function, effects which may be observed by, such as ERG and/or cERG; color vision tests; functional adaptive optics; and/or visual acuity tests, for example, by comparing test results after administration of the subject composition to test results before administration of the subject composition and detecting a change in cone viability and/or function. As another example, therapeutic efficacy in treating a vision deficiency can as an alteration in the individual's vision, such as in the perception of red wavelengths, in the perception of green wavelengths, in the perception of blue wavelengths, effects which may be observed by, cERG and color vision tests, for example, by comparing test results after administration of the subject composition to test results before administration of the subject composition and detecting a change in cone and rod viability and/or function. In some embodiments, the method includes evaluation morphology and structure preservation and/or ERG.

Provided herein are pharmaceutical compositions that include a nucleic acid molecule including a retinal specific promoter, such as a CRX promoter, operably linked to a nucleic acid molecule encoding a CRX protein. In some embodiments, the nucleic acid molecule including a retinal specific promoter operably linked to a nucleic acid molecule encoding a CRX protein is provided in a viral vector, such as, but not limited to, an AAV vector. Suitable promoters, nucleic acid molecules encoding CRX protein, and vectors are disclosed above. The pharmaceutical compositions can be formulated and administered in a variety of ways depending on the type of disease to be treated (see, e.g., U.S. Published Application No. 2005/0054567, which discloses pharmaceutical compositions as well as administration of such compositions and is incorporated herein by reference). The pharmaceutical compositions can include a nanoparticle or dendrimer. These pharmaceutical compositions are of use in the methods disclosed herein.

Pharmaceutical compositions are provided that are formulated for local delivery to the eye. The disclosure includes within its scope pharmaceutical compositions comprising nucleic acid molecule including a retinal specific promoter operably linked to a nucleic acid molecule encoding a CRX protein. The pharmaceutical composition can include a viral vector including a nucleic acid molecule including a retinal specific promoter, such as a CRX promoter as disclosed herein, operably linked to a nucleic acid molecule encoding a CRX protein, for example an AAV vector.

The nucleic acid molecule including a retinal specific promoter operably linked to a nucleic acid molecule encoding a CRX protein can be administered ex vivo (such as into a stem cell to be implanted into the eye) or in vivo intraocularly to the subject, such as, but not limited to, sub-retinal or intravitreal administration. Generally, it is desirable to prepare the compositions as pharmaceutical compositions appropriate for the intended application. Accordingly, methods for making a medicament or pharmaceutical composition containing the nucleic acid molecules, or vectors described above, are included herein. Typically, preparation of a pharmaceutical composition (medicament) entails preparing a pharmaceutical composition that is essentially free of pyrogens, as well as any other impurities that could be harmful to humans or animals. Typically, the pharmaceutical composition contains appropriate salts and buffers to render the components of the composition stable and allow for uptake of nucleic acids or virus by target cells.

Therapeutic compositions can be formulated for injection, such as for intravitreal of subretinal administration. Such compositions are formulated generally by mixing a disclosed therapeutic agent at the desired degree of purity in a unit dosage injectable form (solution, suspension, or emulsion) with a pharmaceutically acceptable carrier, for example, one that is non-toxic to recipients at the dosages and concentrations employed and is compatible with other ingredients of the formulation. Pharmaceutical compositions can include an effective amount of the nucleic acid molecule dispersed (for example, dissolved or suspended) in a pharmaceutically acceptable carrier or excipient. Pharmaceutically acceptable carriers and/or pharmaceutically acceptable excipients are known in the art and are described, for example, in Remington's Pharmaceutical Sciences by E. W. Martin, Mack Publishing Co., Easton, PA, 19th Edition (1995). The nature of the carrier will depend on the particular mode of administration being employed. For example, formulations usually contain injectable fluids that include pharmaceutically and physiologically acceptable fluids, such as water, physiological saline, balanced salt solutions, aqueous dextrose, glycerol, or the like, as a vehicle. In addition, pharmaceutical compositions to be administered can contain minor amounts of non-toxic auxiliary substances, such as wetting or emulsifying agents, preservatives, pH buffering agents and the like, for example, sodium acetate or sorbitan monolaurate. A disclosed therapeutic agent can be suspended in an aqueous carrier, for example, in an isotonic or hypotonic buffer solution at a pH of about 3.0 to about 8.5, such as about 4.0 to about 8.0, about 6.5 to about 8.5, or about 7.4. Useful buffers include saline-buffered phosphate or an ionic boric acid buffer. The active ingredient, optionally together with excipients, can also be in the form of a lyophilisate and can be made into a solution prior to administration by the addition of suitable solvents.

The pharmaceutically acceptable carriers include any and all solvents, dispersion media, coatings, isotonic and absorption delaying agents, and the like. The use of such media and agents for pharmaceutically active substances is well-known in the art. Except insofar as any conventional media or agent is incompatible with the active ingredient, its use in the pharmaceutical compositions is contemplated. Supplementary active ingredients also can be incorporated into the compositions. For example, certain pharmaceutical compositions can include the vectors or viruses in water, mixed with a suitable surfactant, such as hydroxy-propylcellulose. Dispersions also can be prepared in glycerol, liquid polyethylene glycols, and mixtures thereof as well as in oils. Under ordinary conditions of storage and use, these preparations contain a preservative to prevent the growth of microorganisms. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles.

In some embodiments, the excipients confer a protective effect to a virus including the nucleic acid molecules, such as AAV virion, such that loss of AAV virions, as well as transduceability resulting from formulation procedures, packaging, storage, transport, and the like, is minimized. These excipient compositions are therefore considered "virion-stabilizing" in the sense that they provide higher AAV virion titers and higher transduceability levels than their non-protected counterparts, as measured using standard assays, see, for example, Published U.S.

Application No. 2012/0219528, incorporated herein by reference. These compositions therefore demonstrate "enhanced transduceability levels" as compared to compositions lacking the particular excipients described herein and are therefore more stable than their non-protected counterparts. Exemplary excipients that can used to protect the AAV virion from activity degradative conditions include, but are not limited to, detergents, proteins, e.g., ovalbumin and bovine serum albumin, amino acids, e.g., glycine, polyhydric and dihydric alcohols, such as but not limited to polyethylene glycols (PEG) of varying molecular weights, such as PEG-200, PEG-400, PEG-600, PEG-1000, PEG-1450, PEG-3350, PEG-6000, PEG-8000 and any molecular weights in between these values, with molecular weights of 1500 to 6000 preferred, propylene glycols (PG), sugar alcohols, such as a carbohydrate, preferably, sorbitol. The detergent, when present, can be an anionic, a cationic, a zwitterionic or a nonionic detergent. An exemplary detergent is a nonionic detergent. One suitable type of nonionic detergent is a sorbitan ester, e.g., polyoxyethylenesorbitan monolaurate (TWEEN®-20) polyoxyethylenesorbitan monopalmitate (TWEEN®-40), polyoxyethylenesorbitan monostearate (TWEEN®-60), polyoxyethylenesorbitan tristearate (TWEEN®-65), polyoxyethylenesorbitan monooleate (TWEEN®-80), polyoxyethylenesorbitan trioleate (TWEEN®-85), such as TWEEN®-20 and/or TWEEN®-80. These excipients are commercially available from a number of vendors, such as Sigma, St. Louis, Mo.

The amount of the various excipients in any of the disclosed compositions including AAV varies and is readily determined by one of skill in the art. For example, a protein excipient, such as BSA, if present, will can be present at a concentration of between 1.0 weight (wt.) % to about 20 wt. %, preferably 10 wt. %. If an amino acid such as glycine is used in the formulations, it can be present at a concentration of about 1 wt. % to about 5 wt. %. A carbohydrate, such as sorbitol, if present, can be present at a concentration of about 0.1 wt % to about 10 wt. %, such as between about 0.5 wt. % to about 15 wt. %, or about 1 wt. % to about 5 wt. %. If polyethylene glycol is present, it can generally be present on the order of about 2 wt. % to about 40 wt. %, such as about 10 wt. % top about 25 wt. %. If propylene glycol is used in the subject formulations, it will typically be present at a concentration of about 2 wt. % to about 60 wt. %, such as about 5 wt. % to about 30 wt. %. If a detergent such as a sorbitan ester (TWEEN®) is present, it can be present at a concentration of about 0.05 wt. % to about 5 wt. %, such as between about 0.1 wt. % and about 1 wt %, see U.S. Published Patent Application No. 2012/0219528, which is incorporated herein by reference. In one example, an aqueous virion-stabilizing formulation comprises a carbohydrate, such as sorbitol, at a concentration of between 0.1 wt. % to about 10 wt. %, such as between about 1 wt. % to about 5 wt. %, and a detergent, such as a sorbitan ester (TWEEN®) at a concentration of between about 0.05 wt. % and about 5 wt. %, such as between about 0.1 wt. % and about 1 wt. %. Virions are generally present in the composition in an amount sufficient to provide a therapeutic effect when given in one or more doses, as defined above.

The pharmaceutical compositions that include a nucleic acid molecule including a retinal specific promoter operably linked to a nucleic acid molecule encoding a CRX protein, such as a viral vector, will, in some embodiments, be formulated in unit dosage form, suitable for individual administration of precise dosages. The amount of active compound(s) administered will depend on the subject being treated, the severity of the affliction, and the manner of administration and is best left to the judgment of the prescribing clinician. Within these bounds, the formulation to be administered will contain a quantity of the active component(s) in amounts effective to achieve the desired effect in the subject being treated.

The nucleic acid molecule including a retinal specific promoter operably linked to a nucleic acid molecule encoding a CRX protein, such as a viral vector, can be included in an inert matrix for either topical application or injection into the eye. As one example of an inert matrix, liposomes may be prepared from dipalmitoyl phosphatidylcholine (DPPC), such as egg phosphatidylcholine (PC). Liposomes, including cationic and anionic liposomes, can be made using standard procedures as known to one skilled in the art. For some applications, liposomes that include a nucleic acid molecule including a retinal specific promoter operably linked to a nucleic acid molecule encoding a CRX protein can be injected intraocularly. In a formulation for intraocular injection, the liposome capsule degrades due to cellular digestion. Without being bound by theory, these formulations provide the advantages of a slow-release drug delivery system, exposing a subject to a substantially constant concentration nucleic acid molecule including a retinal specific promoter operably linked to a nucleic acid molecule encoding a CRX protein, such as in a viral vector, over time. In one example, the nucleic acid molecule including a retinal specific promoter operably linked to a nucleic acid molecule encoding a CRX protein, such as in a viral vector, can be dissolved in an organic solvent, such as DMSO or alcohol, as previously described, and contain a polyanhydride, poly(glycolic) acid, poly(lactic) acid, or polycaprolactone polymer.

The nucleic acid molecule, such as in a viral vector, for example, an AAV vector, may be formulated to permit release over a specific period of time. A release system can include a matrix of a biodegradable material or a material which releases the incorporated components by diffusion. The components can be homogeneously or heterogeneously distributed within the release system. A variety of release systems may be useful, however, the choice of the appropriate system will depend upon rate of release required by a particular application. Both non-degradable and degradable release systems can be used. Suitable release systems include polymers and polymeric matrices, non-polymeric matrices, or inorganic and organic excipients and diluents such as, but not limited to, calcium carbonate and sugar (for example, trehalose). Release systems may be natural or synthetic. However, synthetic release systems are preferred because generally they are more reliable, more reproducible and produce more defined release profiles. The release system material can be selected so that components having different molecular weights are released by diffusion through or degradation of the material.

Representative synthetic, biodegradable polymers include, for example: polyamides such as poly(amino acids) and poly(peptides); polyesters such as poly(lactic acid), poly(glycolic acid), poly(lactic-co-glycolic acid), and poly (caprolactone); poly(anhydrides); polyorthoesters; polycarbonates; and chemical derivatives thereof (substitutions, additions of chemical groups, for example, alkyl, alkylene, hydroxylations, oxidations, and other modifications routinely made by those skilled in the art), copolymers and mixtures thereof. Representative synthetic, non-degradable polymers include, for example: polyethers such as poly (ethylene oxide), poly(ethylene glycol), and poly(tetramethylene oxide); vinyl polymers-polyacrylates and polymethacrylates such as methyl, ethyl, other alkyl, hydroxyethyl methacrylate, acrylic and methacrylic acids, and others such as poly(vinyl alcohol), poly(vinyl pyrolidone), and poly (vinyl acetate); poly(urethanes); cellulose and its derivatives such as alkyl, hydroxyalkyl, ethers, esters, nitrocellulose, and various cellulose acetates; polysiloxanes; and any chemical derivatives thereof (substitutions, additions of chemical groups, for example, alkyl, alkylene, hydroxylations, oxidations, and other modifications routinely made by those skilled in the art), copolymers and mixtures thereof.

Poly(lactide-co-glycolide) microsphere can also be used for intraocular injection. Typically the microspheres are composed of a polymer of lactic acid and glycolic acid, which are structured to form hollow spheres. The spheres can be approximately 15-30 microns in diameter and can be loaded with components described herein.

The nucleic acid molecule including a retinal specific promoter operably linked to a nucleic acid molecule encoding a CRX protein, such as in a viral vector, can be included in a delivery system that can be implanted at various sites in the eye, depending on the size, shape, and formulation of the implant as well as the type of transplant procedure. The nucleic acid molecule including a retinal specific promoter operably linked to a nucleic acid molecule encoding a CRX protein can be used alone. However, in another embodiment, at least one additional agent, such as at least one agent that is disclosed below, can be included along with the nucleic acid molecule including a retinal specific promoter operably linked to a nucleic acid molecule encoding a CRX protein in the implant. The implant is then introduced into the eye. Suitable sites include but are not limited to the anterior chamber, anterior segment, posterior chamber, posterior segment, and vitreous cavity.

The implants can be inserted into the eye by a variety of methods, including placement by forceps or by trocar following making an incision in the sclera (for example, a 2-3 mm incision) or another suitable site. In some cases, the implant can be placed by trocar without making a separate incision, but instead by forming a hole directly into the eye with the trocar. The method of placement can influence the release kinetics. For example, implanting the device into the vitreous or the posterior chamber with a trocar may result in placement of the device deeper within the vitreous than placement by forceps, which may result in the implant being closer to the edge of the vitreous. The location of the implanted device may influence the concentration gradients of the nucleic acid molecule including a retinal specific promoter operably linked to a nucleic acid molecule encoding a CRX protein, such as in a viral vector, surrounding the device and, thus, influence the release rates (for example, a device placed closer to the edge of the vitreous may result in a slower release rate, see U.S. Pat. Nos. 5,869,079 and 6,699,493).

The use of implants in the eye is well-known in the art (see U.S. Pat. Nos. 6,699,493 and 5,869,079). In one embodiment, an implant is formulated with the nucleic acid molecule including a retinal specific promoter operably linked to a nucleic acid molecule encoding a CRX protein associated with a bio-erodible polymer matrix. Other delivery methods can also be used, such as nanoparticles.

Generally, when implants are used, the nucleic acid molecule including a retinal specific promoter operably linked to a nucleic acid molecule encoding a CRX protein is homogeneously distributed through the polymeric matrix, such that it is distributed evenly enough that no detrimental fluctuations in rate of release occur due to uneven distribution in the polymer matrix. The selection of the polymeric composition to be employed varies with the desired release kinetics, the location of the implant, patient tolerance, and the nature of the implant procedure. The polymer can be included as at least about 10 weight percent of the implant. In one example, the polymer is included as at least about 20 weight percent of the implant. In another embodiment, the implant comprises more than one polymer. These factors are described in detail in U.S. Pat. No. 6,699,493. Characteristics of the polymers generally include biodegradability at the site of implantation, compatibility with the agent of interest, ease of encapsulation, and water insolubility, amongst others. Generally, the polymeric matrix is not fully degraded until the drug load has been released. The chemical composition of suitable polymers is known in the art (for example, see U.S. Pat. No. 6,699,493). The nucleic acid molecule including a retinal specific promoter operably linked to a nucleic acid molecule encoding a CRX protein, as disclosed herein, can be formulated in an implantable form with other carriers and solvents. For example, buffering agents and preservatives can be employed. The implant sizes and shape can also be varied for use in particular regions of the eye (see U.S. Pat. No. 5,869,079). In some embodiments, a nanoparticle or dendrimer is used.

Local modes of administration include, by way of example, intraocular, intraorbital, intravitreal and subretinal routes. In an embodiment, significantly smaller amounts of the components (compared with systemic approaches) may exert an effect when administered locally (for example, intravitreally) compared to when administered systemically (for example, intravenously). Local modes of administration can reduce or eliminate the incidence of potential side effects. In one embodiment, components described herein are delivered subretinally, e.g., by subretinal injection. Subretinal injections may be made directly into the macular, e.g., submacular injection. Exemplary methods include intraocular injection (e.g., retrobulbar, subretinal, submacular, intravitreal and intrachoroidal), iontophoresis, eye drops, and intraocular implantation (e.g., intravitreal, sub-Tenons and sub-conjunctival). In one embodiment, a composition as disclosed herein is delivered by intravitreal injection. Intravitreal injection has a relatively low risk of retinal detachment. Methods for administration of agents to the eye are known in the medical arts and can be used to administer components described herein.

Administration may be provided as a single administration, a periodic bolus (for example, subretinally or intravitreally) or as continuous infusion from an internal reservoir (for example, from an implant disposed at an intra- or extra-ocular location (see, U.S. Pat. Nos. 5,443,505 and 5,766,242)) or from an external reservoir (for example, from an intravenous bag). Intravitreal injection or subretinal injection of a therapeutic agents can be performed once, or can be performed repeatedly, such as 1, 2, 3, 4, 5, 6, 7, 8, 9, or 10 times. Administration can be performed biweekly, weekly, every other week, monthly, or every 2, 3, 4, 5, or 6 months.

Individual doses are typically not less than an amount required to produce a measurable effect on the subject and may be determined based on the pharmacokinetics and pharmacology of the subject composition or its by-products, and thus based on the disposition of the composition within the subject. This includes consideration of the route of administration as well as dosage amount, which can be adjusted for subretinal (applied directly to where action is desired for mainly a local effect), intravitreal (applied to the vitreous for a pan-retinal effect) applications. Effective amounts of dose and/or dose regimen can readily be determined empirically from preclinical assays, from safety and escalation and dose range trials, individual clinician-patient relationships, as well as in vitro and in vivo assays.

Nucleic acid molecules can be delivered by microinjection, electroporation, lipid-mediated transfection, peptide-mediated delivery, nanoparticle mediated deliver, dendrimer mediated delivery, or other methods known in the art. An appropriate dose depends on the subject being treated (e.g., human or nonhuman primate or other mammal), age and general condition of the subject to be treated, the severity of the condition being treated, the mode of administration of the vector/virion, among other factors. An appropriate effective amount can be readily determined by one of skill in the art. Thus, a "therapeutically effective amount" will fall in a relatively broad range that can be determined through clinical trials.

Components can be administered by continuous release for a particular period from a sustained release drug delivery device immobilized to an inner wall of the eye or via targeted transscleral controlled release into the choroid (see, for example, PCT Application No. PCT/US00/00207, PCT/US02/14279, Ambati et al. (2000) Invest. Ophthalmol. Vis. Sci. 41:1181-1185, and Ambati et al. (2000) Invest. Ophthalmol. Vis. Sci. 41:1186-1191). A variety of devices suitable for administering components locally to the inside of the eye are known in the art. See, for example, U.S. Pat. Nos. 6,251,090; 6,299,895; 6,416,777, and 6,413,540

In some embodiments, for in vivo injection, i.e., injection directly to the subject, a therapeutically effective dose will be on the order of from about $10^5$ to $10^{16}$ of the AAV virions, such as $10^8$ to $10^{14}$ AAV virions. The dose, of course, depends on the efficiency of transduction, promoter strength, the stability of the message and the protein encoded thereby, and clinical factors. Effective dosages can be readily established by one of ordinary skill in the art through routine trials establishing dose response curves.

In some embodiments, if the nucleic acid molecule is included in an AAV vector, an effective amount to achieve a change will be about $1\times10^8$ vector genomes or more, in some cases about $1\times10^9$, about $1\times10^{10}$, about $1\times10^{11}$, about $1\times10^{12}$, or about $1\times10^{13}$ vector genomes or more, in certain instances, about $1\times10^{14}$ vector genomes or more, and usually no more than about $1\times10^{15}$ vector genomes. In some embodiments, the amount of vector that is delivered is about $1\times10^{14}$ vectors or less, for example about $1\times10^{13}$, about $1\times10^{12}$, about $1\times10^{11}$, about $1\times10^{10}$, or about $1\times10^9$ vectors or less, in certain instances about $1\times10^8$ vectors, and typically no less than $1\times10^8$ vectors. In some non-limiting examples, the amount of vector genomes that is delivered is about $1\times10^{10}$ to about $1\times10^{11}$ vectors. In additional non-limiting examples, the amount of vector that is delivered is about $1\times10^{10}$ to about $1\times10^{12}$ vector genomes.

In some embodiments, the amount of pharmaceutical composition to be administered may be measured using multiplicity of infection (MOI). In some embodiments, MOI refers to the ratio, or multiple of vector or viral genomes to the cells to which the nucleic may be delivered. In some embodiments, the MOI may be about $1\times10^6$. In some cases, the MOI can be about $1\times10^5$ to about $1\times10^7$. In some cases, the MOI may be about $1\times10^4$ to about $1\times10^8$. In some cases, recombinant viruses of the disclosure are at least about $1\times10^1$, about $1\times10^2$, about $1\times10^3$, about $1\times10^4$, about $1\times10^5$, about $1\times10^6$, about $1\times10^7$, about $1\times10^8$, about $1\times10^9$, about $1\times10^{10}$, about $1\times10^{11}$, about $1\times10^{12}$, about $1\times10^{13}$, about $1\times10^{14}$, about $1\times10^{15}$, about $1\times10^{16}$, about $1\times10^{17}$, and about $1\times10^{18}$ MOI. In some cases, recombinant viruses of this disclosure are about $1\times10^{8}$ to $1\times10^{14}$ MOI.

In some the amount of pharmaceutical composition delivered comprises about $1\times10^{8}$ to about $1\times10^{15}$ particles of recombinant viruses, about $1\times10^{9}$ to about $1\times10^{14}$ particles of recombinant viruses, about $1\times10^{10}$ to about $1\times10^{13}$ particles of recombinant viruses, or about $1\times10^{11}$ to about 1x10.s12 particles of recombinant viruses (see U.S. Published Patent Application No. 2015/0259395, incorporated herein by reference).

Dosage treatment may be a single dose schedule or a multiple dose schedule to ultimately deliver the amount specified above. Moreover, the subject may be administered as many doses as appropriate. Thus, the subject may be given, e.g., $10^{5}$ to $10^{16}$ AAV virions in a single dose, or two, four, five, six or more doses that collectively result in delivery of, e.g., $10^{5}$ to $10^{16}$ AAV virions. One of skill in the art can readily determine an appropriate number of doses to administer.

In some embodiments, an AAV is administered at a dose of about $1\times10^{11}$ to about $1\times10^{14}$ viral particles (vp)/kg. In some examples, the AAV is administered at a dose of about $1\times10^{12}$ to about $8\times10^{13}$ vp/kg. In other examples, the AAV is administered at a dose of about $1\times10^{13}$ to about $6\times10^{13}$ vp/kg. In specific non-limiting examples, the AAV is administered at a dose of at least about $1\times10^{11}$, at least about $5\times10^{11}$, at least about $1\times10^{12}$, at least about $5\times10^{12}$, at least about $1\times10^{13}$, at least about $5\times10^{13}$, or at least about $1\times10^{14}$ vp/kg. In other non-limiting examples, the rAAV is administered at a dose of no more than about $5\times10^{11}$, no more than about $1\times10^{12}$, no more than about $5\times10^{12}$, no more than about $1\times10^{13}$, no more than about $5\times10^{13}$, or no more than about $1\times10^{14}$ vp/kg. In one non-limiting example, the AAV is administered at a dose of about $1\times10^{12}$ vp/kg. The AAV can be administered in a single dose, or in multiple doses (such as 2, 3, 4, 5, 6, 7, 8, 9 or 10 doses) as needed for the desired therapeutic results.

A general method for intravitreal injection may be illustrated by the following brief outline. This example is merely meant to illustrate certain features of the method, and is in no way meant to be limiting. Procedures for intravitreal injection are known in the art (see, for example Peyman, et al. (2009) Retina 29 (7): 875-912 and Fagan and Al-Qureshi, (2013) Clin. Experiment. Ophthalmol. 41 (5): 500-7). Other methods of intraocular administration are known in the art and include subretinal administration.

Briefly, a subject for intravitreal injection may be prepared for the procedure by pupillary dilation, sterilization of the eye, and administration of anesthetic. Any suitable mydriatic agent known in the art may be used for pupillary dilation. Adequate pupillary dilation may be confirmed before treatment. Sterilization may be achieved by applying a sterilizing eye treatment, e.g., an iodide-containing solution such as povidone-iodine (BETADINE®). A similar solution may also be used to clean the eyelid, eyelashes, and any other nearby tissues (e.g., skin). Any suitable anesthetic may be used, such as lidocaine or proparacaine, at any suitable concentration. Anesthetic may be administered by any method known in the art, including without limitation topical drops, gels or jellies, and subconjunctival application of anesthetic.

Prior to injection, a sterilized eyelid speculum may be used to clear the eyelashes from the area. The site of the injection may be marked with a syringe. The site of the injection may be chosen based on the lens of the patient. For example, the injection site may be 3-3.5 mm from the limus in pseudophakic or aphakic patients, and 3.5-4 mm from the limbus in phakic patients. The patient may look in a direction opposite the injection site. During injection, the needle can be inserted perpendicular to the sclera and pointed to the center of the eye. The needle can be inserted such that the tip ends in the vitreous, rather than the subretinal space. Any suitable volume known in the art for injection may be used. After injection, the eye can be treated with a sterilizing agent such as an antibiotic. The eye can also be rinsed to remove excess sterilizing agent.

The subject can be administered additional therapeutic agents. Additional agents that can be administered to the subject include antibacterial and antifungal antibiotics, as well as non-steroidal anti-inflammatory agents to reduce risk of infection and inflammation. Additional agents can be administered by any route. The additional agents can be formulated separately, or in the same composition.

Agents of use include antibiotics such as minoglycosides (for example, amikacin, apramycin, arbekacin, bambermycins, butirosin, dibekacin, dihydrostreptomycin, fortimicin(s), gentamicin, isepamicin, kanamycin, micronomicin, neomycin, neomycin undecylenate, netilmicin, paromomycin, ribostamycin, sisomicin, spectinomycin, streptomycin, tobramycin, trospectomycin), amphenicols (for example, azidamfenicol, chloramphenicol, florfenicol, thiamphenicol), ansamycins (for example, rifamide, rifampin, rifamycin sv, rifapentine, rifaximin), β-lactams (for example, carbacephems (e.g., loracarbef), carbapenems (for example, biapenem, imipenem, meropenem, panipenem), cephalosporins (for example, cefaclor, cefadroxil, cefamandole, cefatrizine, cefazedone, cefazolin, cefcapene pivoxil, cefclidin, cefdinir, cefditoren, cefepime, cefetamet, cefixime, cefmenoxime, cefodizime, cefonicid, cefoperazone, ceforanide, cefotaxime, cefotiam, cefozopran, cefpimizole, cefpiramide, cefpirome, cefpodoxime proxetil, cefprozil, cefroxadine, cefsulodin, ceftazidime, cefteram, ceftezole, ceftibuten, ceftizoxime, ceftriaxone, cefuroxime, cefuzonam, cephacetrile sodium, cephalexin, cephaloglycin, cephaloridine, cephalosporin, cephalothin, cephapirin sodium, cephradine, pivcefalexin), cephamycins (for example, cefbuperazone, cefmetazole, cefininox, cefotetan, cefoxitin), monobactams (for example, aztreonam, carumonam, tigemonam), oxacephems, flomoxef, moxalactam), penicillins (for example, amdinocillin, amdinocillin pivoxil, amoxicillin, ampicillin, apalcillin, aspoxicillin, azidocillin, azlocillin, bacampicillin, benzylpenicillinic acid, benzylpenicillin sodium, carbenicillin, carindacillin, clometocillin, cloxacillin, cyclacillin, dicloxacillin, epicillin, fenbenicillin, floxacillin, hetacillin, lenampicillin, metampicillin, methicillin sodium, mezlocillin, nafcillin sodium, oxacillin, penamecillin, penethamate hydriodide, penicillin G benethamine, penicillin g benzathine, penicillin g benzhydrylamine, penicillin G calcium, penicillin G hydrabamine, penicillin G potassium, penicillin G procaine, penicillin N, penicillin O, penicillin V, penicillin V benzathine, penicillin V hydrabamine, penimepicycline, phenethicillin potassium, piperacillin, pivampicillin, propicillin, quinacillin, sulbenicillin, sultamicillin, talampicillin, temocillin, ticarcillin), other (for example, ritipenem), lincosamides (for example, clindamycin, lincomycin), macrolides (for example, azithromycin, carbomycin, clarithromycin, dirithromycin, erythromycin, erythromycin acistrate, erythromycin estolate, erythromycin glucoheptonate, erythromycin lactobionate, erythromycin propionate, erythromycin stearate, josamycin, leucomycins, midecamycins, miokamycin, oleandomycin, primycin, rokitamycin, rosaramicin, roxithromycin, spiramycin, troleandomycin), polypeptides (for example, amphomycin, bacitracin, capreomycin, colistin, enduracidin, enviomycin, fusafungine, gramicidin s, gramicidin(s), mikamycin, polymyxin, pristinamycin, ristocetin, teicoplanin, thiostrepton, tuberactinomycin, tyrocidine, tyrothricin, vancomycin, viomycin, virginiamycin, zinc bacitracin), tetracyclines (for example, apicycline, chlortetracycline, clomocycline, demeclocycline, doxycycline, guamecycline, lymecycline, meclocycline, methacycline, minocycline, oxytetracycline, penimepicycline, pipacycline, rolitetracycline, sancycline, tetracycline), and others (e.g., cycloserine, mupirocin, tuberin). Agents of use also include synthetic antibacterials, such as 2,4-Diaminopyrimidines (for example, brodimoprim, tetroxoprim, trimethoprim), nitrofurans (for example, furaltadone, furazolium chloride, nifuradene, nifuratel, nifurfoline, nifurpirinol, nifurprazine, nifurtoinol, nitrofurantoin), quinolones and analogs (for example, cinoxacin, ciprofloxacin, clinafloxacin, difloxacin, enoxacin, fleroxacin, flumequine, grepafloxacin, lomefloxacin, miloxacin, nadifloxacin, nalidixic acid, norfloxacin, ofloxacin, oxolinic acid, pazufloxacin, pefloxacin, pipemidic acid, piromidic acid, rosoxacin, rufloxacin, sparfloxacin, temafloxacin, tosufloxacin, trovafloxacin), sulfonamides (for example, acetyl sulfamethoxypyrazine, benzylsulfamide, chloramine-b, chloramine-t, dichloramine t, mafenide, 4'-(methylsulfamoyl) sulfanilanilide, noprylsulfamide, phthalylsulfacetamide, phthalylsulfathiazole, salazosulfadimidine, succinylsulfathiazole, sulfabenzamide, sulfacetamide, sulfachlorpyridazine, sulfachrysoidine, sulfacytine, sulfadiazine, sulfadicramide, sulfadimethoxine, sulfadoxine, sulfaethidole, sulfaguanidine, sulfaguanol, sulfalene, sulfaloxic acid, sulfamerazine, sulfameter, sulfamethazine, sulfamethizole, sulfamethomidine, sulfamethoxazole, sulfamethoxypyridazine, sulfametrole, sulfamidocchrysoidine, sulfamoxole, sulfanilamide, sulfanilylurea, n-sulfanilyl-3,4-xylamide, sulfanitran, sulfaperine, sulfaphenazole, sulfaproxyline, sulfapyrazine, sulfapyridine, sulfasomizole, sulfasymazine, sulfathiazole, sulfathiourea, sulfatolamide, sulfisomidine, sulfisoxazole) sulfones (for example, acedapsone, acediasulfone, acetosulfone sodium, dapsone, diathymosulfone, glucosulfone sodium, solasulfone, succisulfone, sulfanilic acid, p-sulfanilylbenzylamine, sulfoxone sodium, thiazolsulfone), and others (for example, clofoctol, hexedine, methenamine, methenamine anhydromethylene-citrate, methenamine hippurate, methenamine mandelate, methenamine sulfosalicylate, nitroxoline, taurolidine, xibornol).

Additional agents of use include antifungal antibiotics such as polyenes (for example, amphotericin B, candicidin, dennostatin, filipin, fungichromin, hachimycin, hamycin, lucensomycin, mepartricin, natamycin, nystatin, pecilocin, perimycin), others (for example, azaserine, griseofulvin, oligomycins, neomycin undecylenate, pyrrolnitrin, siccanin, tubercidin, viridin) allylamines (for example, butenafine, naftifine, terbinafine), imidazoles (for example, bifonazole, butoconazole, chlordantoin, chlormiidazole, cloconazole, clotrimazole, econazole, enilconazole, fenticonazole, flutrimazole, isoconazole, ketoconazole, lanoconazole, miconazole, omoconazole, oxiconazole nitrate, sertaconazole, sulconazole, tioconazole), thiocarbamates (for example, tolciclate, tolindate, tolnaftate), triazoles (for example, fluconazole, itraconazole, saperconazole, terconazole) others (for example, acrisorcin, amorolfine, biphenamine, bromosalicylchloranilide, buclosamide, calcium propionate, chlorphenesin, ciclopirox, cloxyquin, coparaffinate, diamthazole dihydrochloride, exalamide, flucytosine, halethazole, hexetidine, loflucarban, nifuratel, potassium iodide, propionic acid, pyrithione, salicylanilide, sodium propionate, sulbentine, tenonitrozole, triacetin, ujothion, undecylenic acid, zinc propionate). Antineoplastic agents can also be of use including (1) antibiotics and analogs (for example, aclacinomycins, actinomycin, anthramycin, azaserine, bleomycins, cactinomycin, carubicin, carzinophilin, chromomycins, dactinomycin, daunorubicin, 6-diazo-5-oxo-L-norleucine, doxorubicin, epirubicin, idarubicin, menogaril, mitomycins, mycophenolic acid, nogalamycin, olivomycines, peplomycin, pirarubicin, plicamycin, porfiromycin, puromycin, streptonigrin, streptozocin, tubercidin, zinostatin, zorubicin), (2) antimetabolites such as folic acid analogs (for example, denopterin, edatrexate, methotrexate, piritrexim, pteropterin, trimetrexate), (3) purine analogs (for example, cladribine, fludarabine, 6-mercaptopurine, thiamiprine, thioguanine), (4) pyrimidine analogs (for example, ancitabine, azacitidine, 6-azauridine, carmofur, cytarabine, doxifluridine, emitefur, enocitabine, floxuridine, fluorouracil, gemcitabine, tagafur).

Steroidal anti-inflammatory agents can also be used such as 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, cyclosporine, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, and triamcinolone hexacetonide.

In addition, non-steroidal anti-inflammatory agents can be used. These include aminoarylcarboxylic acid derivatives (for example, enfenamic acid, etofenamate, flufenamic acid, isonixin, meclofenamic acid, mefenamic acid, niflumic acid, talniflumate, terofenamate, tolfenamic acid), arylacetic acid derivatives (for example, aceclofenac, acemetacin, alclofenac, amfenac, amtolmetin guacil, bromfenac, bufexamac, cinmetacin, clopirac, diclofenac sodium, etodolac, felbinac, fenclozic acid, fentiazac, glucametacin, ibufenac, indomethacin, isofezolac, isoxepac, lonazolac, metiazinic acid, mofezolac, oxametacine, pirazolac, proglumetacin, sulindac, tiaramide, tolmetin, tropesin, zomepirac), arylbutyric acid derivatives (for example, bumadizon, butibufen, fenbufen, xenbucin), arylcarboxylic acids (for example, clidanac, ketorolac, tinoridine), arylpropionic acid derivatives (for example, alminoprofen, benoxaprofen, bermoprofen, bucloxic acid, carprofen, fenoprofen, flunoxaprofen, flurbiprofen, ibuprofen, ibuproxam, indoprofen, ketoprofen, loxoprofen, naproxen, oxaprozin, piketoprolen, pirprofen, pranoprofen, protizinic acid, suprofen, tiaprofenic acid, ximoprofen, zaltoprofen), pyrazoles (for example, difenamizole, epirizole), pyrazolones (for example, apazone, benzpiperylon, feprazone, mofebutazone, morazone, oxyphenbutazone, phenylbutazone, pipebuzone, propyphenazone, ramifenazone, suxibuzone, thiazolinobutazone), salicylic acid derivatives (for example, acetaminosalol, aspirin, benorylate, bromosaligenin, calcium acetylsalicylate, diflunisal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamide o-acetic acid, salicylsulfuric acid, salsalate, sulfasalazine), thiazinecarboxamides (for example, ampiroxicam, droxicam, isoxicam, lornoxicam, piroxicam, tenoxicam), .epsilon.-acetamidocaproic acid, s-adenosylmethionine, 3-amino-4-hydroxybutyric acid, amixetrine, bendazac, benzydamine, .alpha.-bisabolol, bucolome, difenpiramide, ditazol, emorfazone, fepradinol, guaiazulene, nabumetone, nimesulide, oxaceprol, paranyline, perisoxal, proquazone, superoxide dismutase, tenidap, and zileuton.

The disclosure is illustrated by the following non-limiting Examples.

EXAMPLES

A particularly challenging area for retinal gene therapy is the treatment of autosomal dominant mutations. Up to 30% of retinitis pigmentosa cases might be caused by autosomal dominant mutations. Most frequently detected are mutations in Rhodopsin gene (RHO) with common P23H and P347S mutations. Approaches aiming to target solely the mutant allele (Lewin et al., *Nat Med,* 4, 967-971; Tessitore et al., *Molecular therapy: the journal of the American Society of Gene Therapy,* 14, 692-699) or both (Chadderton et al., *Molecular therapy: the journal of the American Society of Gene Therapy,* 17, 593-599; O'Reilly et al., *American journal of human genetics,* 81, 127-135) alleles have been developed but show major limitations. Specificity and efficiency are significant challenges for pathogenic allele-specific approaches for dominant Rhodopsin mutations, where providing high expression of this rod structural protein would be necessary in the suppression and replacement strategies.

The study presented below provides the first direct proof-of-concept for treatment of dominant CRX-LCA by providing high expression of the normal gene and without the removal of the dominant mutant allele.

Example 1

Methods

Cell Culture:

IPSCs maintenance and retinal differentiation. IPSCs were maintained in E8 medium on Matrigel-coated plates. Non-enzymatic passaging using EDTA was performed. For differentiation cells were lifted using EDTA and transferred to ultra-low attachment dishes to form embryoid bodies. Differentiation was performed as previously described (Zhong et al., *Nat Commun,* 5, 4047; Kaya et al., *Molecular vision,* 25, 663-678) with minor modifications, namely supplementation with 20 ng/ml IGF-1 following dissection of optic domains and use of 9-cis retinaldehyde instead of all-trans retinoic acid from day 90.

Retinal Organoid Differentiation Protocol:

List of media used for retinal differentiation and their composition is presented below:

1:1 Neural Induction Medium (1:1 NIM)

| Component | Amount for 500 ml | Amount for 250 ml | Amount for 50 ml |
|---|---|---|---|
| DMEM/F12 (1:1) with glutamax | 490 ml | 245 ml | 49 ml |
| 1% N2 supplement (Invitrogen) | 5 ml | 2.5 ml | 0.5 ml |
| 1x Non-essential amino acids (NEAAs) | 5 ml | 2.5 ml | 0.5 ml |
| 2 μg/ml Heparin (Sigma) | 50 μl of 20 mg/ml stock | 25 μl of 20 mg/ml stock | 5 μl of 20 mg/ml stock |

3:1 Neural-Induction Medium (3:1 NIM)

| Component | Amount for 500 ml | Amount for 250 ml | Amount for 50 ml |
|---|---|---|---|
| DMEM | 358.5 ml | 179.25 ml | 35.85 ml |
| F12 | 119.5 ml | 59.75 ml | 11.95 ml |
| 2% B27 (minus vitamin A) | 10 ml | 5 ml | 1 ml |
| 2 mM Glutamax | 5 ml | 2.5 ml | 0.5 ml |
| 1x Minimum essential media-non essential amino acids (NEAAs) | 5 ml | 2.5 ml | 0.5 ml |
| 1% Antibiotic-antimycotic | 5 ml | 2.5 ml | 0.5 ml |

Soluble Factors:

ROCK inhibitor (Y-27632 dihydrochloride, Tocris) stock 10 mM, final concentration 10 μM, dilution 1:1000.

Taurine (Sigma-Aldrich) stock 100 mM, final concentration 100 μM, dilution 1:1000.

9-cis retinaldehyde (Sigma-Aldrich) stock solution 1 mM, final 1 μM or 500 nM, dilution 1:1000 or 1:2000

IGF-1 (Gibco) stock 10 μg/ml, final 20 ng/ml, dilution 1:500

Differentiation Protocol:

| Day | Procedure |
|---|---|
| 0 | Detach the iPSCs by EDTA solution, dissociate into small clumps by pipetting a few times.<br>Culture in suspension with E8 with Rock inhibitor (final concentration: 10 μM) in ultra-low attachment dish (6 ml in 60 mm 9 ml in 100 mm). |
| 1 | Add 3 ml of 1:1 NIM - ratio E8 to NIM 3:1 |
| 2 | Add 6 ml of 1:1 NIM - ratio E8 to NIM 1:1 |
| 3 | Collect the EBs to a 14 ml tube and aspirate the supernatant.<br>Suspend EBs in 100% 1:1 NIM (around 10 ml per dish). |
| 6 | Prepare Matrigel-coated dishes for day 7. |
| 7 | Seed the aggregates (average size of 0.22 ± 0.05 mm) onto Matrigel-coated dishes containing 1:1 NIM at an approximate density of 20 aggregates per $cm^2$. |
| 7-16 | Change the medium every 2-3 days. |
| 16 | Switch the medium to 3:1 NIM. Change medium every 2-3 days. |
| 16-35 | Change the medium every 2-3 days. |

-continued

| Day | Procedure |
|---|---|
| 28-35 | Detach horseshoe-shaped NR domains manually with a sharpened Tungsten needle under inverted microscope. Collect the NR domains and culture in 3:1 NIM with IGF-1 in a ultra-low attachment U bottom 96-well plate. |
| 35-42 | Change the medium every 2-3 days. |
| 42 | Supplement the medium with 10% fetal bovine serum (Gibco), 100 μM Taurine (Sigma) and IGF-1. |
| 42-63 | Change the medium every 2-3 days. |
| 63-91 | Use 3:1 NIM with 10% FBS, IGF-1, 100 μM Tau and 1 μM 9cis retinal. Change every 2-3 days. |
| 91 onwards | Lower the concentration of 9cis retinal to 0.5 μM. Replace every 2-3 days. |

Immunohistochemistry and Microscopy:

Retinal organoids were collected using wide-bore pipette tips, washed with PBS then fixed with 4% PFA (Neuro Technologies) for at least 1 hr. Organoids were then washed 3× with PBS and transferred into 15% sucrose (w/v) solution until they sank into the bottom of the tube. Then the tissue was transferred into 30% sucrose solution (w/v). Following these dehydration steps the organoids were placed in M1 embedding matrix and snap frozen in an ethanol/dry ice bath. Blocks were cryosectioned at 18 μm onto SUPERFROST PLUS™ (Fisher Scientific) glass slides. A Thermo Scientific MICROM HM550 cryostat (Thermo Fisher Scientific). Sectioned were dried before storage at −20° C. For staining slides were rehydrated in PBS for 15 min, and then blocked in 5% donkey serum, 1% BSA (Sigma-Aldrich), 0.1% TRITON® X-100 (Sigma-Aldrich) solution in PBS for at least 1 hr. Both primary and secondary antibodies were added in 1% BSA (Sigma-Aldrich), 0.1% TRITON® X-100 (Sigma-Aldrich) solution in PBS. Sections were incubated with primary antibodies overnight. Slides were washes with PBS 5× before secondary antibodies were added for 2 hr. Slides were washed 3× with PBS then incubated with DAPI before addition of Fluoromount-G mounting medium (SouthernBiotech) and covering with a microscopy cover glass (VWR). Samples were imaged on Zeiss 700 confocal microscope (Zeiss) or Leica SP-8 confocal microscope (Leica Microsystems). Images were processed with ZEN BLACK™, ZEN BLUE™

(Zeiss), LAS X (Leica Microsystems) and ImageJ software. Quantifications and fluorescence intensity measurements were performed using ImageJ software. At least three sections from three independent organoids were used for quantification.

List of Primary Antibodies Used:

| Antigen | Species/type | Dilution | Source | Identifier |
|---|---|---|---|---|
| CRX | Mouse monoclonal | 1:100 | Abnova | H00001406-M02 |
| CTBP2 | Mouse monoclonal | 1:200 | BD Transduction Laboratories | 612044 |
| GFP | Goat polyclonal | 1:200 | Rockland | 600-101-215 |
| L/M Opsin | Rabbit polyclonal | 1:250 | Millipore | AB5405 |
| OCT4 | Rabbit polyclonal | 1:500 | Abcam | ab19857 |
| OTX1/2 | Rabbit polyclonal | 1:200 | Abcam | ab21990 |
| Peripherin2 | Chicken polyclonal | 1:200 | Tiansen Li | n.a. |
| Recoverin | Rabbit polyclonal | 1:500 | Chemicon International | AB5585 |
| Rhodopsin | Mouse monoclonal | 1:500 | Robert Molday | 1D4 |
| S Opsin | Rabbit polyclonal | 1:250 | Millipore | AB5407 |

Preparation of AAV Vectors:

Cloning of Human CRX Promoter:

Sequences derived from human CRX 5' untranslated region (NCBI Reference Sequence: NG_008605.1) were amplified from human genomic DNA and combined to produce a promoter of 631 base pairs. Specifically, first 189 nucleotides correspond to positions 3085-3274 of the reference sequence; the next 69 correspond to 3323-3392 of the reference and the next 361 correspond to 4808-5169 of the reference sequence. Note that 4999-5169 is exon 1; therefore, this human CRX promoter element contains the 1st exon of human CRX gene.

Brief Overview of AAV Production

HEK293 cells were transfected with vector plasmid and pHLP19-AAV2 and pLAdeno5 helper plasmids using $CaCl_2$) method. Cell pellet was homogenized with a microfluidizer to release AAV particles. Cell debris were eliminated by centrifugation and free DNA removed by 1 hr of 100 U/ml bezonase treatment. AAV particles were then precipitated in 8% PEG on ice for 2 hr. AAV particles pellet was collected by centrifugation and treated with RNaseA for 30 min. at 37° C. Purification of AAV was subsequently conducted using a series of ultracentrifugation steps on CsCl density gradient and dialysis. Titration was performed by qPCR.

Detailed Protocol:

| Step | Procedures |
|---|---|
| AAV production by transient transfection | Seed HEK 293 cells in 5 roller bottles at a density of $3 \times 10^7$ cells per bottle in 300 ml DMEM medium with 10% FBS and 1% Penicilin-Streptomycin. Culture in a tissue-culture incubator at 37° C. in 5% $CO_2$.<br>When cells reach 80% confluency add 5 ml of 1M HEPES buffer for pH stabilization. Prepare transfection solution by mixing 150 μg of vector transgene plasmid, 150 μg of pHLP19-AAV2 capsid plasmid, 150 μg of pLAdeno5 helper plasmid with 15 ml 0.3M $CaCl_2$ and 15 ml of 2x HBSS buffer. Mix gently by pipetting. Add the transfection solution to roller bottle immediately.<br>Incubate with transfection mix 6 hours to overnight at 37° C. in 3% $CO_2$.<br>Replace medium with 100 ml of DMEM with 1% Penicilin-Streptomycin(serum-free) medium. Incubate the cells at 37° C. with 5% $CO_2$.<br>48 hours following transfection detach cells by vigorous swirling and harvest.<br>Pool cells from all 5 roller bottles into one 500 ml conical tube.<br>Centrifuge at 3000 xg for 30 min. at 4° C.<br>Discard supernatant and resuspend cell pellet in 350 ml of TSM buffer. Cell pellet can either be used immediately for purification or stored at −80° C. If stored, frozen pellet should be thawed in a water bath at 37° C. before proceeding to purification. |
| Isolation and purification of AAV | Homogenize cell pellet using a microfluidizer.<br>In order to remove cell debris centrifuge at 3000 xg for 30 min. and transfer supernatant into a fresh 500 ml centrifuge tube.<br>Add 1M $CaCl_2$ to a final concentration of 25 mM.<br>Mix well and leave to incubate for 10 min. at 4° C.<br>Centrifuge at 3000 xg for 1 h. Collect supernatant and transfer into a fresh 500 ml centrifuge tube.<br>Digest residual free DNA by treatment with Benzonase at 100 U/ml for 1 h at 37° C.<br>Precipitate AAV particles by adding 40% PEG8000/2.5N NaCl to a final concentration of 8% PEG. Thoroughly mix, incubate for 2 h on ice.<br>Centrifuge at 3000 xg for 30 min. at 4° C. Discard the supernatant.<br>Resuspend the pellet in 25 ml of HSSE-RNase A buffer. Incubate for 30 min. at 37° C.<br>Prepare CsCl step gradient ultracentrifugation by mixing 5 ml of 1.5 g/ml CsCl to the bottom of a 38.5 ml ultracentrifuge tube, then add 8 ml of 1.3 g/ml CsCl for the middle layer. Finally add vector suspension to the top. Make sure ultracentrifuge tubes are correctly balanced before proceeding to the next step.<br>Centrifuge in SW32Ti rotor for 18 h at 28,000 rpm.<br>Place the ultracentrifuge tube above a halogen beam illuminator, identify and collect viral bands with a 18G needle attached to a 5 ml syringe. Transfer into a 14 ml ultracentrifuge tube for linear gradient ultracentrifugation. Fill up the tube with 1.4 g/ml CsCl.<br>Centrifuge in SW40Ti rotor for 72 h at 38,000 rpm.<br>Place the ultracentrifuge tube above halogen beam illuminator.<br>Identify and collect viral band with a 18G needle attached to a 5 ml syringe.<br>Dialyze overnight in a Slide-A-Lyzer cassette in Tris-buffered saline.<br>Filter the virus sample using 0.22 μm fiter unit and store vector solution at −80° C. until use. |

Statistical Analysis:

GraphPad Prism version 8.0 software was used to plot data and perform statistical analysis. For two group comparisons 2-tailed, type 3 Student's t test was used. For multiple groups ANOVA analysis was used with either Dunnett's or Tukey's post hoc tests.

Example 2

Results

Figure 1B:
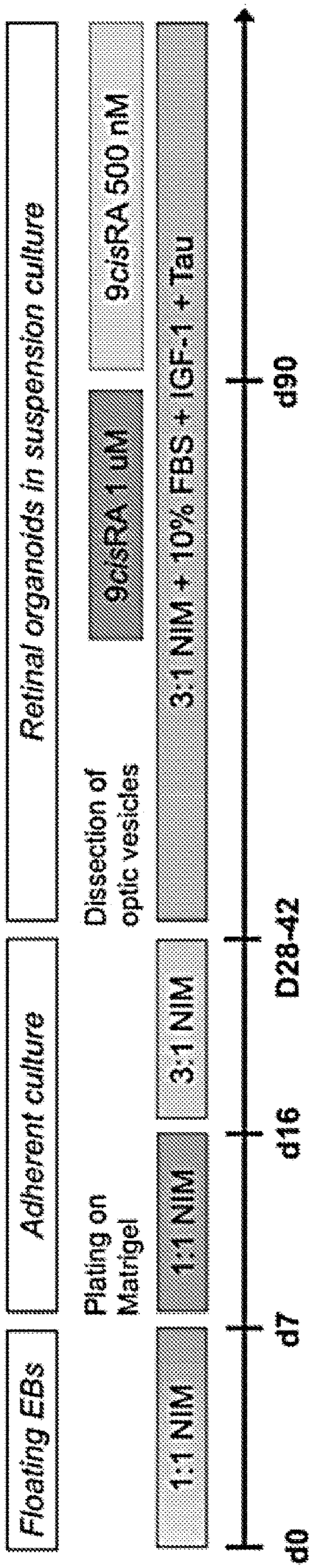

To examine disease mechanisms associated with CRX-LCA, induced pluripotent stem cells (iPSCs) were derived from a skin biopsy of a previously described pediatric LCA patient carrying in a heterozygous form a c.413delT (p.I138fs48) frameshift mutation in the CRX coding sequence (FIG. 1A) as well as unaffected familial control. iPSC lines were of normal karyotype and exhibited typical features of pluripotent stem cells. The lines were differentiated into retinal organoids using a modification of a previously published protocol (FIG. 1B). Briefly, iPSC colonies were lifted off using EDTA to form embryoid bodies (EBs). Neural induction was performed on floating EBs for 7 days, after which they were plated on Matrigel. Eye field/optic vesicle domains were manually dissected at around 4 weeks from the adherent cultures and subsequently cultured in suspension as retinal organoids. Both patient and control cell lines formed morphologically similar retinal neural epithelia.

Photoreceptors are the primary cells expressing CRX in the retina. To assess differentiation into this cell type, retinal organoids at week 9 were stained with OTX2, a marker of photoreceptor precursors upstream of CRX in photoreceptor specification pathway. The proportion of cells expressing OTX2 was equivalent in both patient and control organoids. Similarly, there was no significant difference in the proportion of CRX-expressing cells at this stage. From week 10, Recoverin+ photoreceptor precursors started accumulating at the apical aspect of the organoids. At week 13, there were 2-3 rows of Recoverin+ cells present in the prospective photoreceptor layer. Analysis of protein extracts from the organoids by immunoblotting showed presence of the truncated form of CRX in patient samples. Quantification of the protein bands indicated increased overall levels of CRX in patient samples with a significant proportion contributed by the mutant allele. Together, these observations show that early commitment to photoreceptor fate occurs in CRX-LCA and the mutant form the protein is expressed in patient-derived organoids.

Figure 1C:
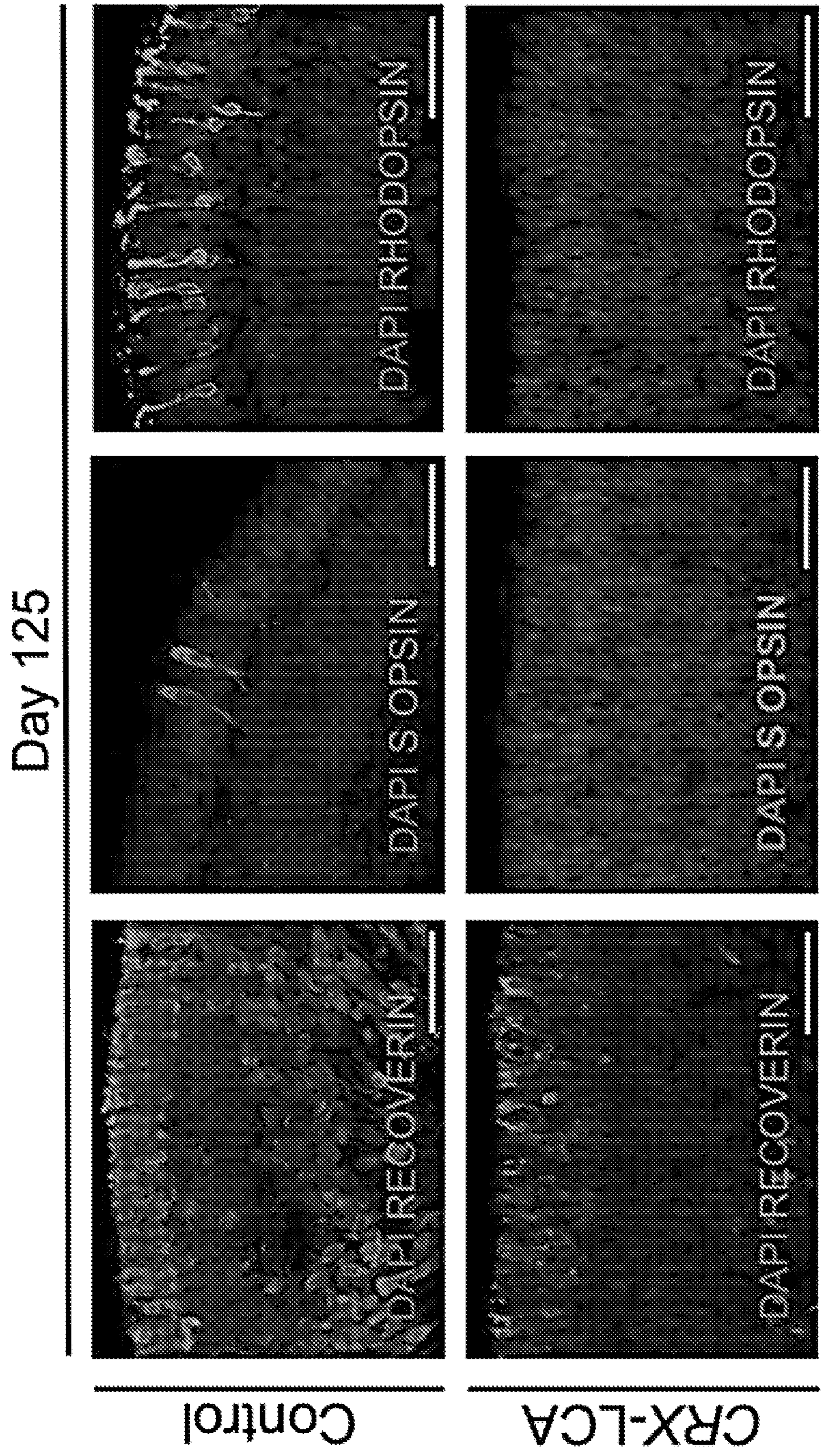
Figure 1D:
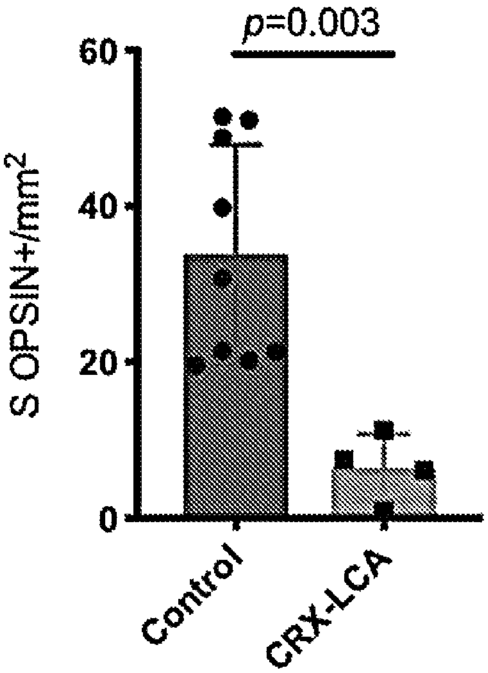
Figure 1E:
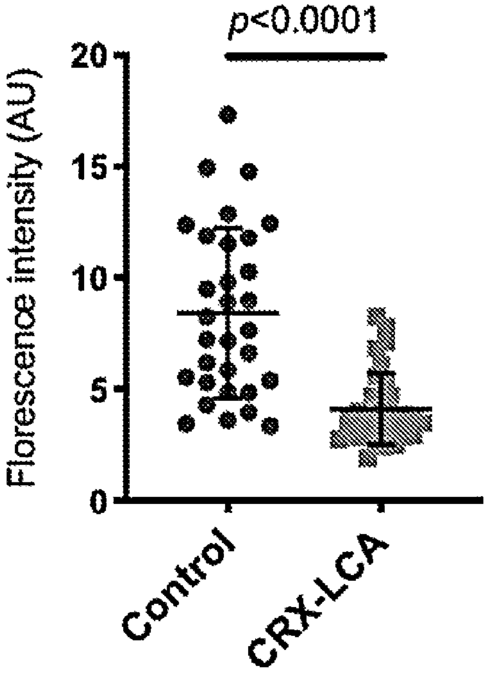
Figure 1F:
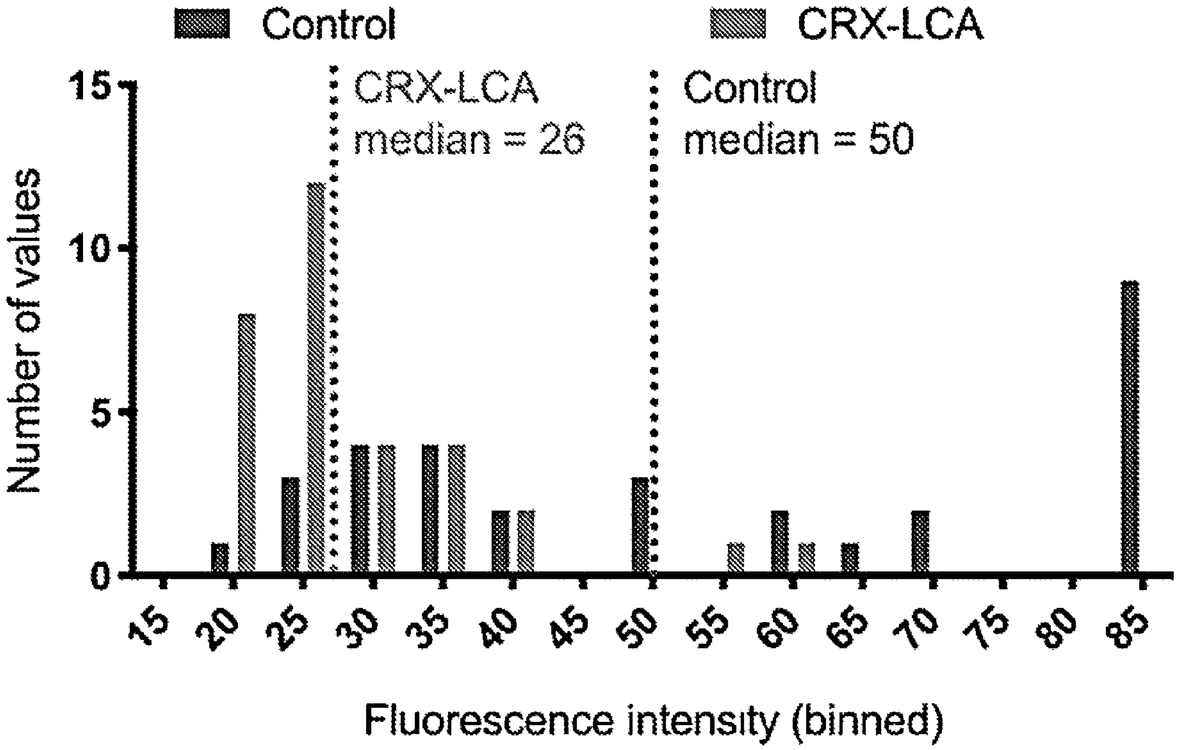
Figure 1G:
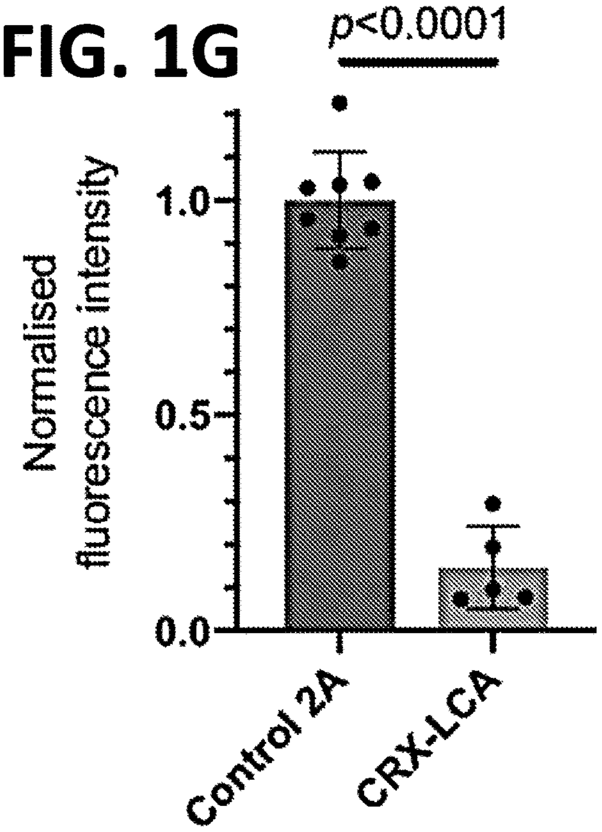
Figure 1H:
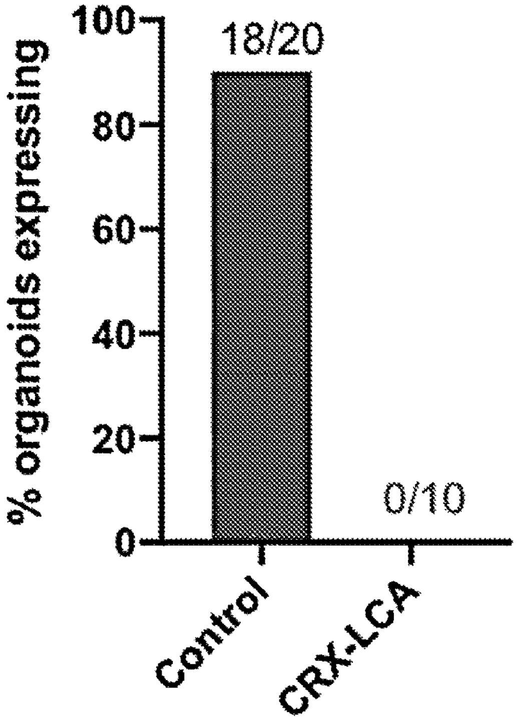
Figure 1I:
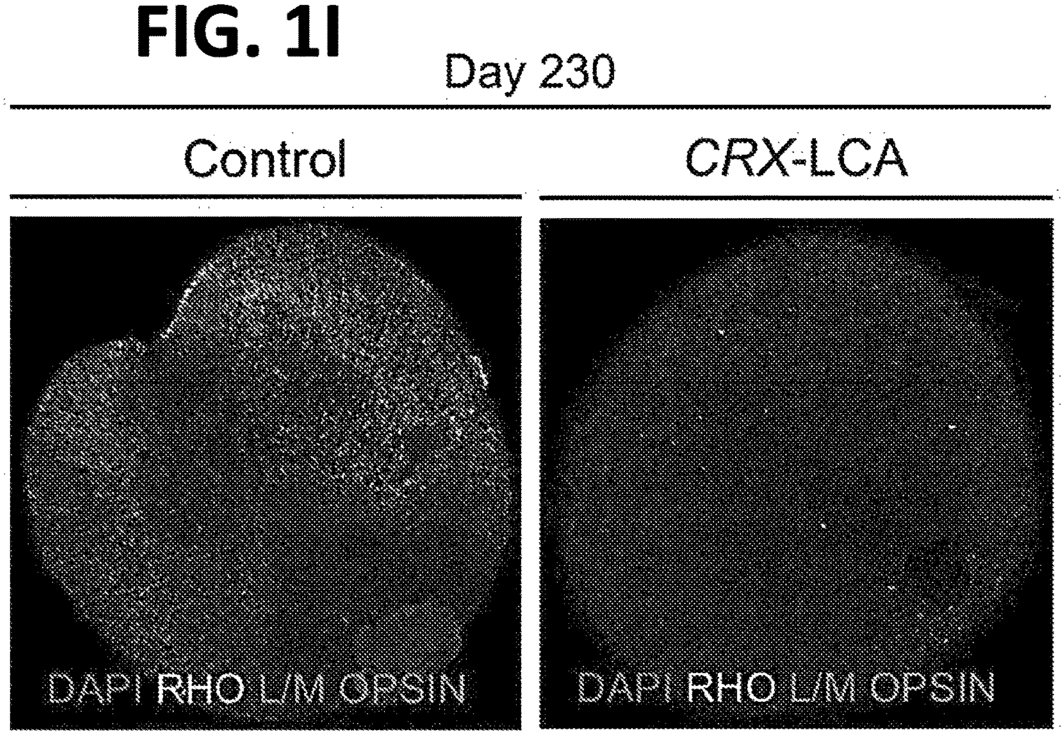
Figure 1J:
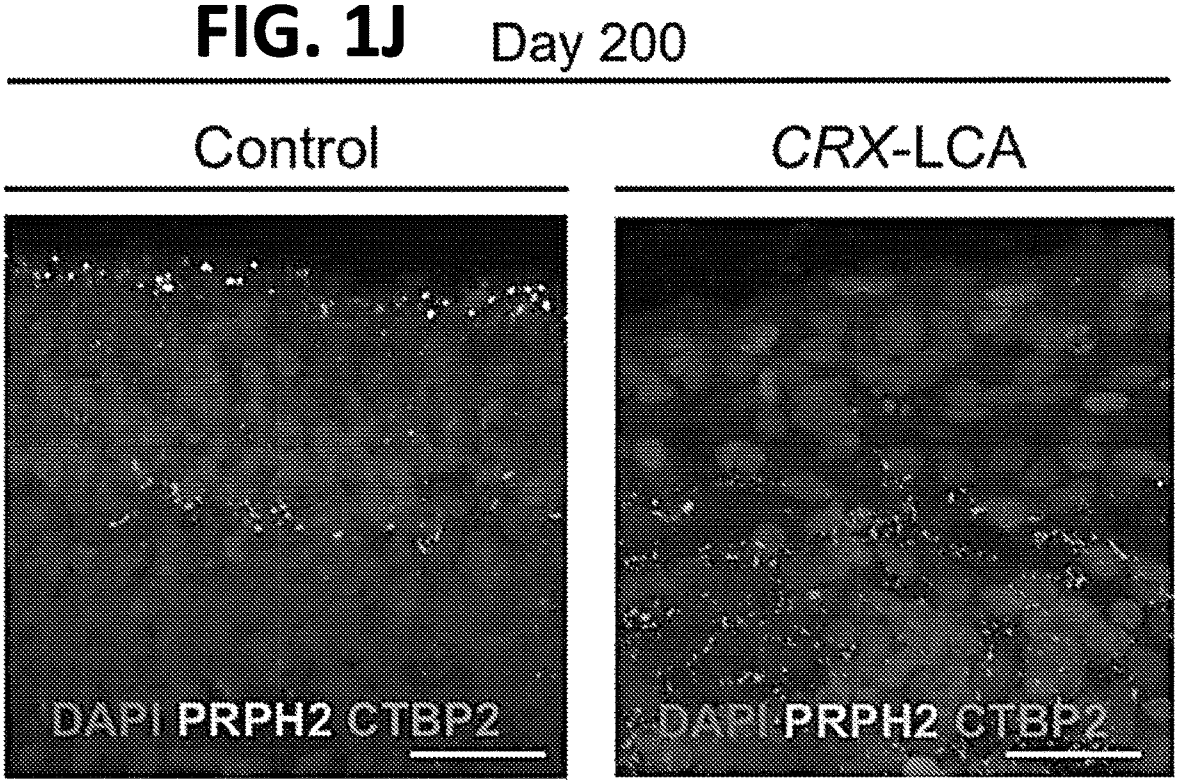
Figure 1K:
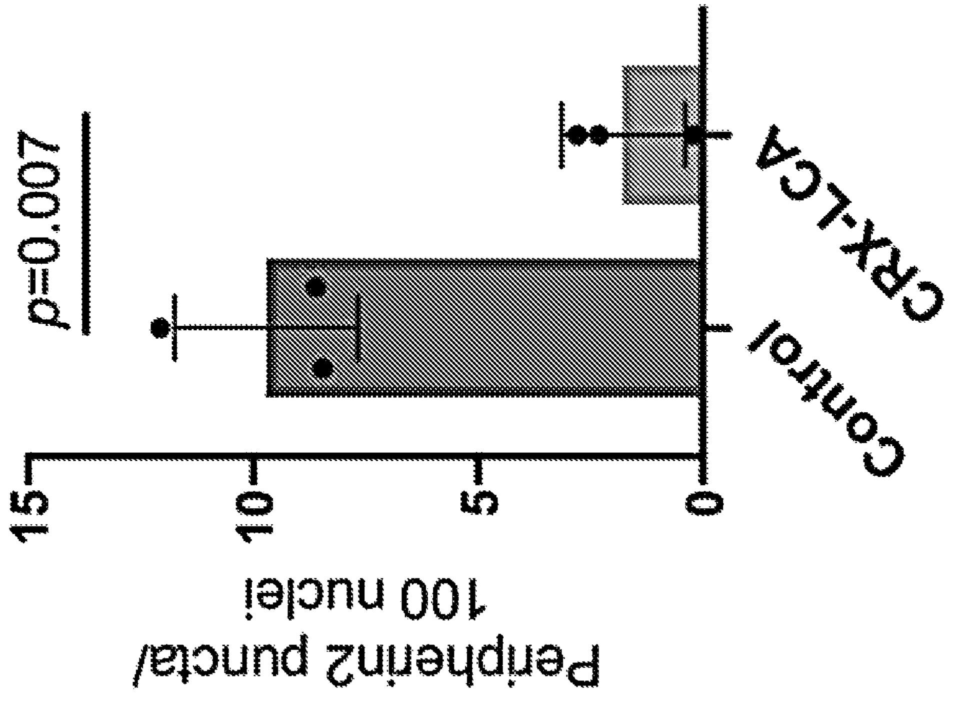
Figure 1L:
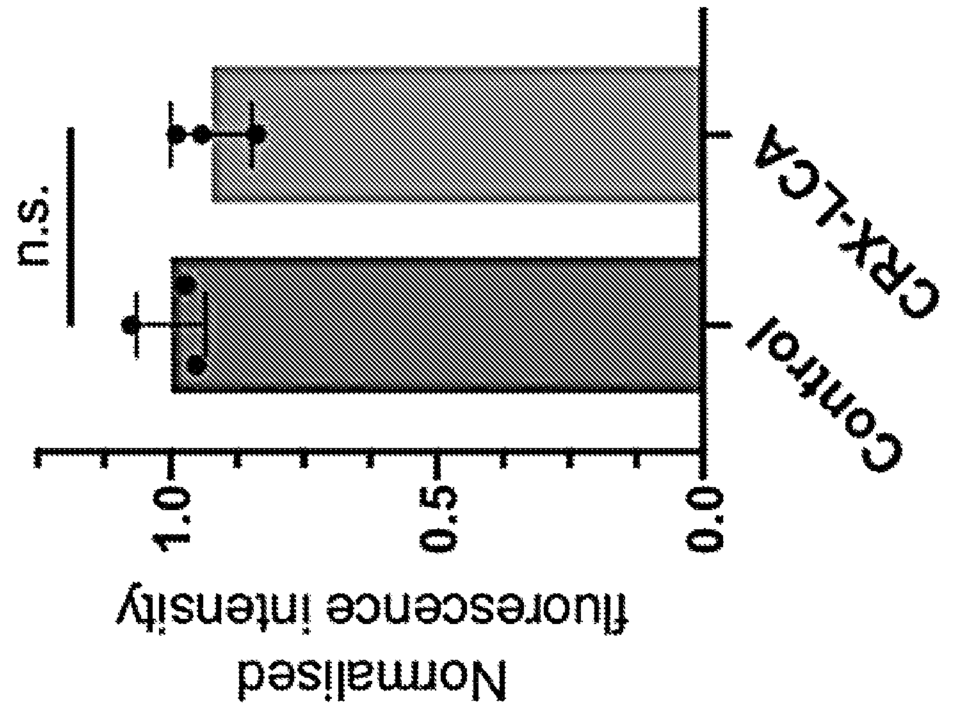

To examine onset of photoreceptor maturation, the organoids were stained at d125 for S Opsin, the first Opsin to be expressed during development. By d125 S Opsin was robustly expressed in control organoids, whereas CRX-LCA organoids showed much weaker staining (FIG. 1C). Quantification S Opsin+ cells as well as average fluorescence intensity in individual cells revealed significant reductions in patient samples in both measures (FIG. 1D, E). Additionally, plotting a histogram of maximal fluorescence intensities in individual S Opsin-expressing cone cells showed a clear shift towards lower maximum intensity values in CRX-LCA line as compared to familial control (FIG. 1F). The second Opsin expressed in retinal development is the rod cell visual pigment Rhodopsin. At d125 Rhodopsin became expressed in patches of prospective rod photoreceptors in control organoids (FIG. 1C). In contrast, CRX-LCA retinal organoids lacked robust Rhodopsin immunoreactivity measured by fluorescence intensity on organoid sections (FIG. 1G). Loss of Rhodopsin was consistent across 10 organoids examined (FIG. 1H). Qualitatively, separation of the photoreceptor layer was less advanced in patient-derived organoids (FIG. 1C). Cone cell L/M Opsin is the final Opsin to be expressed in humans. Flatmounts of retinal organoids at d230 clearly showed that L/M Opsin staining was severely reduced in patient sample and that even at this stage Rhodopsin was still absent (FIG. 1I). Opsin proteins accumulate in apical outer segment structures in photoreceptors. Staining was examined for Peripherin2, a protein involved in outer segment biogenesis. In control organoids bright puncta of Peripherin2 localized to the apical border of the tissue, whereas patient organoids showed diminished staining (FIG. 1J, K). Basally, developing photoreceptors extend axons to contact interneurons. Staining for the synaptic marker CTBP2 (Ribeye) showed similar pattern in both control and patient organoids (FIG. 1 J, L). Collectively, histological analysis of maturing retinal organoids suggest that pathological c.413delT (p.I138fs48) frameshift mutation in CRX impairs specific aspects of photoreceptor terminal differentiation.

CRX mutations lead to several types of retinopathies with varying severity (den Hollander et al., *Prog Retin Eye Res,* 27, 391-419; Hull et al., *Investigative ophthalmology & visual science,* 55, 6934-6944). Animal models indicate multiple disease mechanisms depending on the nature of the mutation (Tran et al., *PLoS Genet,* 10, e1004111; Roger et al., *J Clin Invest,* 124, 631-643). However, in human subjects, clear correlations between mutation type or its location within the gene's functional domains and phenotype severity or manifestation are not evident (Hull et al., *Investigative ophthalmology & visual science,* 55, 6934-6944). This highlights the difficulty that human genetic diversity presents for predicting disease phenotypes and challenges for use of animal models that necessarily place the mutations in a different genomic context. The use of human retinal organoids derived from patient-specific iPSCs might circumvent some of the limitations presented by animal models by much better representing the native human genomic architecture in which the pathological mutations act. Considering the range of disease manifestations in human subjects (Hull et al., *Investigative ophthalmology & visual science,* 55, 6934-6944), it also remains an open question whether a single gene therapy approach will be suitable for all the patients. A gene therapy paradigm using overexpression of the correct allele of CRX driven by elements of its own native promoter and delivered in an AAV vector was tested. Prominent rescue of Rhodopsin expression in AAV-treated CRX-LCA retinal organoids identifies this approach as a treatment strategy. Retinal organoids were used as a platform to assess gene therapy in a patient with CRX-LCA retinal dystrophy, an experimental strategy which can be applied to other autosomal dominant conditions of the retina. Patient iPSC-derived organoids have been used to provide proof-of-concept for AAV-mediated gene therapy of recessive X-linked retinitis pigmentosa caused by mutations in RP2 (Lane et al., Stem Cell Reports, 2020).

Transduction was tested with two commonly used adeno-associated viral vector (AAV) capsid serotypes AAV2 and AAV8 with CMV promoter driving a GFP reporter. AAV2 capsid showed much higher proportion of cells expressing both GFP and CRX in organoids at d150, 10 days post vector addition at d140. Human CRX promoter sequences were then tested for driving transcription in retinal cells that normally express the CRX gene.

Example 3

Cloning and Testing of the Composite CRX Promoter

Figure 2A:
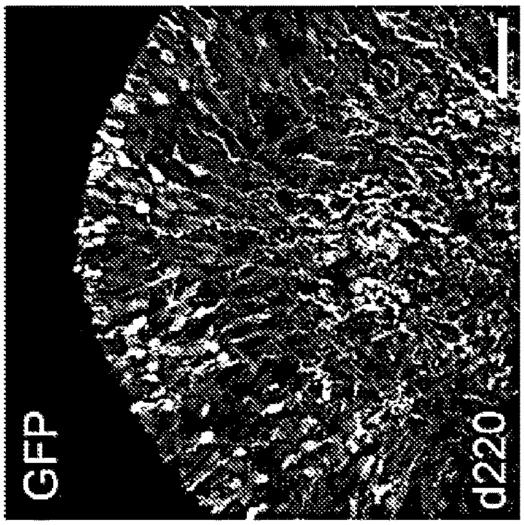
FIGS. 2A-2D. Testing human CRX promoter elements for expression in human retinal organoid tissues. (A-C) AAV vectors encoding CMV promoter (A) or 631 bp human CRX promoter element (B, C) upstream of GFP reporter were used to transduce retinal organoids at day 120. Low $5\times10^{10}$ viral genome/organoid (B) or high $10^{11}$ vg/organoid (C) doses resulted in similar transduction of outer organoid layer where photoreceptor cells are present at day 220 (D) Late stage organoid at day 220 showing widespread GFP reporter expression across the outer photoreceptor layer. Scale bar 100 μm.
Figure 2B:
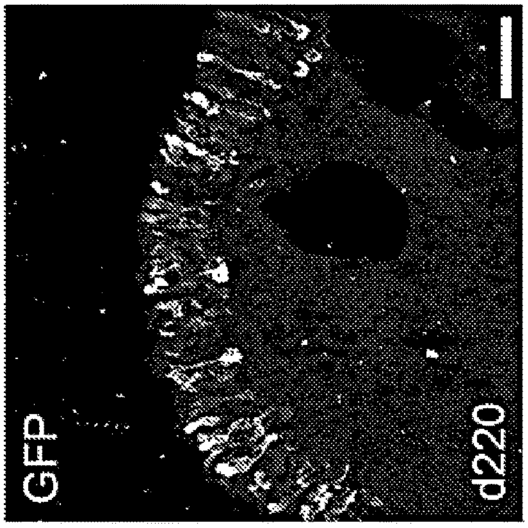
Figure 2C:
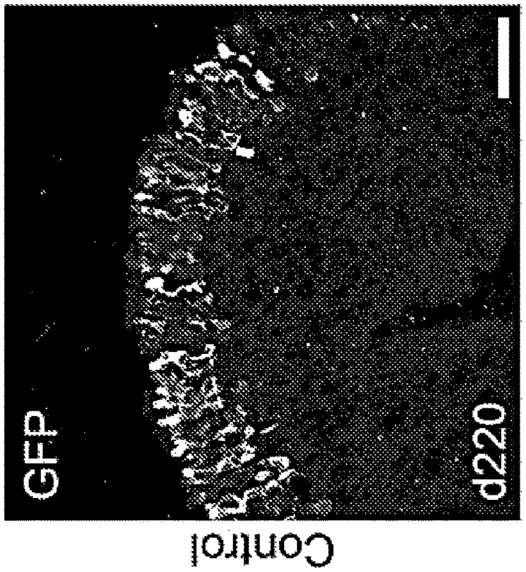
Figure 2D:
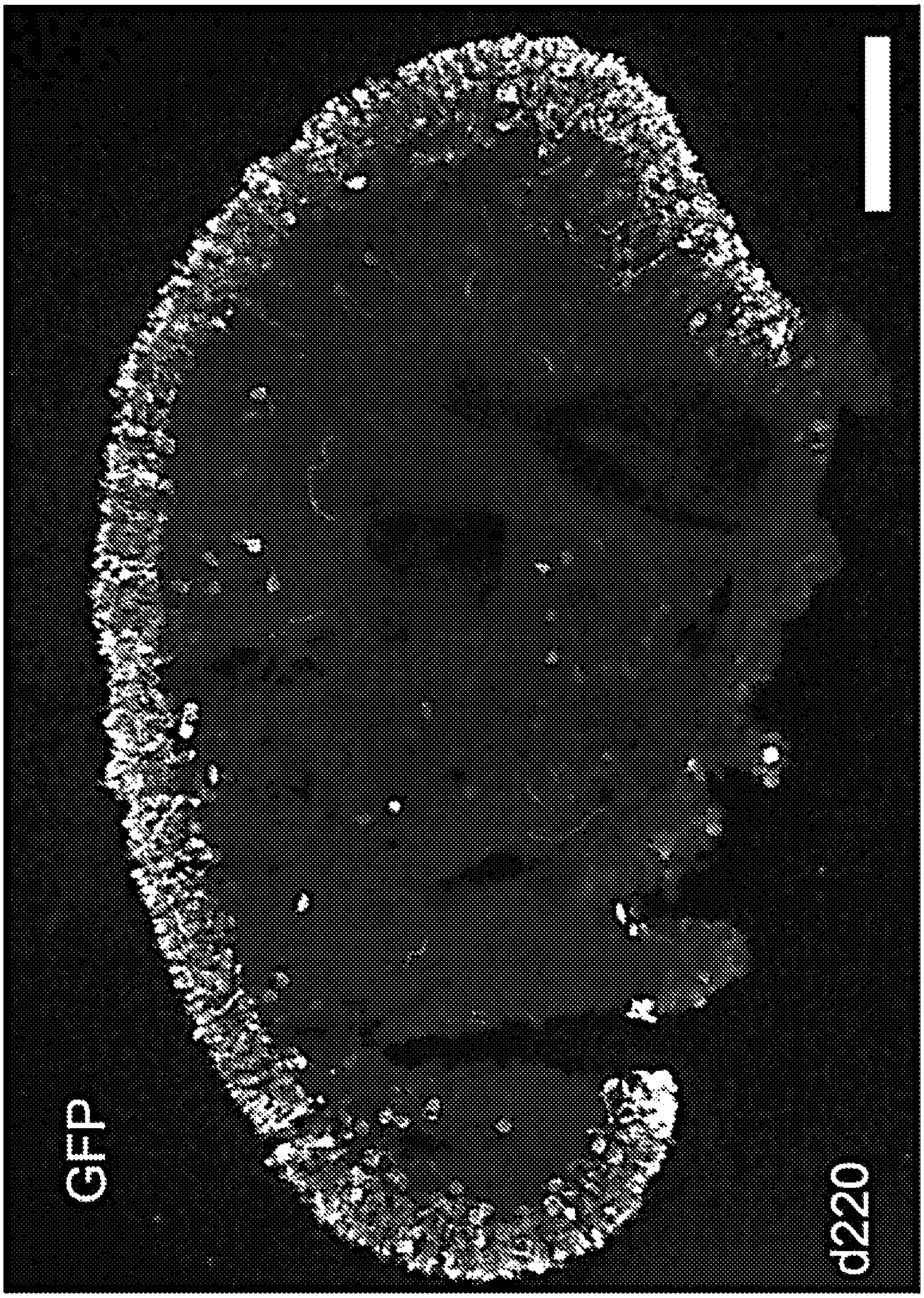

Different sequence regions derived from the upstream region of the human CRX gene (NCBI Reference Sequence: NG_008605.1) were amplified using human genomic DNA and assembled to produce a 631 base pair length promoter element. In this promoter, 189 nucleotides correspond to positions 3085-3274, 69 correspond to 3323-3392, and 361 correspond to 4808-5169 of the reference. This promoter element contains 1st exon of the human CRX gene (nucleotides 4999-5169). These sequences were included based on the binding sites of several transcription factors expressed during human retinal development. Without being bound by theory, these sites were included because of their potential relevance in regulation of CRX gene, particularly important being five sequence elements that can bind CRX or OTX2, which ensure robust expression of the downstream gene. The 631 nucleotide (nt) composite promoter was cloned upstream of a GFP reporter in an AAV vector construct. This vector was used alongside a CMV promoter vector for transduction of retinal organoids d190 of differentiation. Four weeks following vector addition (d220), the organoids were collected, cryosectioned, and stained for GFP (FIGS. 2A-2D). The reporter expression was present throughout the organoid with CMV promoter vector (FIG. 2A). In contrast, CRX composite promoter showed localization to a distinct cell layer at the apical region of the organoids, consistent with the location of photoreceptors (FIG. 2B-2D). A dose of $5\times10^{10}$ viral genomes (vg) per organoid was sufficient for significant transduction of the photoreceptor layer (FIG. 2B), and the transduction was widespread across the organoid with a dose of $10^{11}$ vg per organoid (FIG. 2D).

Example 4

Figures 3A, 3B, 3C, 3D, 3E, 3F:
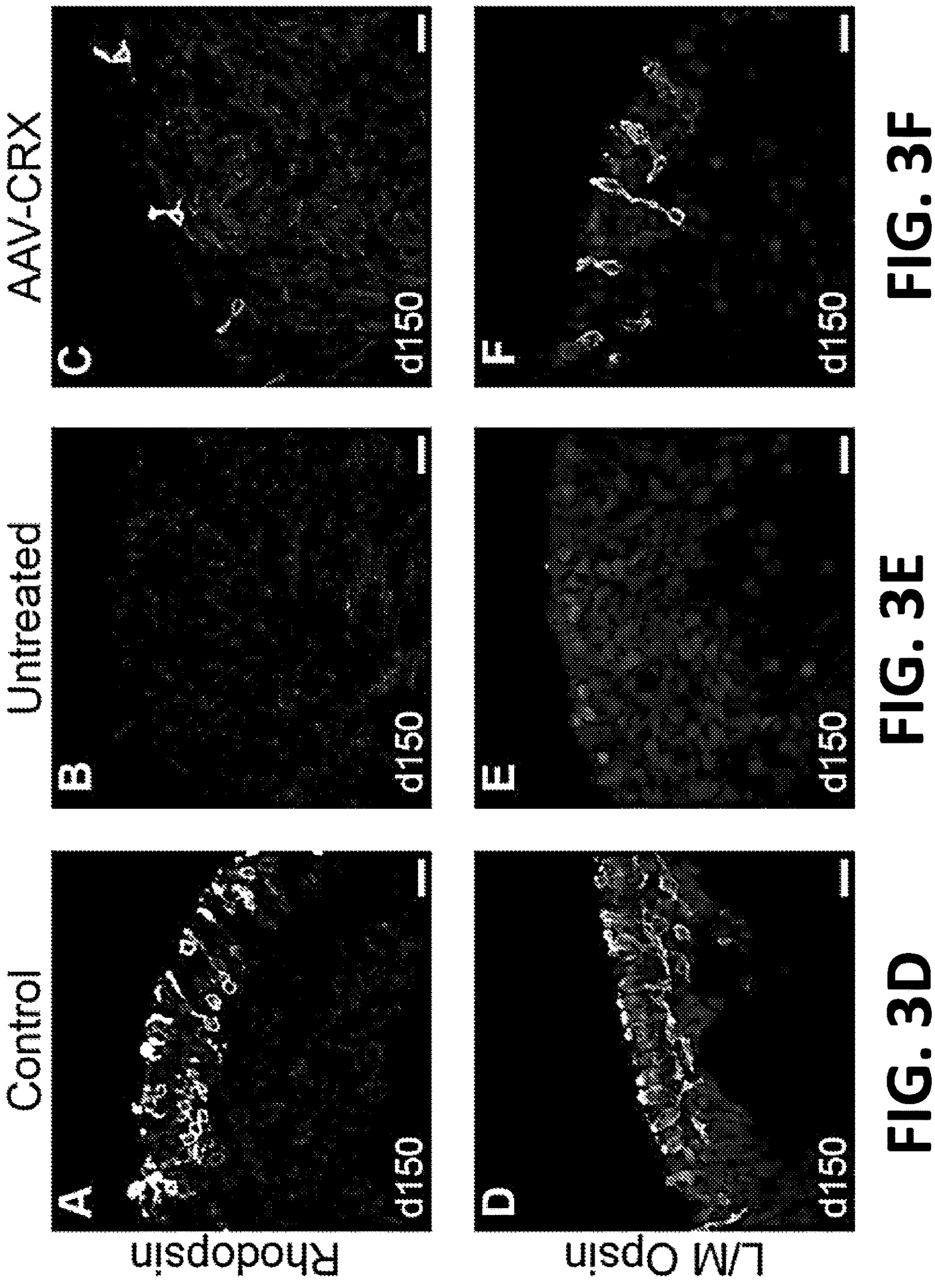
FIGS. 3A-3H. Rescue of Rhodopsin and M Opsin 4 weeks post treatment (first subject with CRX c.413delT (p.I138fs48 mutation). Retinal organoids from the frameshift CRX mutation patient c.413delT (p.I138fs48) were transduced with AAV-CRX vector at day 120 and analyzed 4 weeks later at day 150 by immunohistochemistry. Rhodopsin staining was present in control (A), but not CRX-I138fs patient samples (B). Treated organoids showed a fraction of cells with rescued expression (C). Similarly, L/M Opsin was present in control (D), absent in patient (E) and partially restored following treatment (F). Quantification of the percentage of CRX-positive cells showing immunostaining for Rhodopsin (G) or L/M Opsin (H). 3 organoids per group, Student's t-test, p values indicated.
Figure 3H:
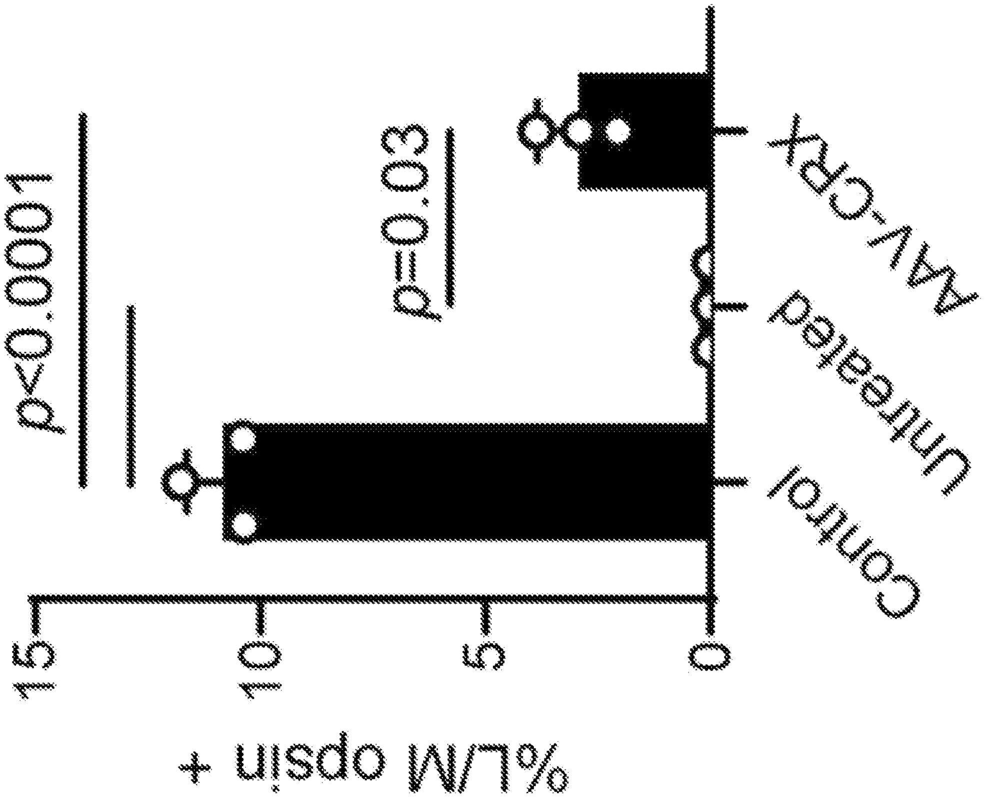
Figure 3G:
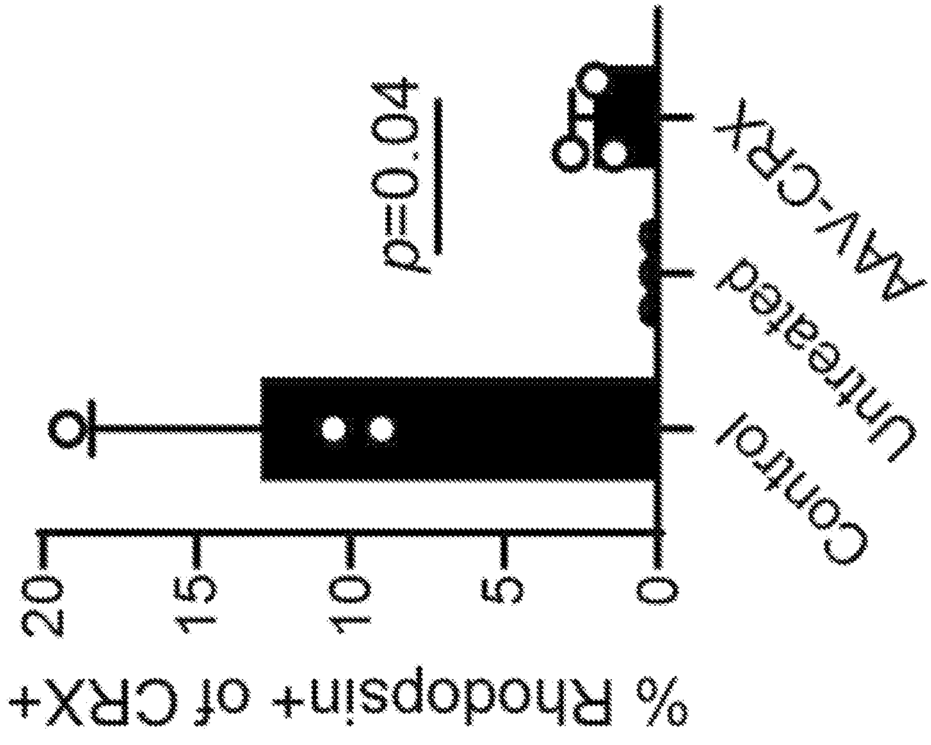
Figure 4:
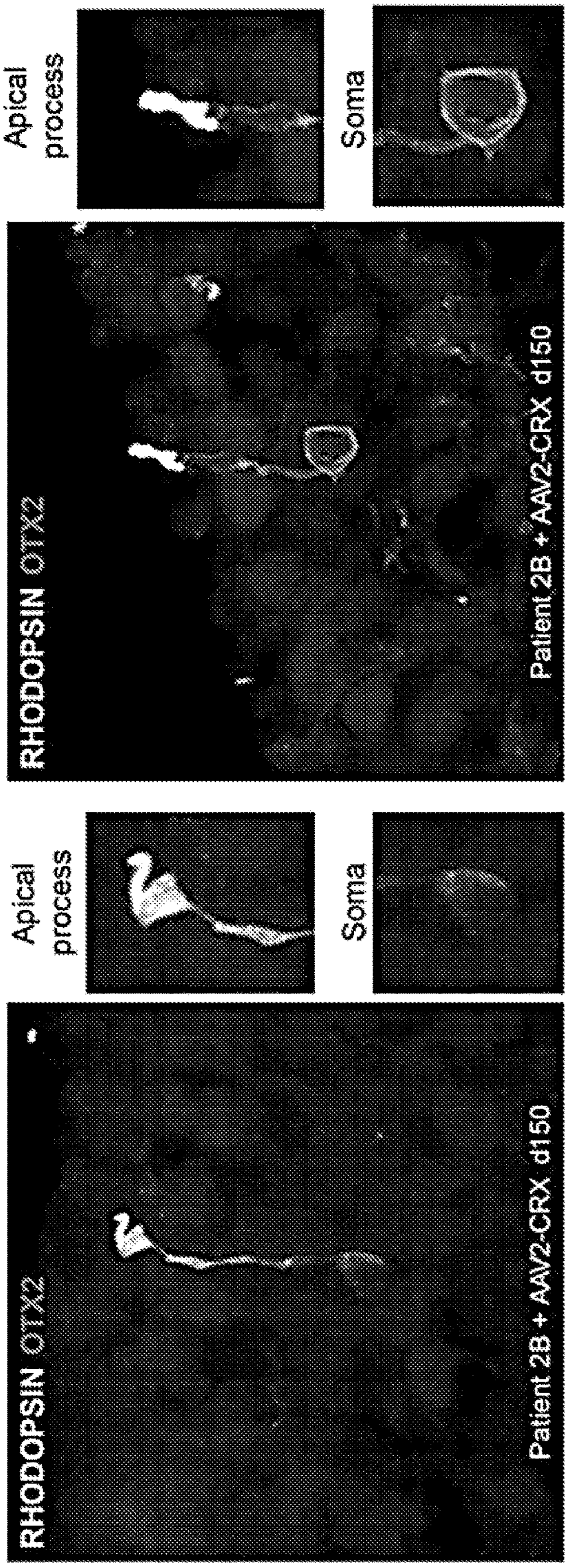
FIG. 4. AAV treatment rescues apical accumulation of Rhodopsin in c.413delT (p.I138fs48) patient retinal organoids. Retinal organoids treated with AAV-CRX vector at day 150, collected and analyzed 4 weeks following treatment and immunostained for Rhodopsin and OTX2. Rhodopsin accumulation in apical process is evident in cells with rescued expression of Rhodopsin.

Rescue of Opsin Expression in CRX-LCA Patient Organoids by AAV-CRX Gene Therapy Treatment A gene therapy vector containing 631 nt CRX composite promoter that guided the expression of CRX coding sequence for treatment was used in retinal organoids at day 120 of differentiation. The organoids were harvested at day 150 (after 4 weeks) and analyzed by histology (FIGS. 3A-3H). Immunostaining using anti-Rhodopsin antibody (FIG. 3A-C) revealed a robust staining in healthy control organoids (FIG. 3A). A smaller number of cells also expressed Rhodopsin in the patient-derived organoids with AAV-CRX gene therapy treatment group (FIG. 3C), in contrast to untreated patient organoids, which did not show any Rhodopsin immunostaining (FIG. 3B). Quantification of CRX-positive cells that expressed Rhodopsin revealed a modest but significant restoration of its expression (FIG. 3G). Similarly, L/M Opsin was highly expressed in the healthy control organoids 4 weeks later at day 150 (FIG. 3D), but its expression was undetectable in patient-derived organoids (FIG. 3E). As with Rhodopsin, AAV-CRX gene therapy treatment restored L/M Opsin expression in some of the photoreceptors in patient organoids (FIG. 3F, quantified in H). A key characteristic of appropriate Rhodopsin expression is its localization with high concentration in apical outer segment structures in photoreceptor cells. It was therefore examined whether treatment with AAV-CRX gene therapy could rescue this apical enrichment. Importantly, Rhodopsin immunostaining in treated patient organoids was highly concentrated in apical structures of photoreceptor cells showing rescue of expression (FIG. 4).

Figures 5A, 5B, 5C, 5D:
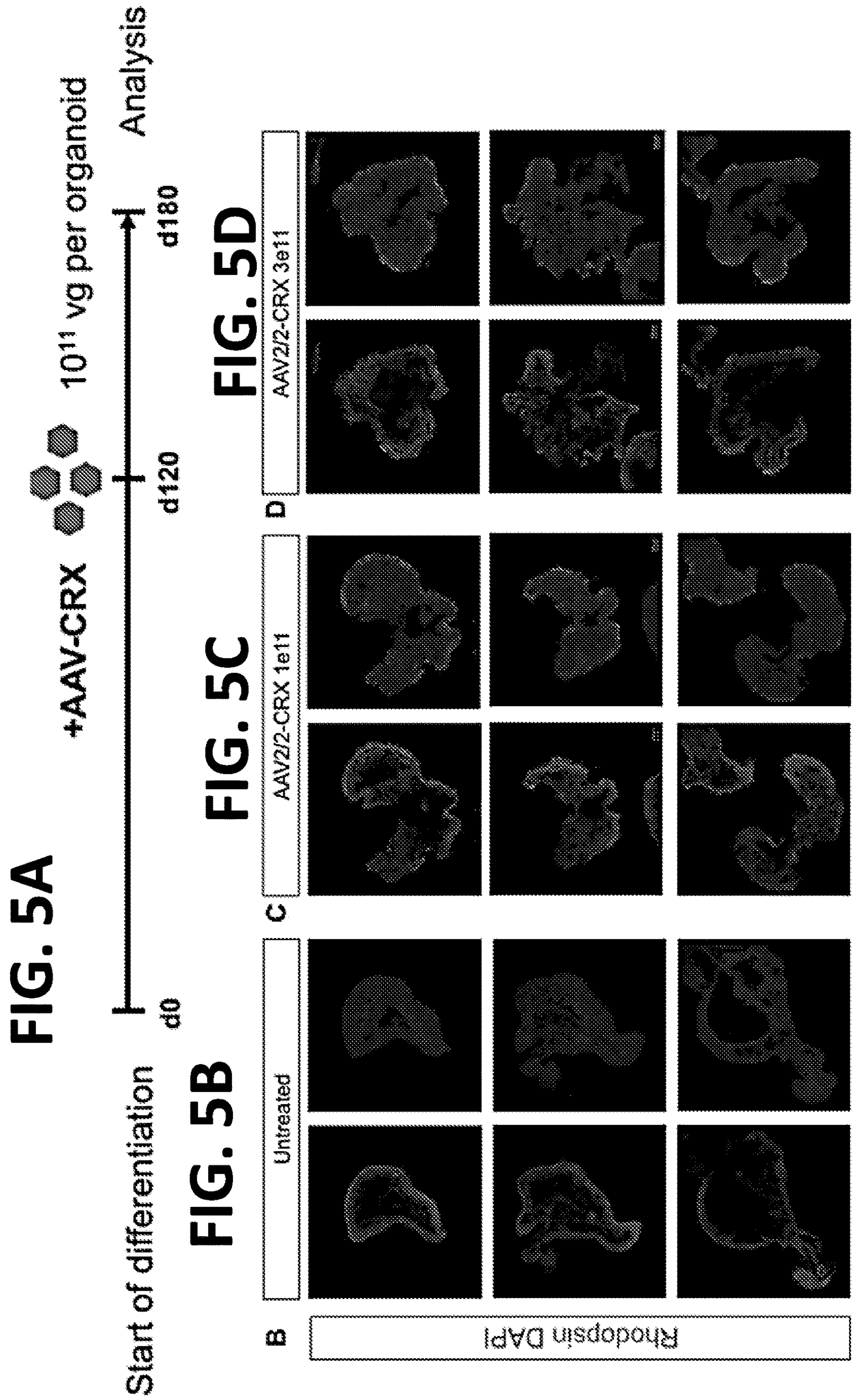
FIGS. 5A-5D. Significant restoration of Rhodopsin expression in c.413delT (p.I138fs48) CRX-LCA retinal organoids 8 weeks post AAV-CRX treatment. (A) Overview of treatment timeline. (B-D) Retinal organoids were cryosectioned and immunostained for Rhodopsin, nuclei were counterstained with DAPI. Untreated CRX-1138fs patient organoids (B) lack Rhodopsin immunostaining, whereas AAV-CRX treated organoids at low ($1\times10^{11}$ vg/organoid; C) and high dose ($3\times10^{11}$ vg/organoid; D) show the restoration of Rhodopsin staining at d180.
Figure 6A:
FIGS. 6A-6C. Quantification of Rhodopsin expression rescue following AAV-CRX treatment of c.413delT (p.I138fs48) patient retinal organoids. (A) Timeline of treatment. (B) Immunostaining of Rhodopsin in unaffected familial control as well as untreated and AAV-CRX treated patient organoids. (C) Quantification of Rhodopsin fluorescence intensity in relation to familial control sample. At least three organoids per group, Student's t-test, p values indicated.
Figure 6B:
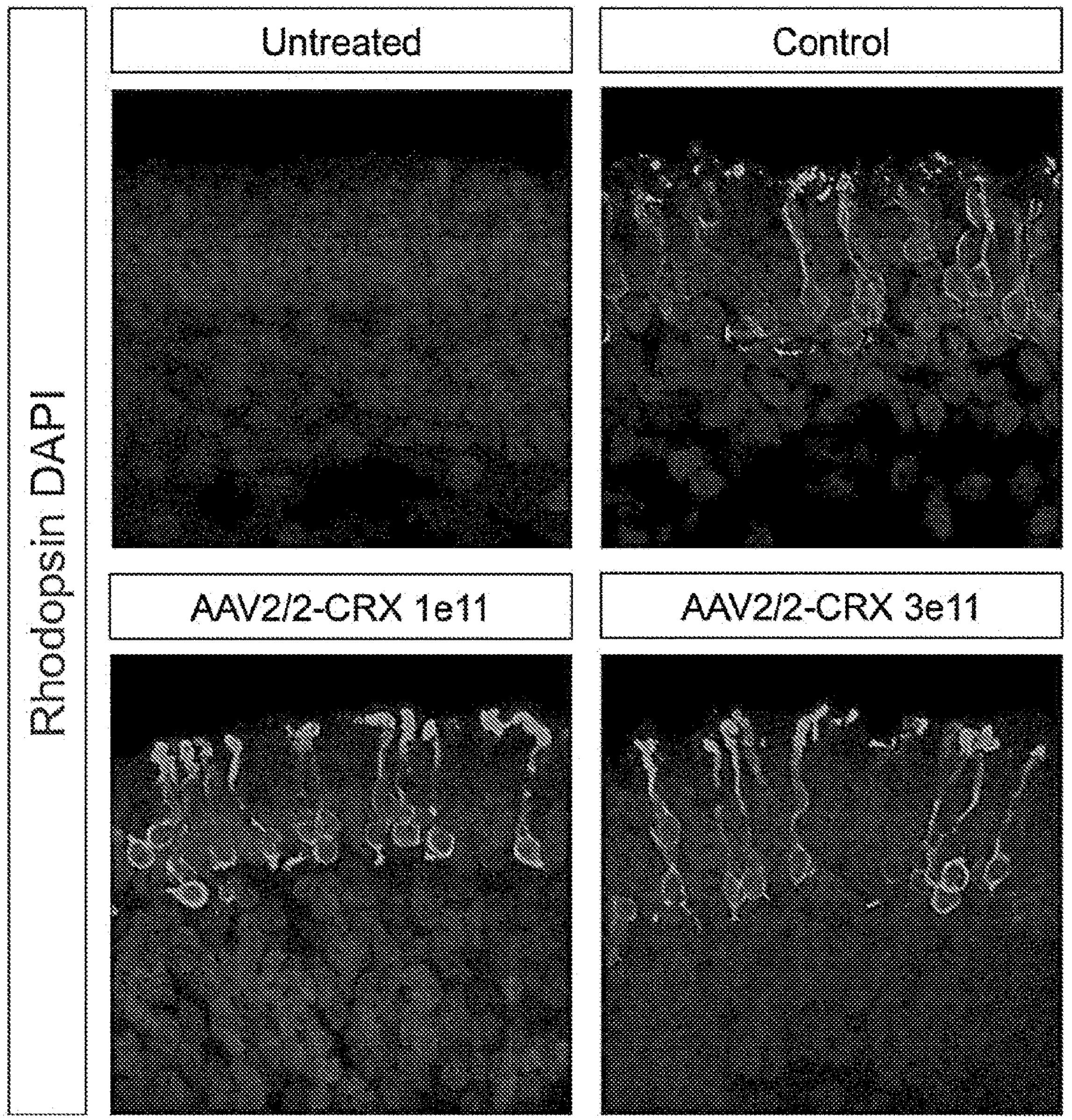
Figure 6C:
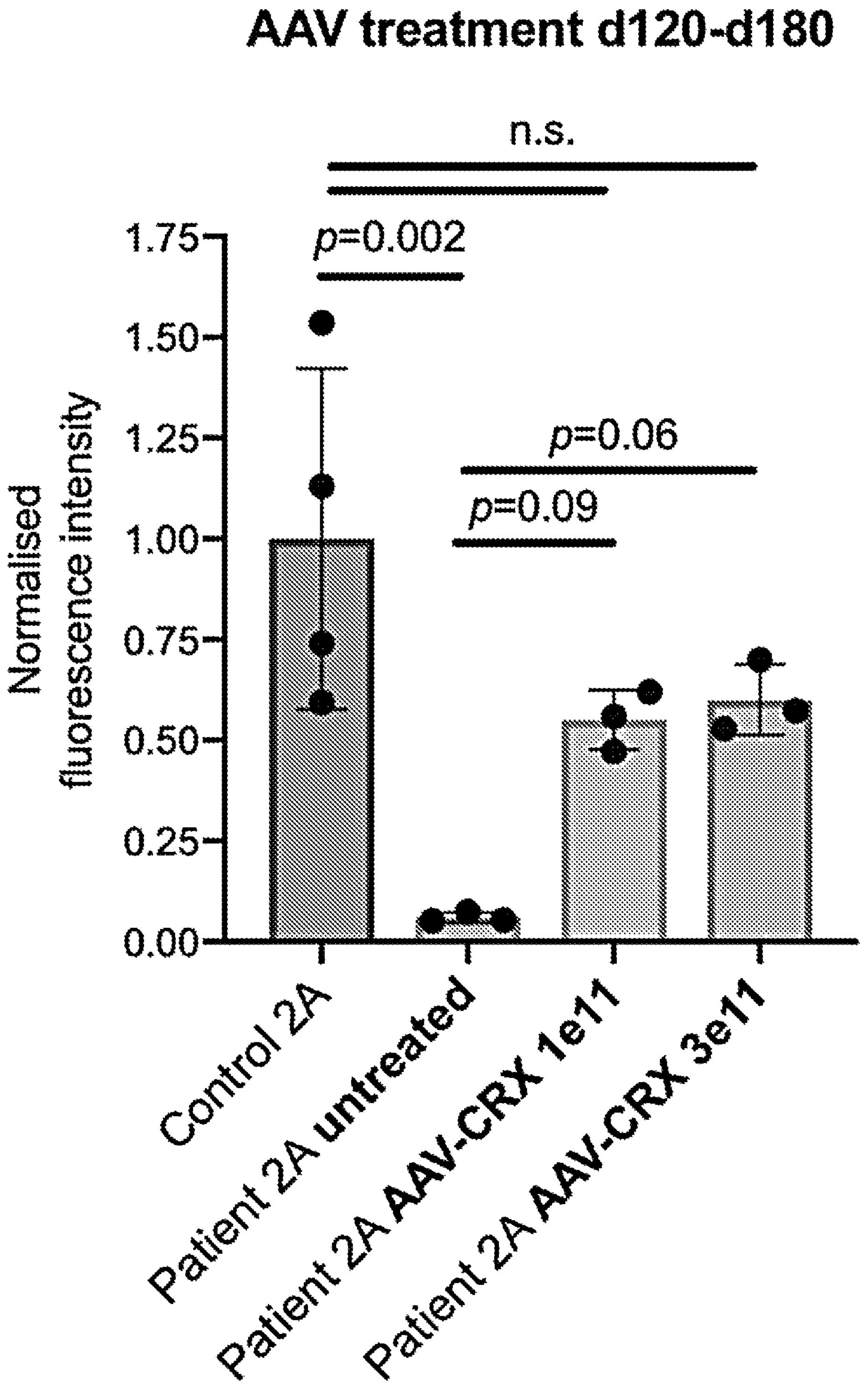

The rescue of Rhodopsin expression was examined at day 180, 2 months after AAV transduction that was performed at day 120 (FIG. 5A). At this stage, Rhodopsin expression was still not detected in patient organoids (FIG. 5B) but was evident across multiple treated organoids, both at a lower dose of $1\times10^{11}$ vg per organoid (FIG. 5C) as well as higher dose of $3\times10^{11}$ vg of AAV-CRX gene therapy vector per organoid (FIG. 5D). The intensity of Rhodopsin immunostaining was quantified in these samples (FIG. 6A, 6B). While untreated patient organoids had very low background levels of the signal, fluorescence intensity in the samples treated with AAV-CRX reached about half of the level of healthy familial control organoids for both the lower $1\times10^{11}$/organoid as well as higher $3\times10^{11}$/organoid doses of vector (FIG. 6C). Moreover, L/M Opsin expression was also noticeably rescued at day 180 with both vector doses (FIG. 7).

Figure 8:
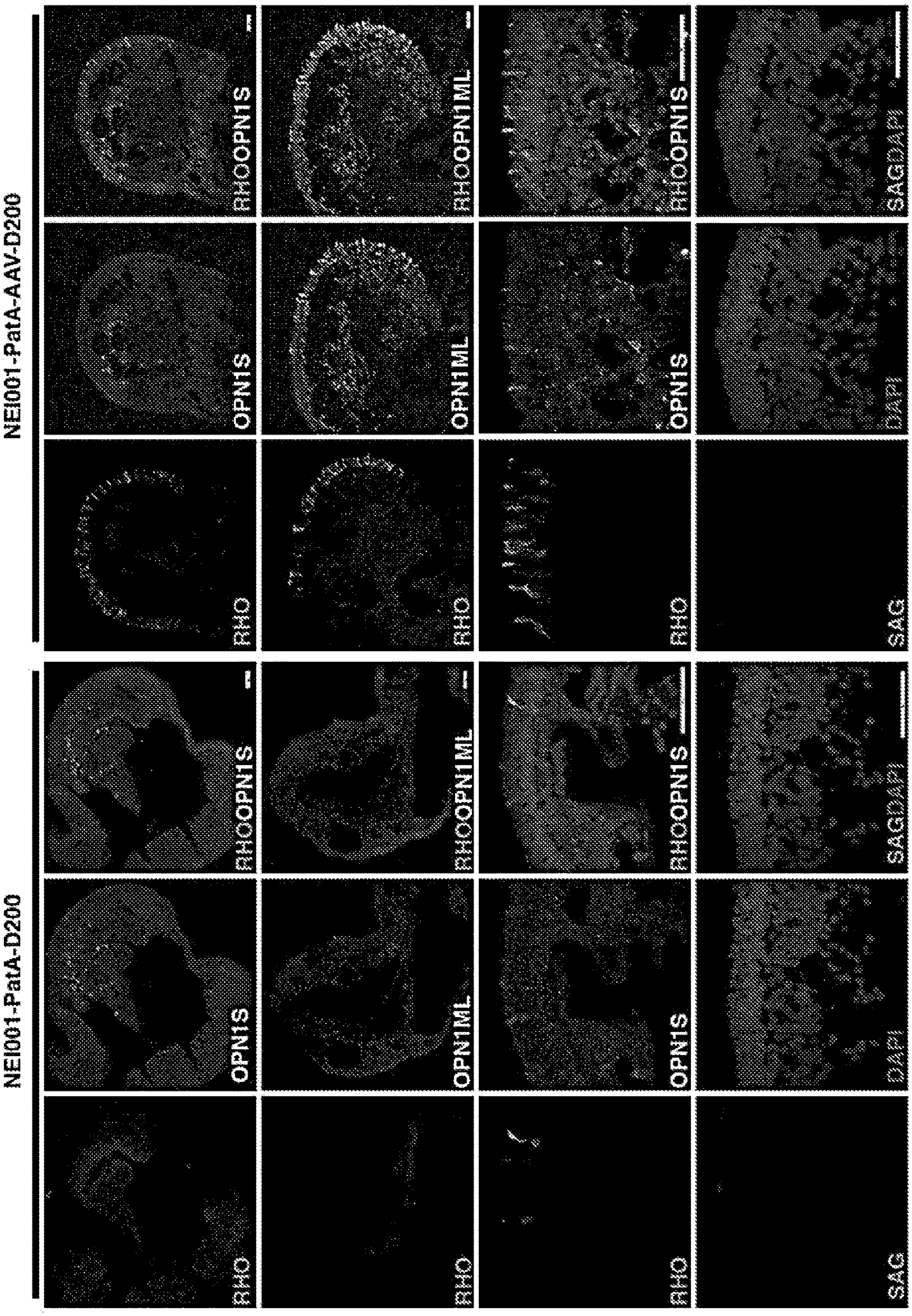
FIG. 8. Treatment of c.G264T (p.K88N) CRX-LCA patient (second subject) organoids. Organoids from the second CRX-LCA patient before and after AAV-CRX treatment were stained for a panel of markers including Rhodopsin (RHO), blue Opsin (OPN1S), red-green Opsin (OPN1ML) and rod arrestin (SAG), as in case of the first subject (shown in FIGS. 4-8). Scale bar 20 μm. Nuclei were counterstained with DAPI.

In addition, iPSCs were differentiated from another CRX-LCA patient, carrying a K88N mutation in the DNA binding domain, predicted to lead to a loss of DNA binding. Organoids from this patient also did not correctly express Rhodopsin and L/M Opsin (FIG. 8), suggesting converging underlying molecular pathology in the two patients. As with the frameshift mutation, expression of Rhodopsin as well as L/M Opsin could be rescued by AAV-CRX gene therapy in the organoids (FIG. 8).

Figure 9A:
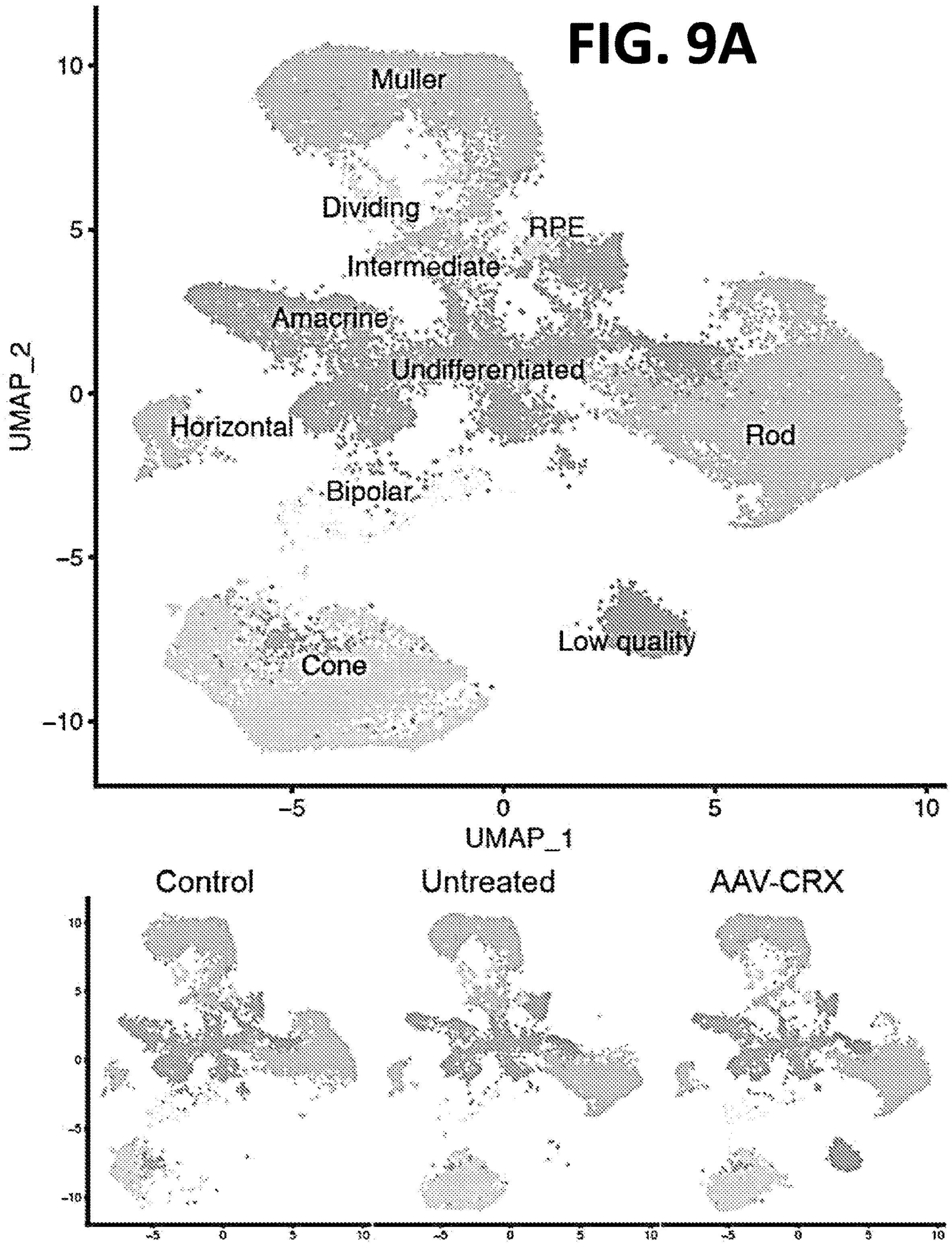
FIGS. 9A-9I. Altered gene expression patterns and AAV treatment effects in cone and rod photoreceptor subtypes of CRX-I138fs48 patient retinal organoids at d200. (A) Upper panel: UMAP representation of the single-cell RNA-seq dataset (n=40,712 transcriptomes) displaying major cell types (annotated using known cell-type marker genes). Lower panel: UMAP plots showing the distribution of cells of control (n=2 biological replicates, 4 organoids each), and untreated and AAV-CRX (n=2 biological replicates, 3 organoids each) organoid samples. (B) Expression of photoreceptor cell type-(CRX, RCVRN) and subtype-specific markers (rods: GNGT1, GNAT1; cones: ARR3, PDE6H). (C) Violin plot profiles of CRX expression levels in rods and cones. Note increased expression with AAV-CRX gene augmentation. Treatment effects in rod (D-F) and cone (G-I) photoreceptor subtypes. (D,G) UMAP plots showing the distribution of rod and cone cells by sample origin. (E,H) Hexagonal bin plots illustrating identity of cell origin. Note placement of AAV-CRX treatment samples (light gray color) between patient and control areas (dark gray shading). (F,I) Opsin transcript reads in the different samples visualizing increased expression in patient-derived samples following treatment. Percentages of cells of each origin in which transcript reads were detected are indicated.
Figure 9B:
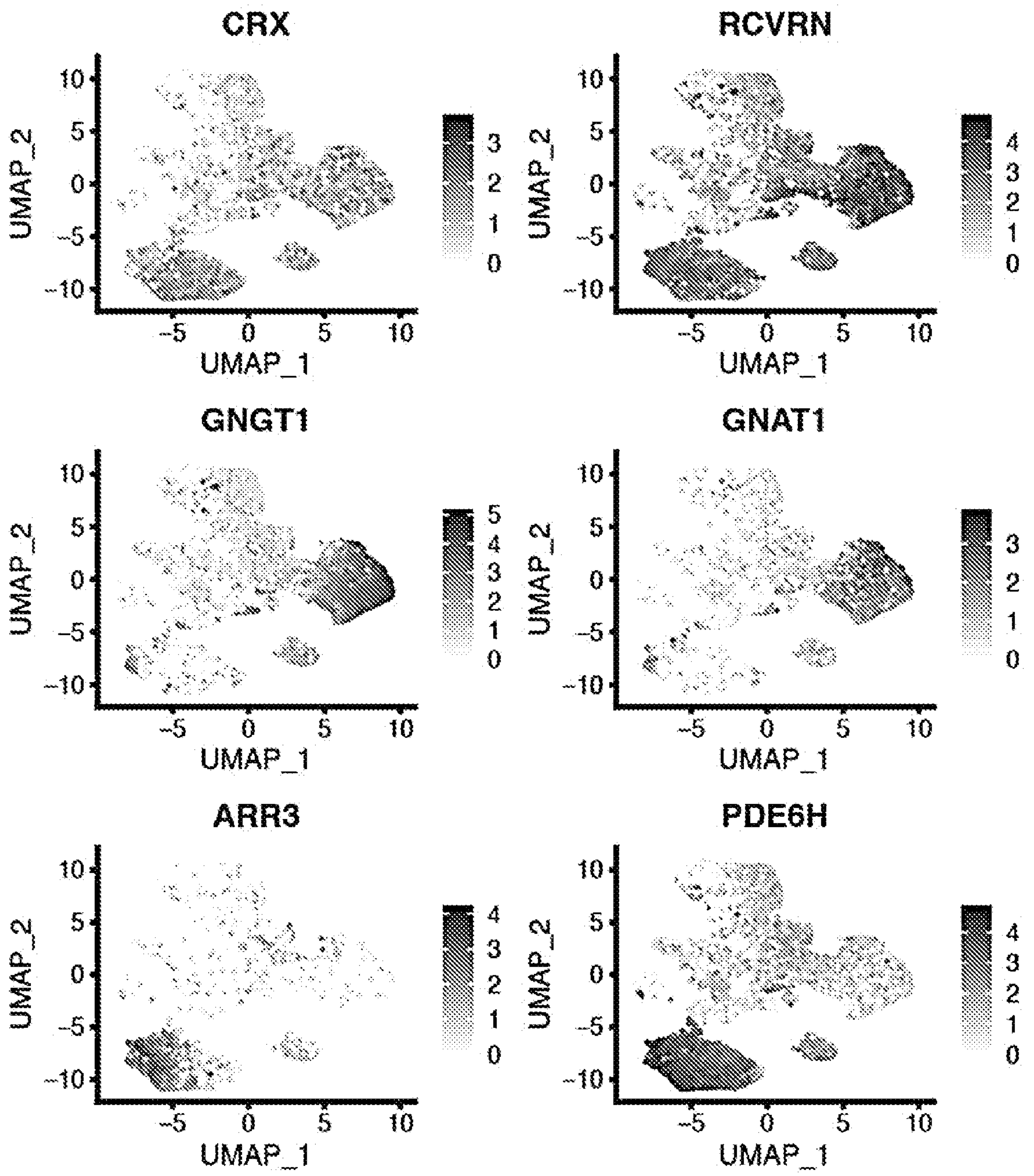
Figure 9C:
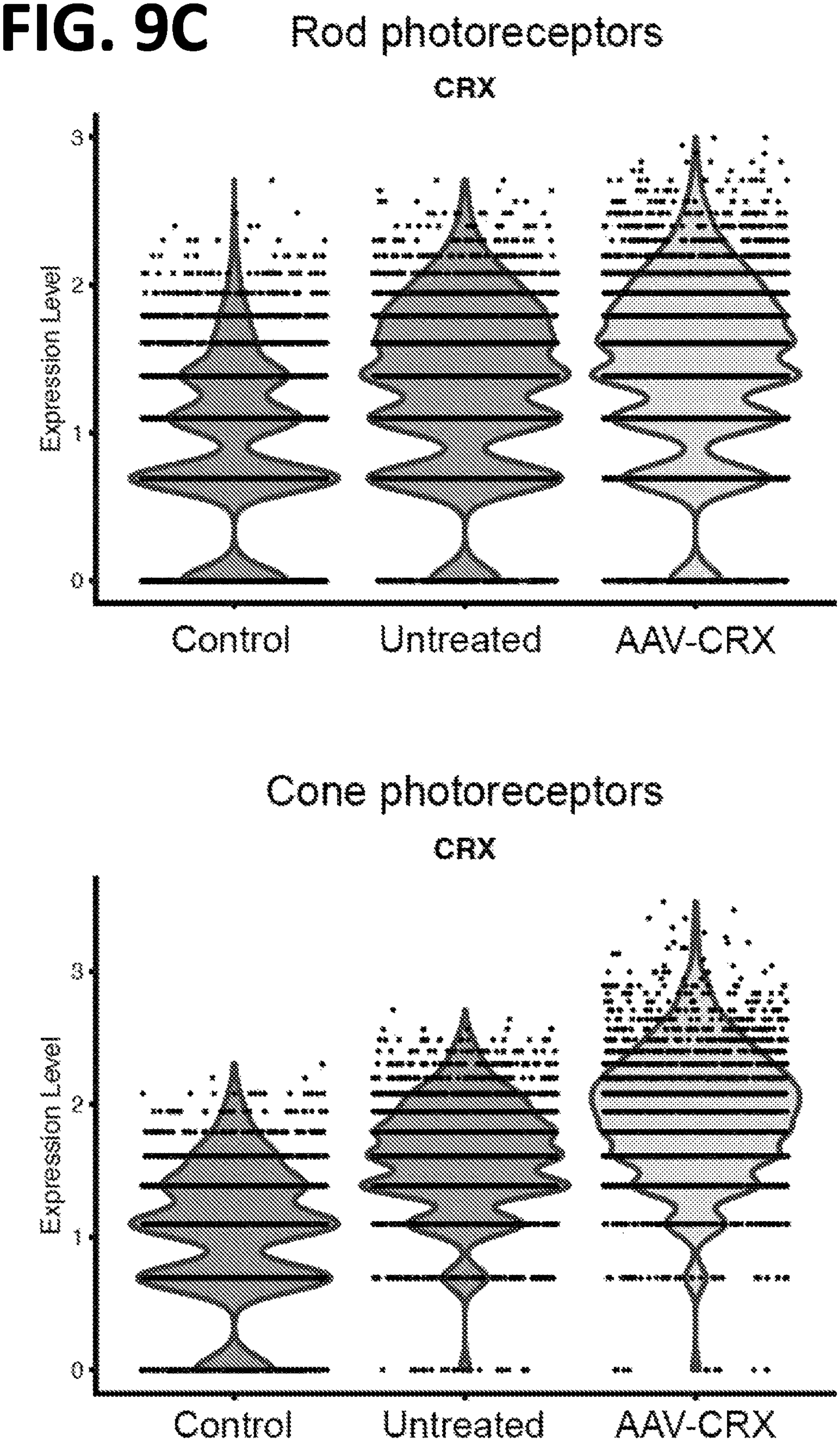
Figure 9D:
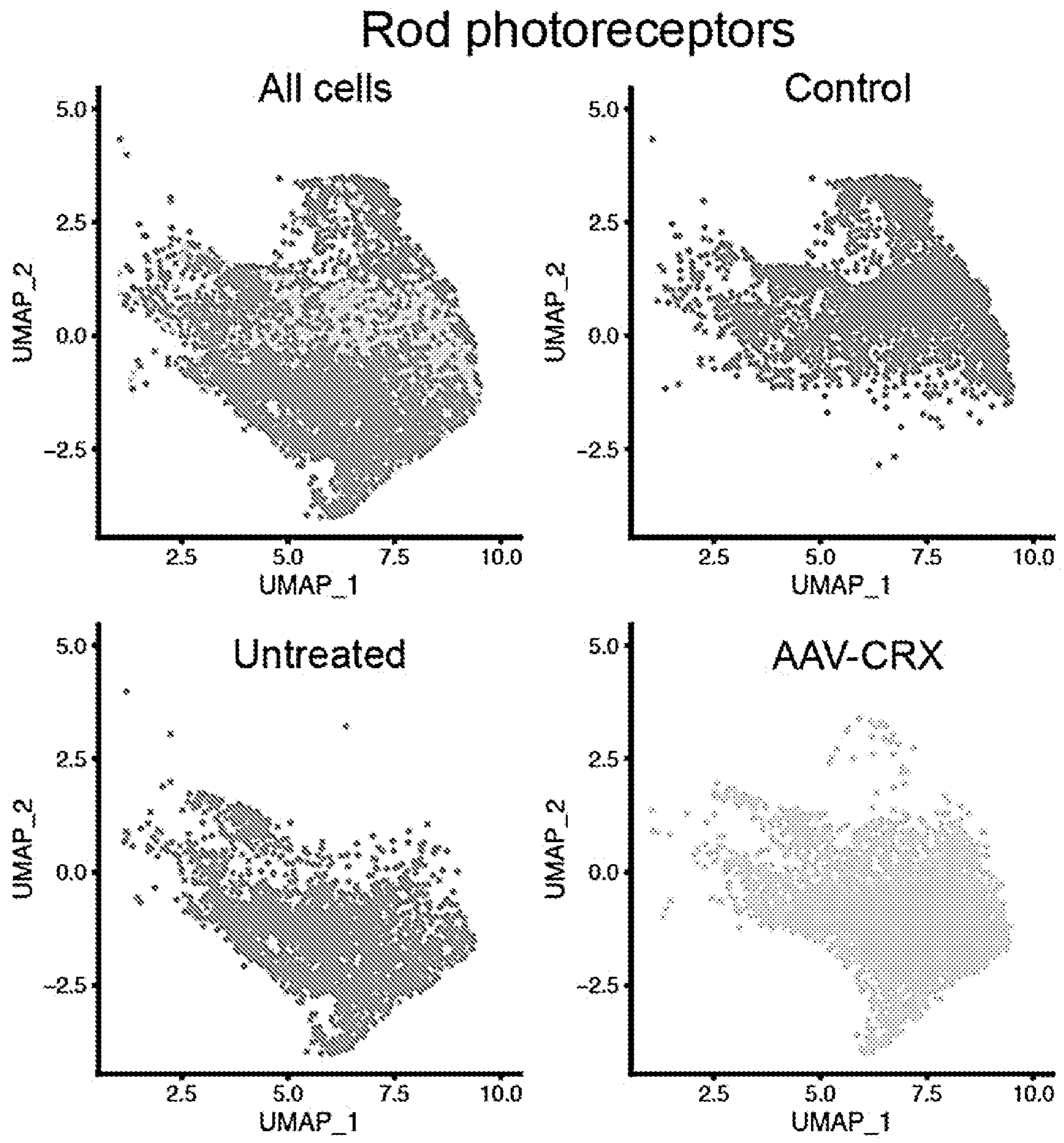
Figure 9E:
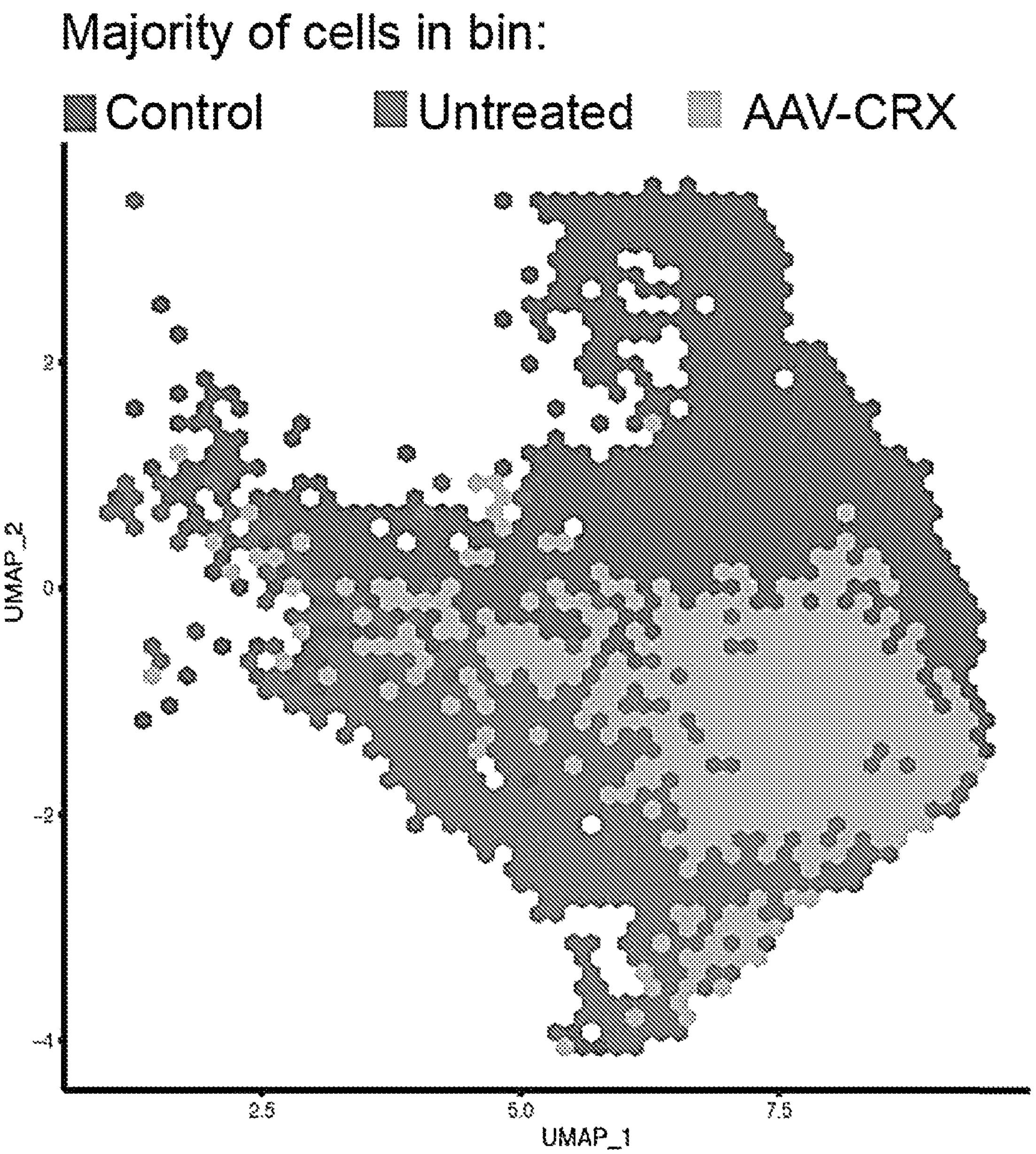
Figure 9F:
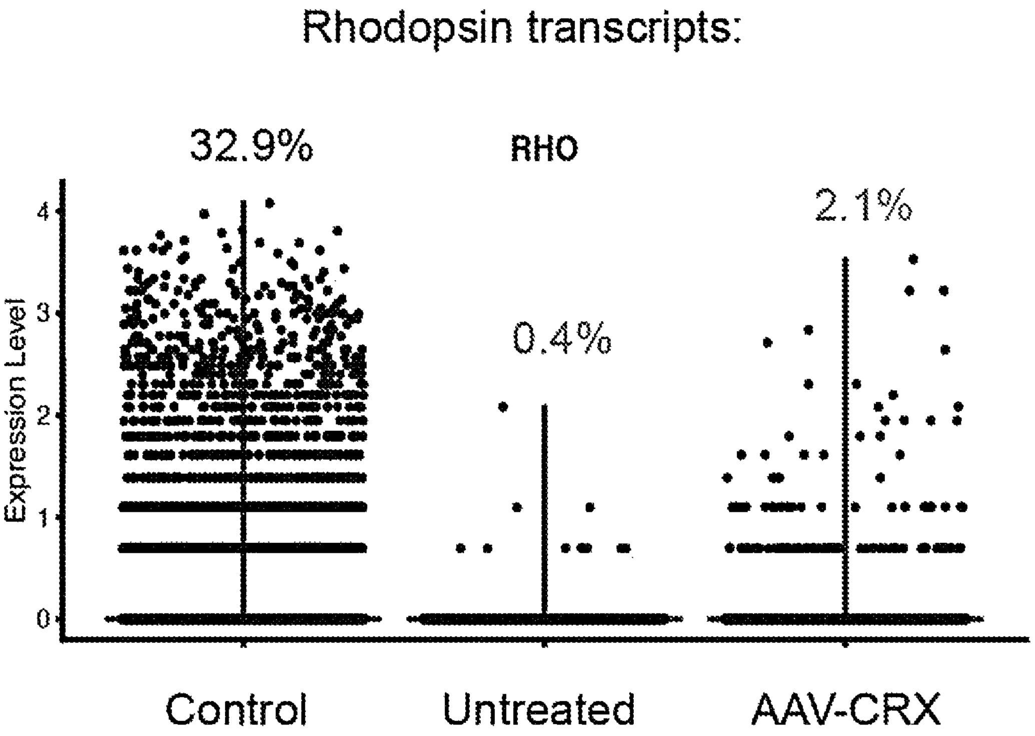
Figure 9G:
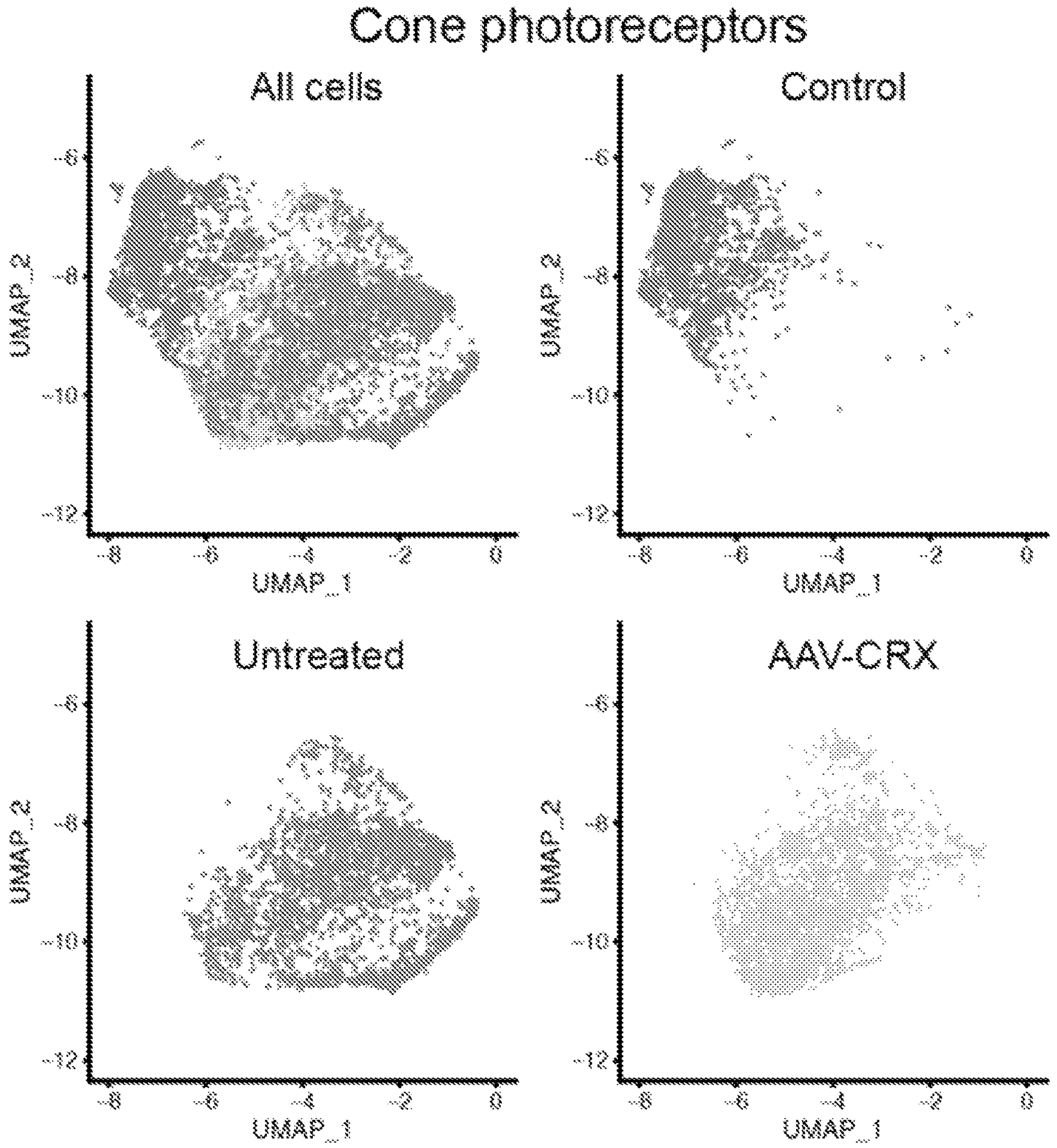
Figure 9I:
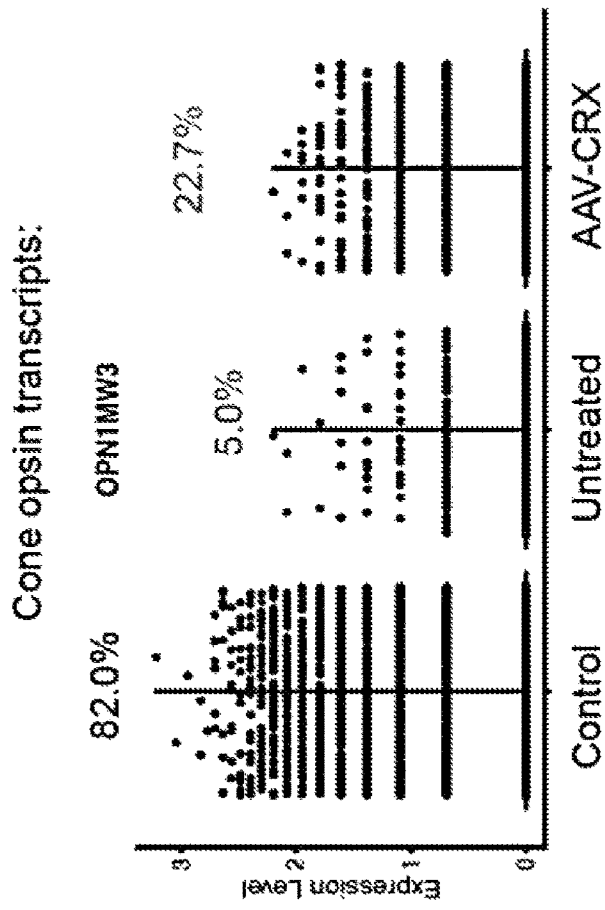
Figure 9H:
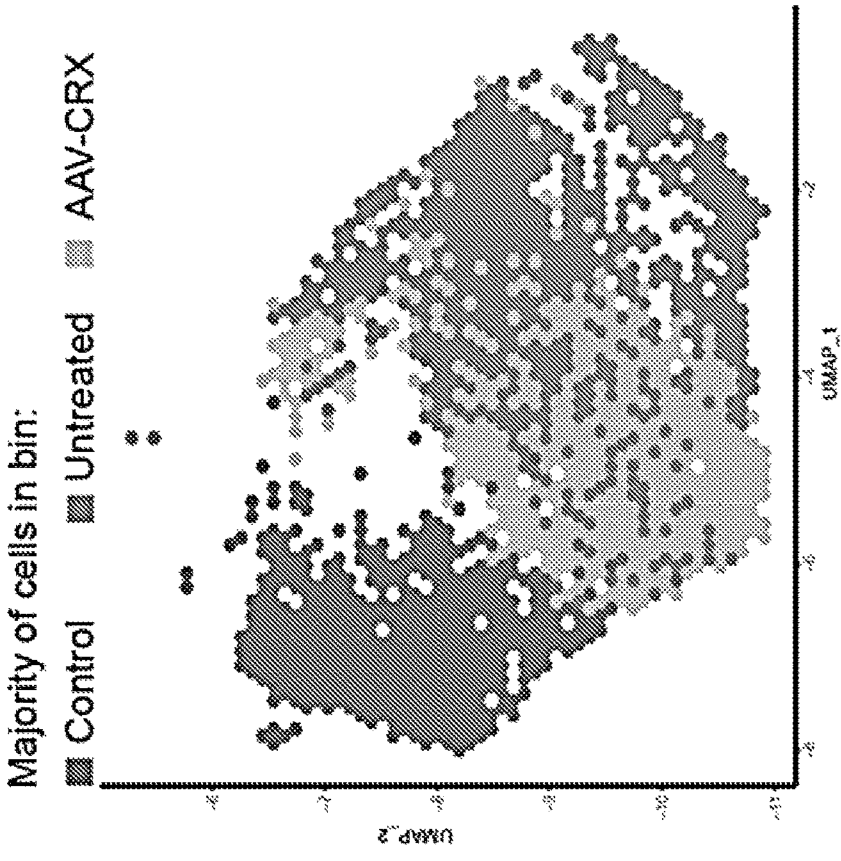
Figure 10A:
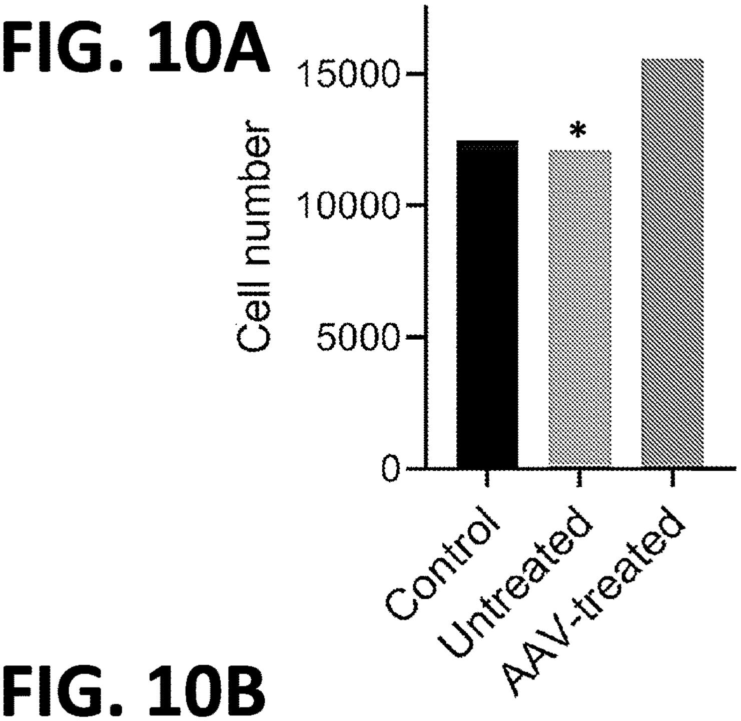
FIGS. 10A-10G. Cell type diversity in CRX-LCA retinal organoids and gene augmentation effects revealed by single cell transcriptomics. (A) Number of single cell transcriptome profiles obtained from control (12496 cells), untreated (12126 cells) and AAV-treated CRX-I138fs (15550 cells) organoids at d200. (B) Cell type distributions across various conditions. (C) Heatmap of 3 top transcripts most significantly enriched in each assigned cell class in the combined data set. The molecular markers were used to define cell types across experimental conditions. (D) Examples of specific transcript expression rescued by AAV treatment in rod photoreceptors. For all genes adjusted p value<0.05, Wilcoxon rank sum test with Bonferroni correction; min. percent expressed=10% cells, min. log fold change=0.25. (E) Example of cone transcripts rescued by AAV treatment. (F,G) Expression of CABP4, a retinal disease-associated direct transcriptional target of CRX, in rod (F) and cone (G) photoreceptors, showing a trend toward higher expression after AAV treatment.
Figure 10B:
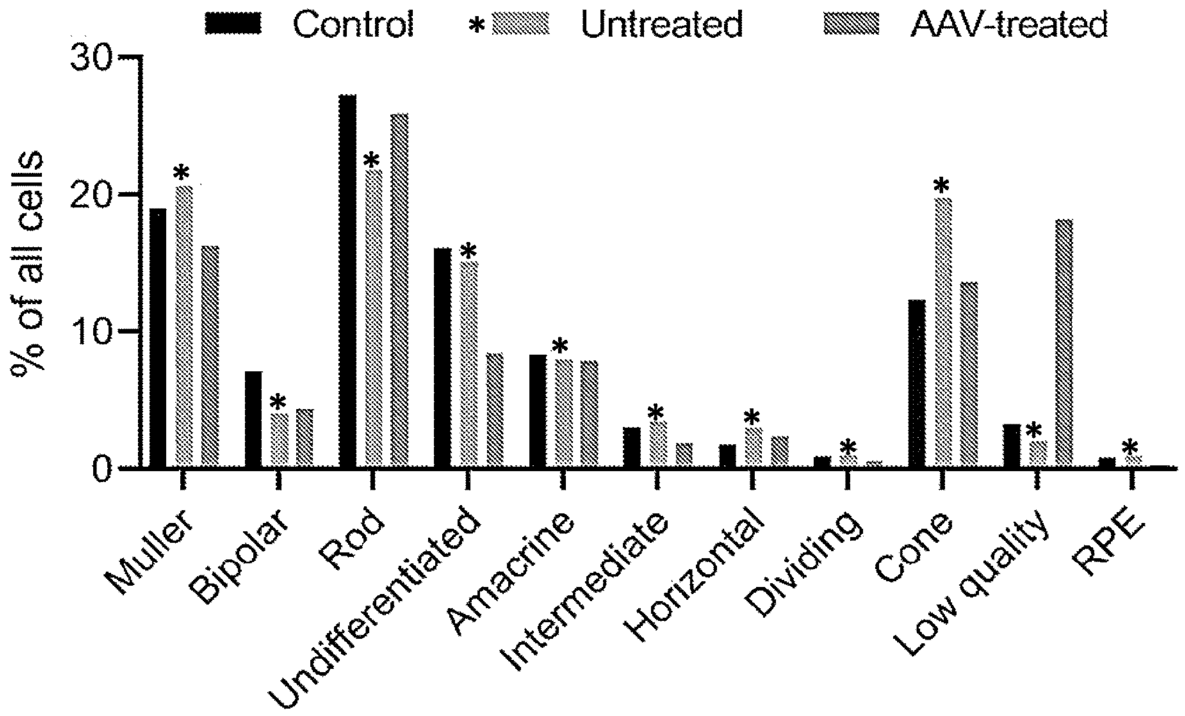
Figure 10C:
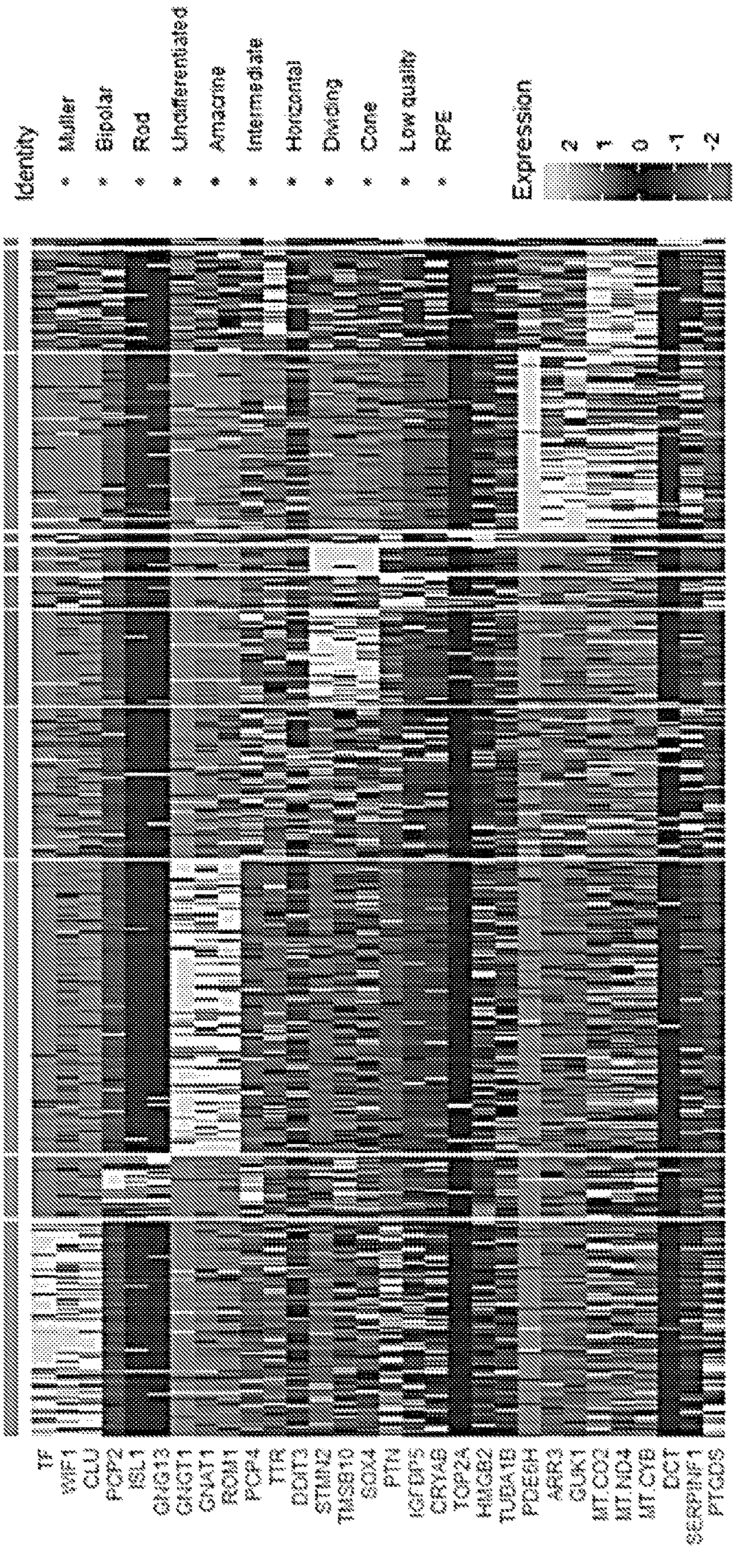
Figure 10E:
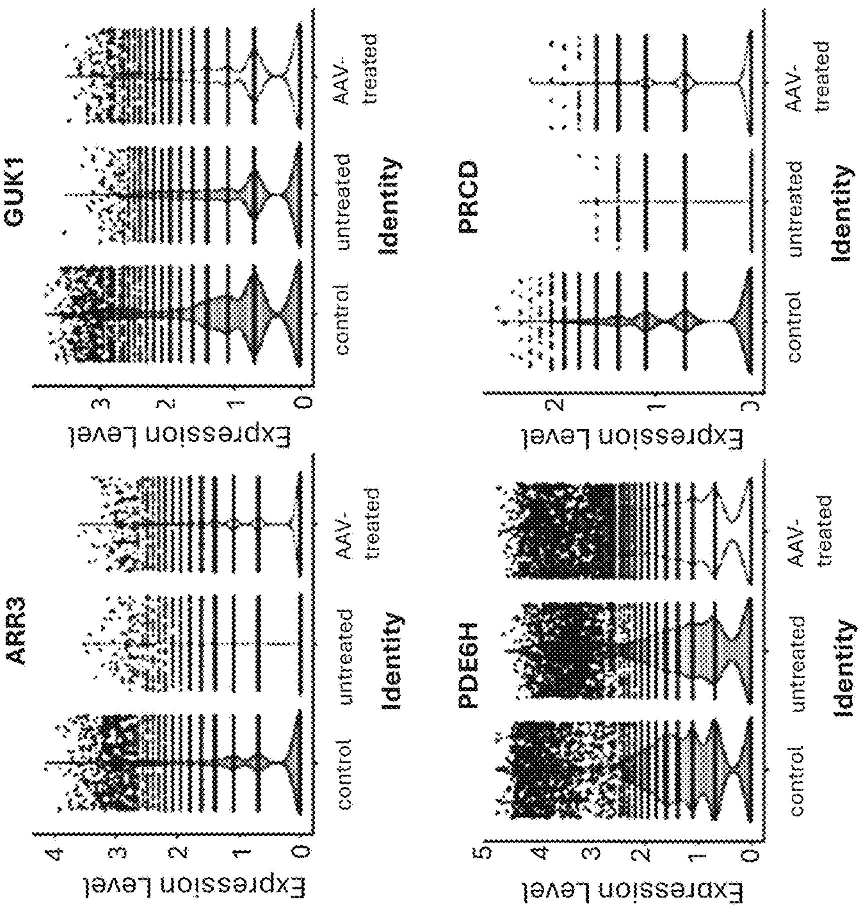
Figure 10D:
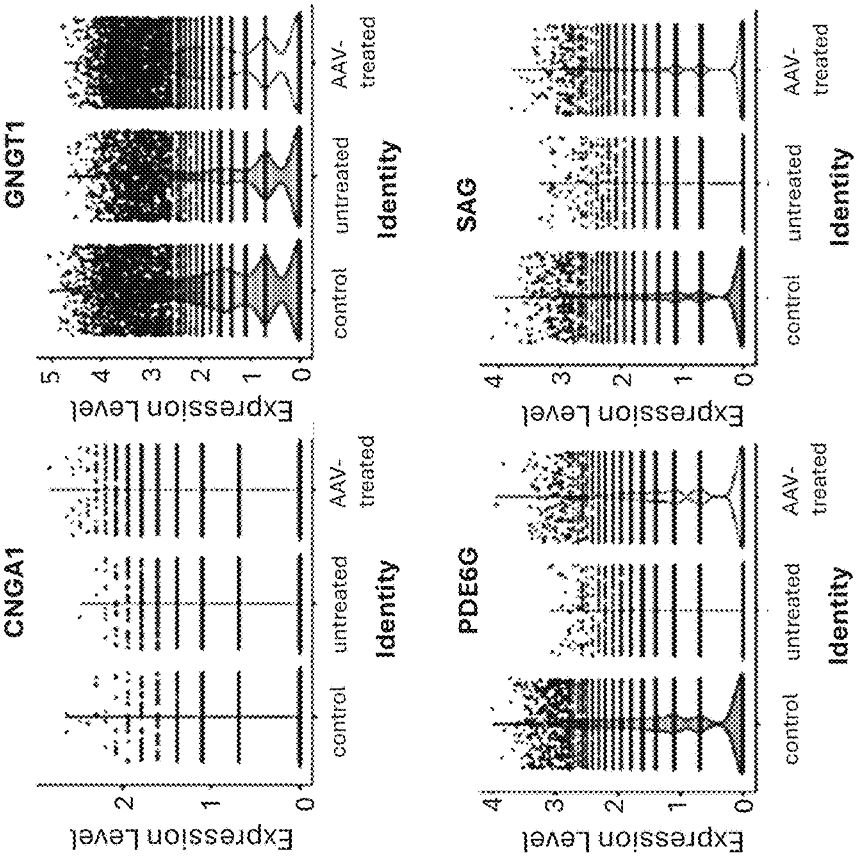
Figure 10F:
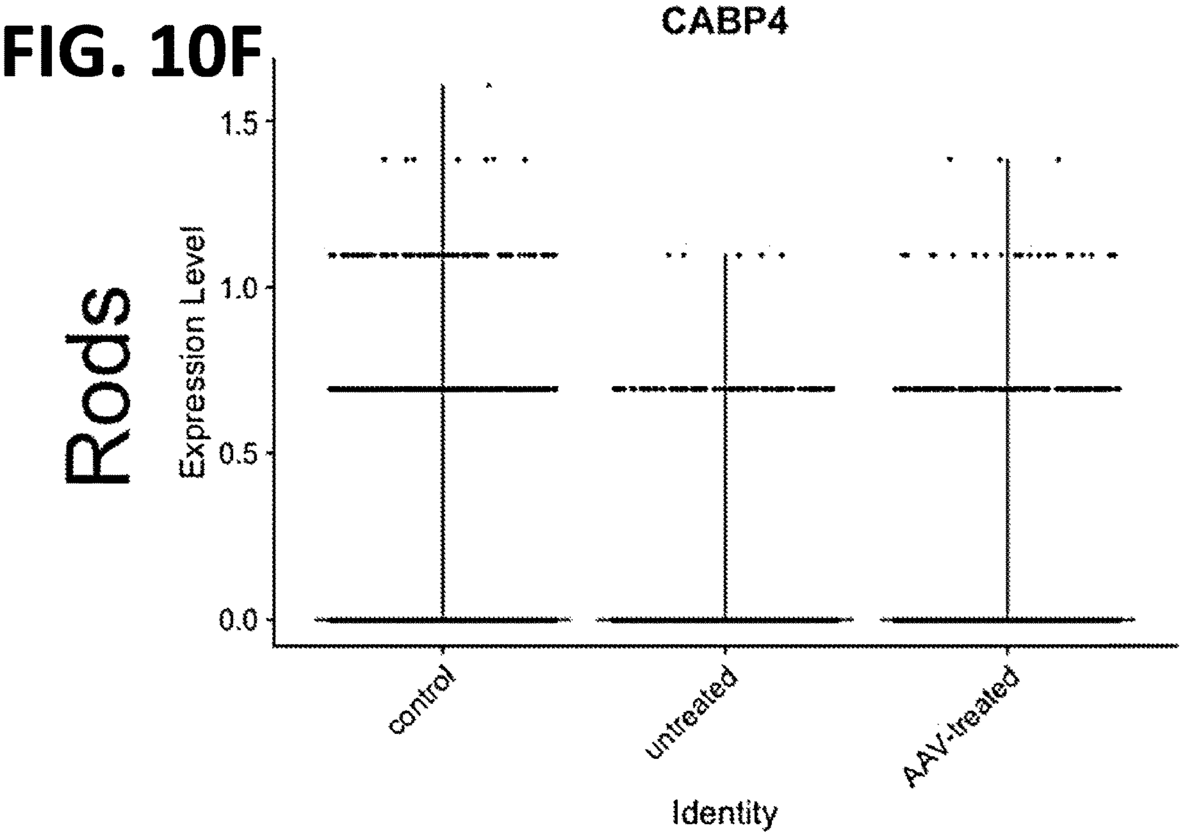
Figure 10G:
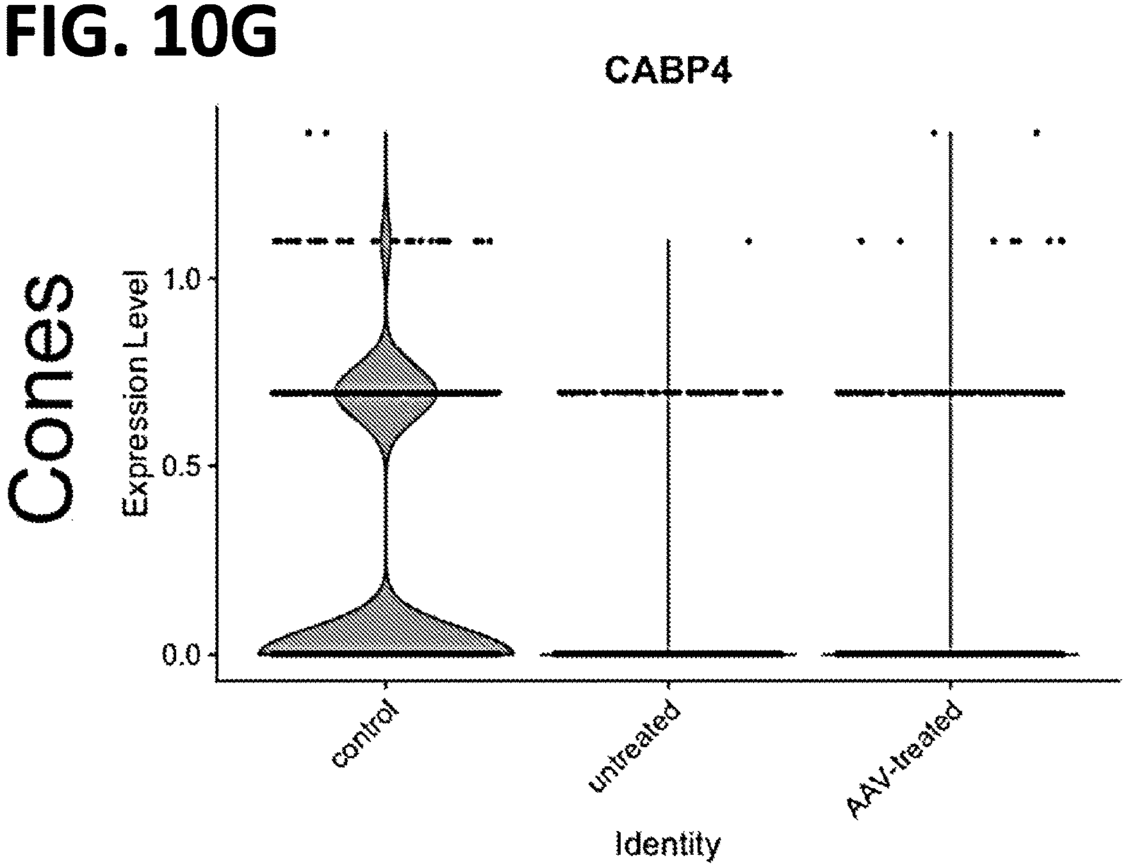

To decipher and validate the impact of CRX I138fs mutation on specific cell types within retinal organoids, single cell RNA sequencing (scRNA-seq) was performed using a 10× Genomics platform. Control, untreated CRX-I138fs and AAV-treated organoids were dissociated using a papain-based method (Fadl et al., *Molecular Vision* 26, 705-717, 2020) at d200 yielding 40,712 single cell transcriptional profiles. Data processing using Seurat package identified cell clusters, which were assigned to known retinal cell types and visualized using UMAP dimension reduction (FIG. 9A; FIG. 10A-C). In this representation, major retinal cell classes (apart from ganglion cells) emerge from centrally located undifferentiated cells (FIG. 9A). Cell type distribution was similar across the three sample origins (FIG. 9A; FIG. 10B). Rods and cones formed well-defined differentiation trajectories in this manifold and were identified by expression of both common (CRX, RCVRN) and subtype-specific markers (rod: GNGT1, GNAT1; cone: ARR3, PDE6H; FIG. 9B). As predicted, CRX transcripts increased in photoreceptors after AAV-CRX transduction (FIG. 9C). Rod and cone expression profiles could be clearly separated based on control or patient sample origin, whereas AAV-treated cells occupied the space in between (FIG. 9D, 9E, 9G, 9H). This shift was particularly evident by plotting the origin of majority of cells across hexagonal bins (FIG. 9E, 9H). ScRNA-seq detected partially rescued expression of Opsins following AAV treatment (RHO, OPN1MW3, FIG. 9F,I; OPN1MW3 was the most significantly dysregulated of 3 medium wavelength opsin genes OPN1MW1-3), as well as of other rod- and cone-specific transcripts (FIG. 10D, 10E; for each gene adjusted p value<0.05, non-parametric Wilcoxon rank sum test with Bonferroni correction; min. percent expressed=10% cells, min. log fold change=0.25). CABP4, a retinal disease gene and direct transcriptional target of CRX (Assawachananont et al., 2018) showed a similar trend (FIG. 10F, 10G). Thus, single cell analysis confirmed treatment effect of AAV-mediated overexpression of normal CRX.

Figure 11A:
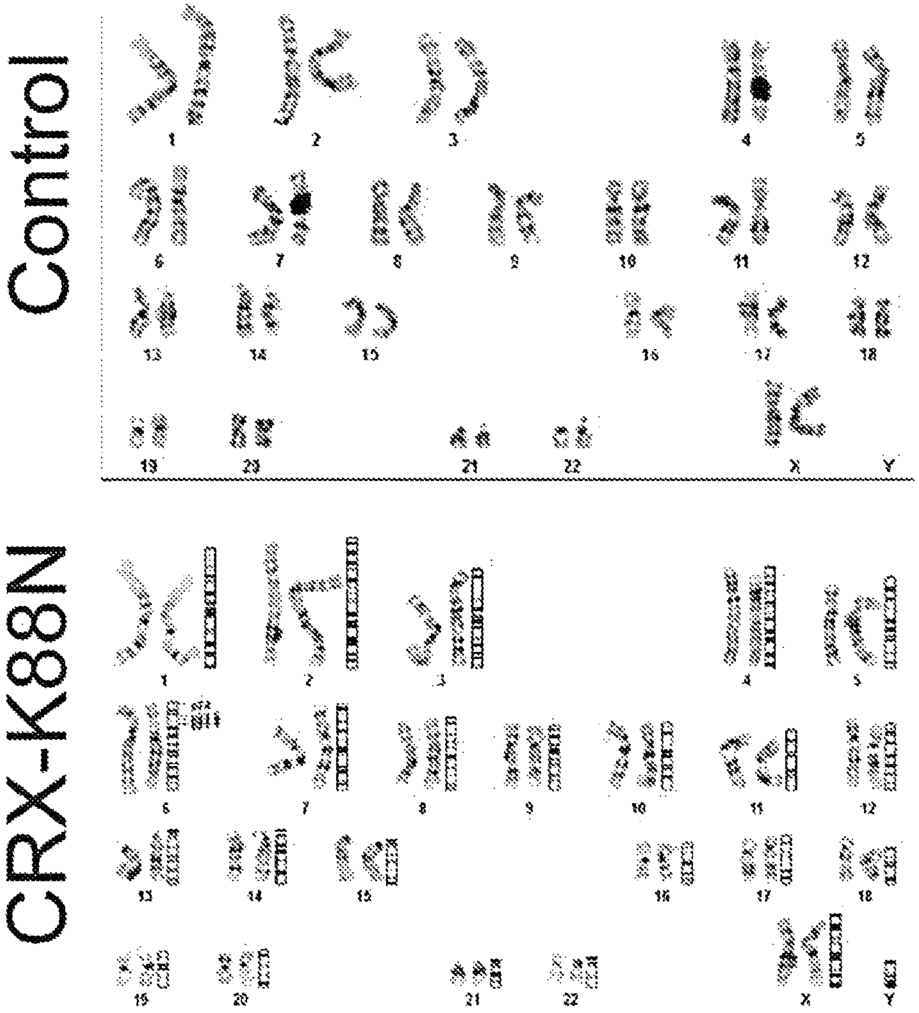
FIGS. 11A-11E. Differentiation of retinal organoids from CRX-K88N patient iPSCs. (A) Representative karyograms of control and CRX-K88N iPSC lines. (B) Immunostaining using pluripotency and proliferation markers in control and CRX-K88N iPSC colonies. (C) Brightfield images of organoid retinal epithelia at d90. Scale bar, 200 μm. (D) Immunostaining for OTX2, CRX and Recoverin in control and CRX-K88N retinal organoids at d70 of differentiation. All three markers showed similar staining between the two genotypes. (E) Immunostaining for S Opsin and Calbindin in control and CRX-K88N retinal organoids. Note an increased Calbindin staining in patient organoids at d200. Scale bars in B,D,E, 100 μm.
Figure 11B:
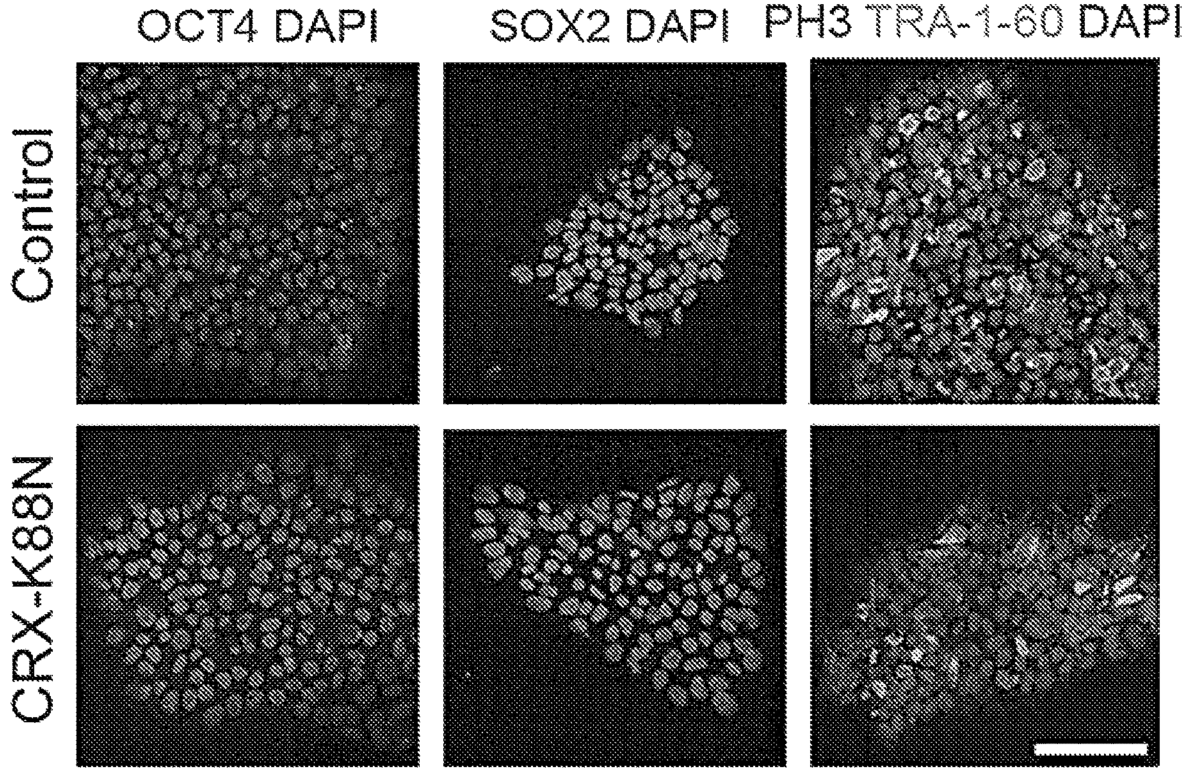
Figure 11C:
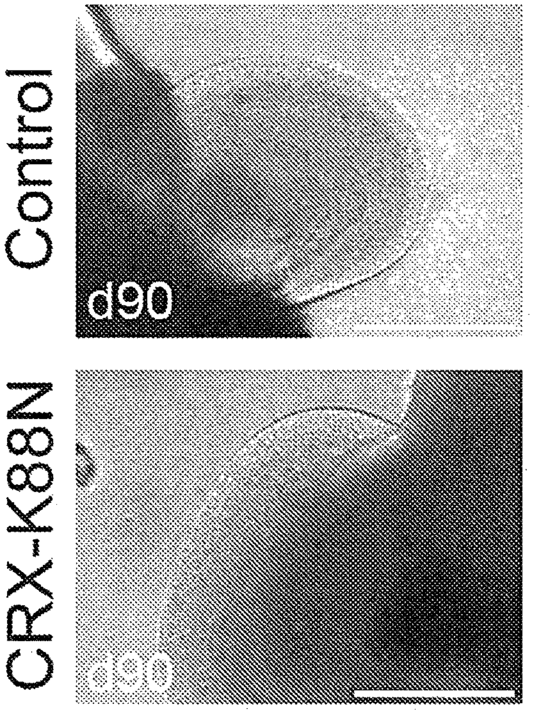
Figure 11E:
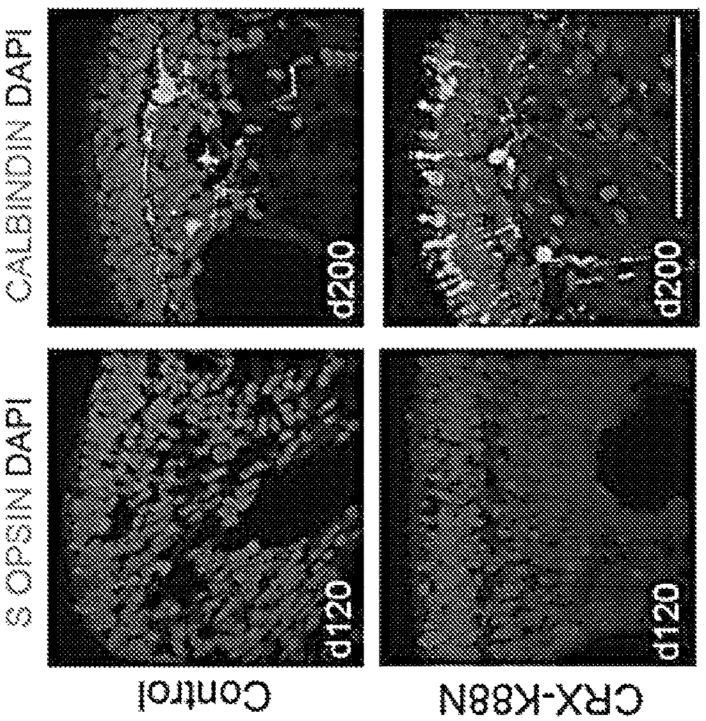
Figure 11D:
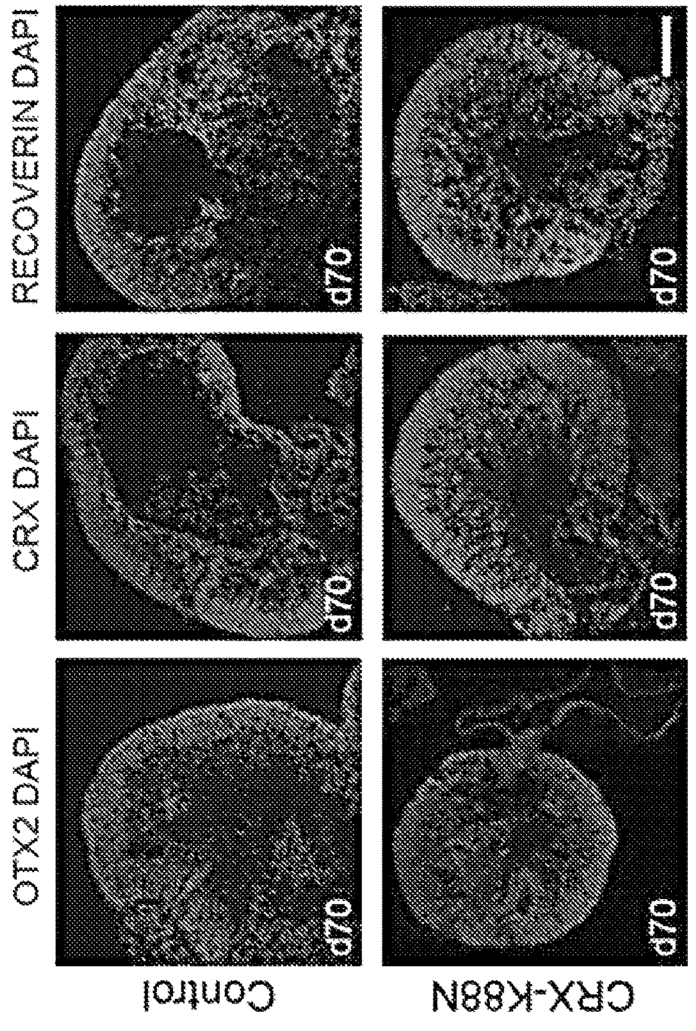
Figure 12A:
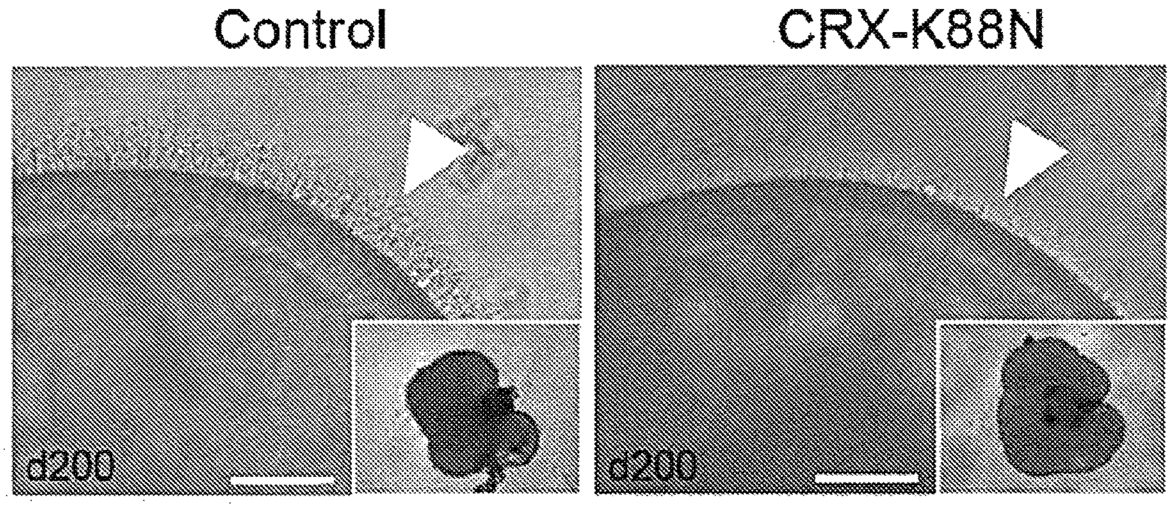
Figure 12B:
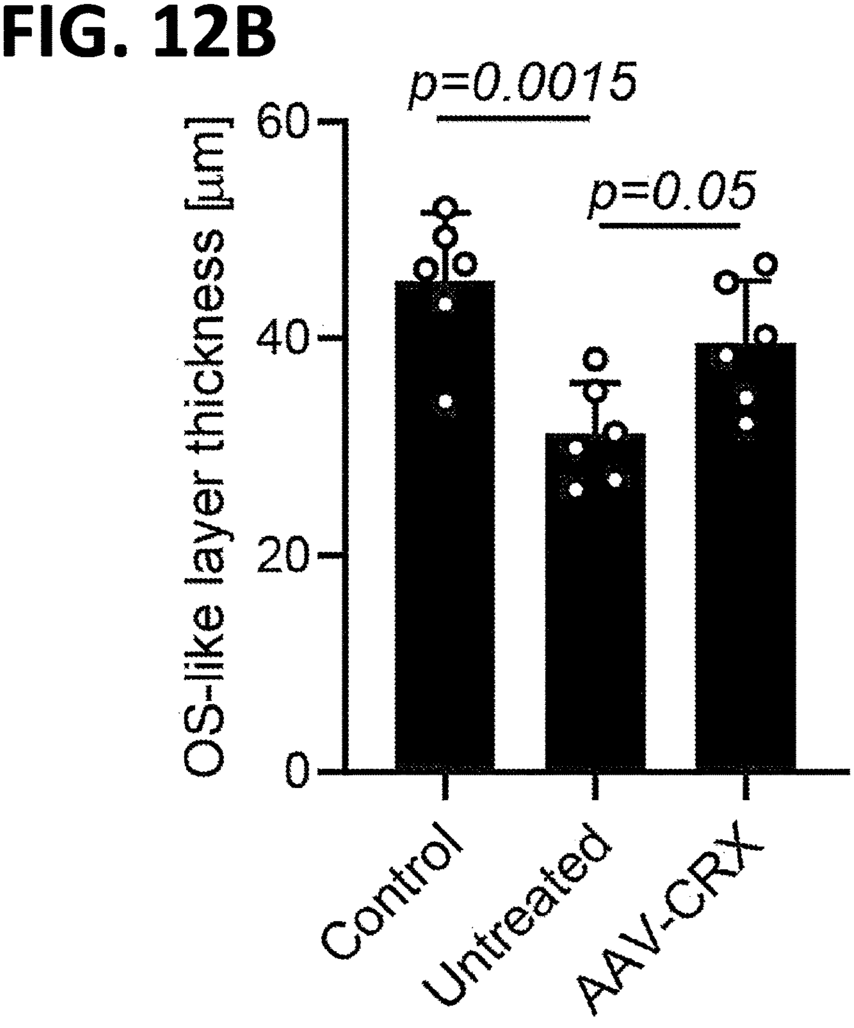
Figure 12C:
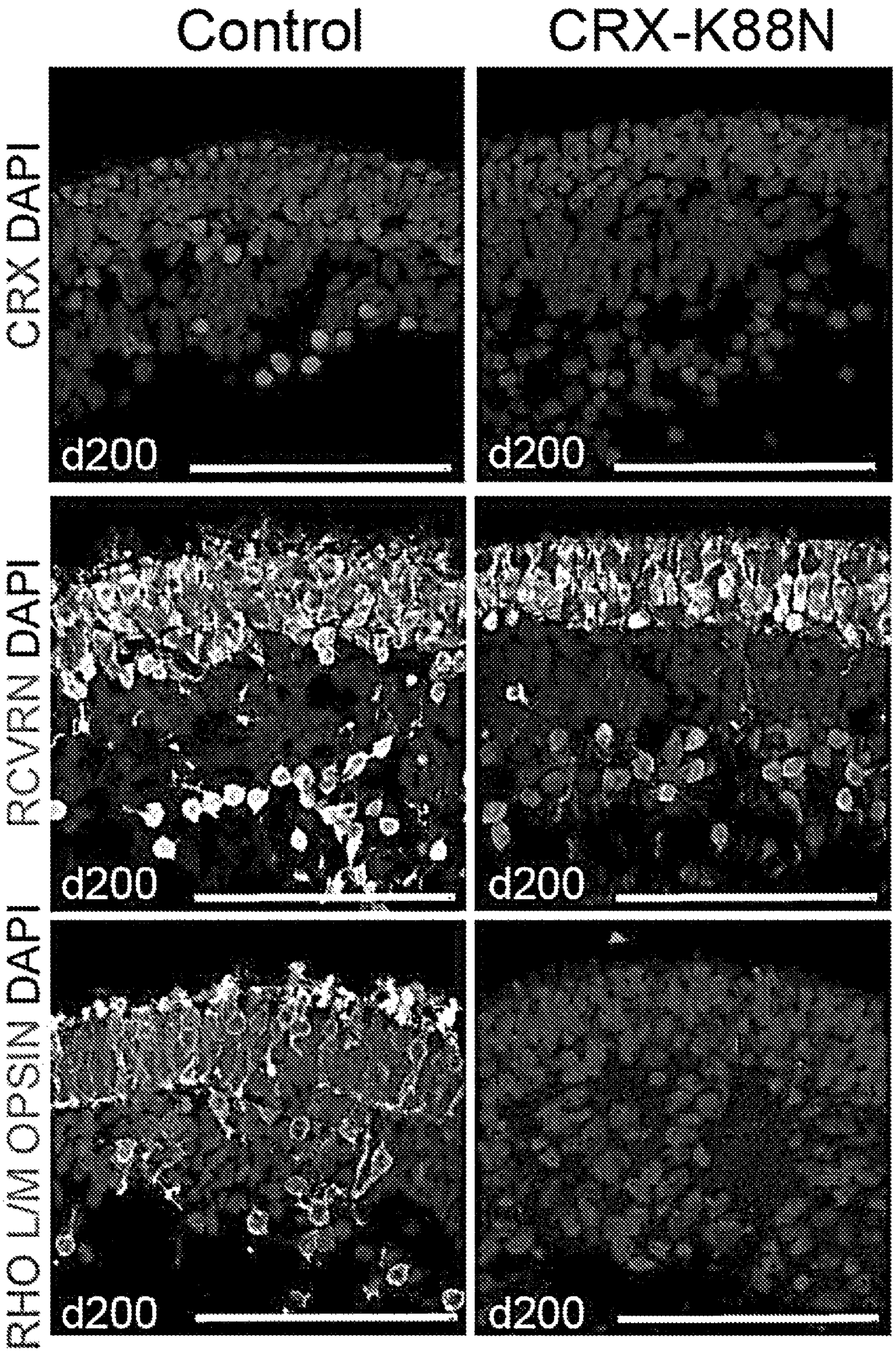
Figure 12D:
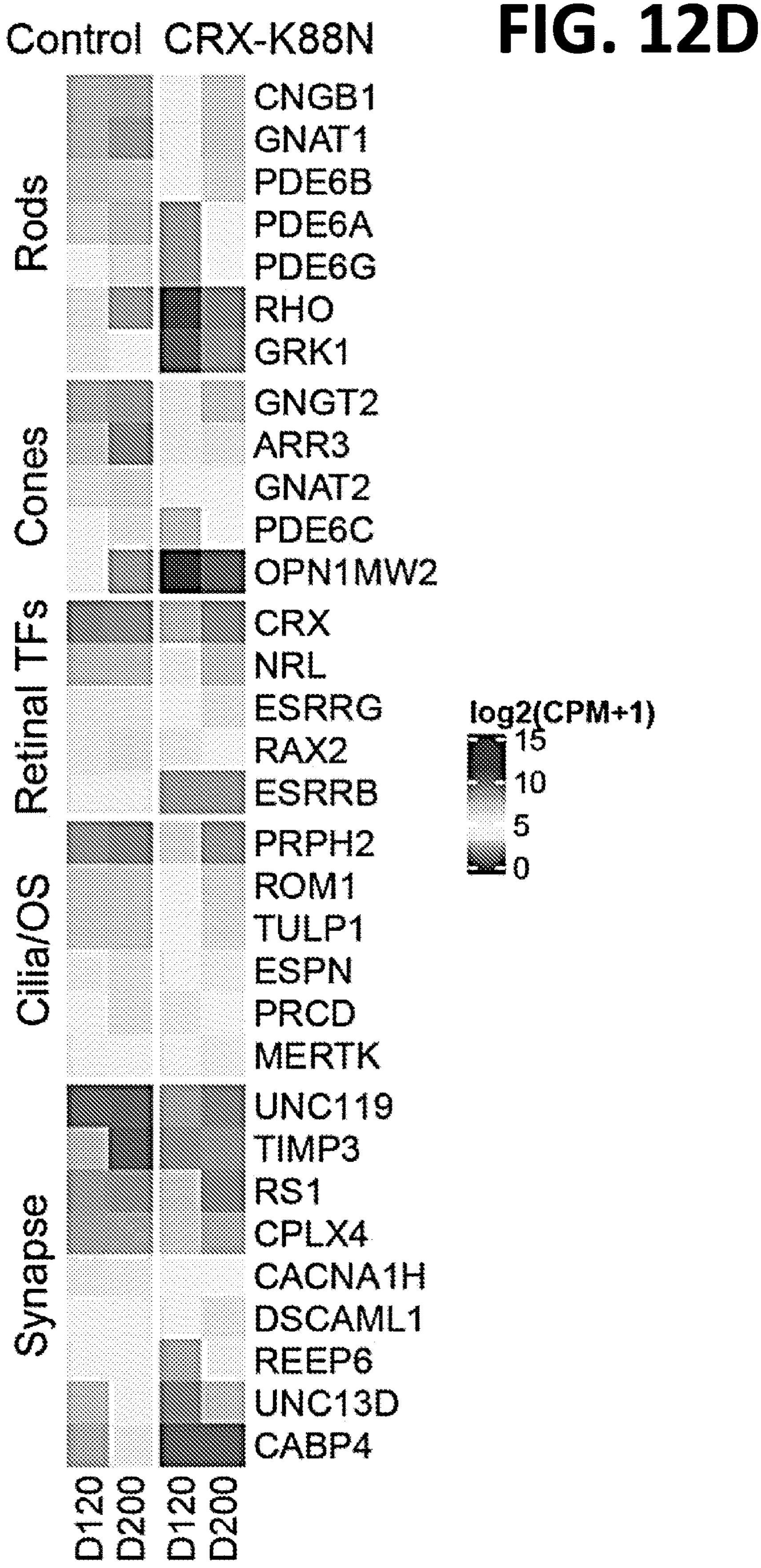
Figure 13A:
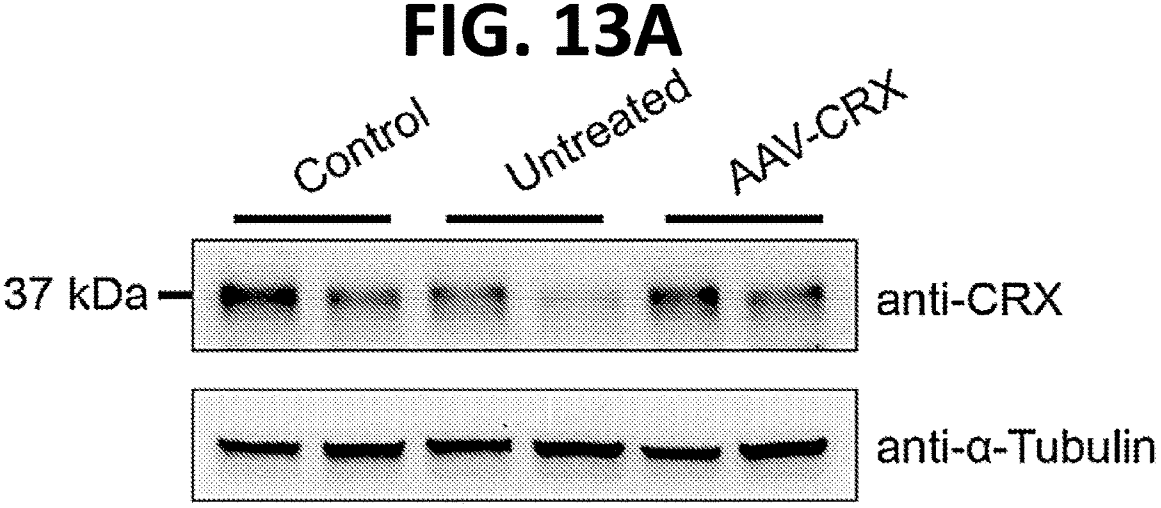
FIGS. 13A-13B. AAV treatment of CRX-K88N retinal organoids. (A) Immunoblot analysis of CRX protein in control, untreated and AAV-treated organoids at d200. α-tubulin was used as a loading control. Molecular mass of CRX is indicated on the left. (B) Immunostaining of retinal markers—S Opsin, SAG (rod visual arrestin) and synaptic proteins CTBP2 (Ribeye) and Bassoon (BSN)—in control, untreated and AAV-treated CRX-K88N organoids. Abnormally high S Opsin staining is reduced following AAV treatment; n=4 organoids examined in each group showed a consistent pattern. SAG expression which is undetectable in patient organoids is modestly rescued and synaptic areas show qualitatively more prominent staining after CRX augmentation.
Figure 13B:
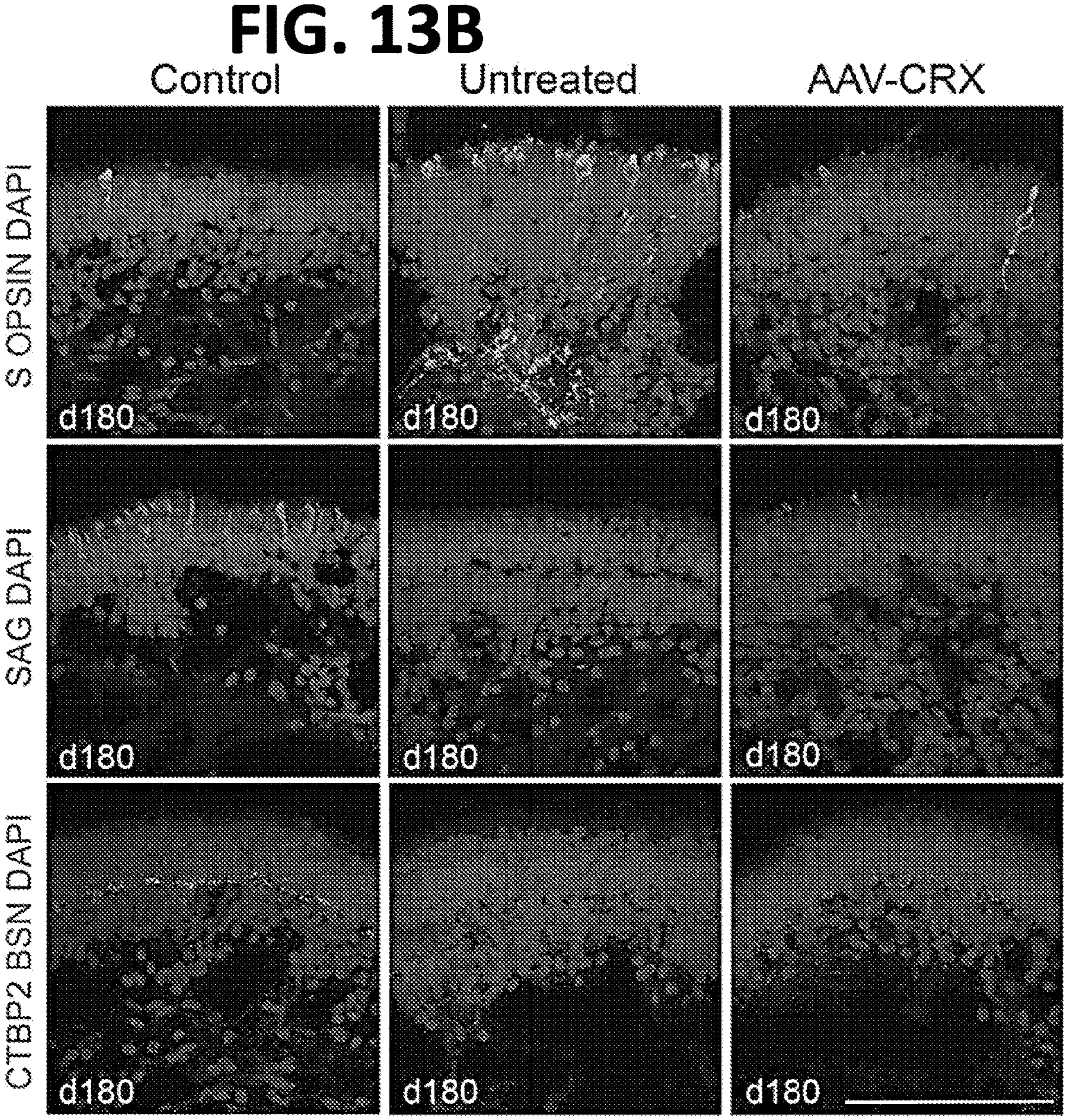

To determine whether the observed phenotypes and rescue were mutation-specific or could be generalized to other cases of dominant CRX-LCA, organoids were examined with the CRX K88N mutation. As for the frameshift mutation, no differences in morphology and expression of key retinal markers were evident at stage 1 or 2 of organoid differentiation (FIG. 11C-11E). However, outer segment-like structures were less developed at stage 3 in patient stem cell-derived organoids compared to the control (FIG. 12A, 12B). Immunostaining showed the presence of CRX and Recoverin, but severely diminished Rhodopsin and L/M Opsin staining in CRX-K88N organoids (FIG. 12C). Transcriptome analyses at d120 and d200 revealed delayed upregulation of many photoreceptor-specific genes (FIG. 12D) and confirmed the loss of Rhodopsin and L/M Opsin expression (RHO, OPN1MW2; FIG. 12D). Based on immunostaining, treatment of CRX-K88N organoids with AAV-CRX vector partially rescued Rhodopsin and L/M Opsin expression (FIG. 12E-12G), reduced abnormal S Opsin levels (FIG. 13B) and mediated modest induction of rod visual arrestin (SAG; FIG. 13B). Thus, CRX-K88N organoids showed a similar phenotype to CRX-I138fs, and AAV gene therapy was able to restore expression of CRX target genes.

Example 5

Animal Models

The disclosed methods of treatment can be tested in animal models of autosomal domain retinopathies. High conservation of CRX led to study of model organisms as a means of elucidating its roles in humans. In *Drosophila*, a single homologue otd functions similarly to OTX2 and CRX in development of fly photoreceptors. OTX2 as well as CRX expression can rescue specific defects in otd mutant flies suggesting overlapping yet distinct compensation of the fly gene product. Importantly, CRX mutants identified at NIH (Nichols et al., *Hum Mutat,* 31, E1472-1483) did not rescue the mutant phenotype (Terrell et al., *Dev Dyn,* 241, 215-228), instead showed strong detrimental effect on fly photoreceptor development demonstrating conserved antimorphic activity of this mutant CRX protein. Several mouse models and one cat model of CRX retinopathies have been developed and characterized. The first model was a deletion of Crx coding sequence in Crx knockout mice. These animals lack CRX expression completely and therefore model loss of CRX function in the retina. Histological analysis revealed loss of photoreceptor outer segment, specialized structures containing visual pigments and associated phototransduction proteins and impairment in development of photoreceptor synapses (Furukawa et al., *Cell,* 91, 531-541; Morrow et al., BMC Neurosci, 6, 5; Assawachananont et al., *Human molecular genetics,* 27, 3555-3567). Consistent with histological defects, photoreceptor electrical activity measured by electroretinogram is severely reduced. Furthermore, photoreceptors in the Crx knockout mice undergo degeneration leading to significant photoreceptor loss by adulthood (Furukawa et al., *Nature genetics,* 23, 466-470). Lack of photoreceptor function made this mouse model useful in examining potential therapeutic approaches aiming to restore lost photoreceptor activity. AAV5 vector-mediated expression of Crx driven by 2 kb mouse Crx promoter element improved histological abnormalities and partially restored light-evoked visual responses measured for cone photoreceptors (Watanabe et al., *PloS one,* 8, e54146). Transplantation of stem-cell derived developing photoreceptors was tested in this model with some positive results, although the extent of rescue was relatively small with this approach (Homma et al., *Stem Cells,* 31, 1149-1159; Lamba et al., *Cell Stem Cell,* 4, 73-79). While Crx knockout mice provide a model for loss of Crx function, mutations leading to complete loss of Crx coding sequence have not been reported to segregate with human disease. Thus, an important difference in human disease is the presence of one correct copy of CRX and a mutant allele, which is detrimental in photoreceptor development and function (Tran and Chen, *Dev Dyn,* 243, 1153-1166). Several mouse models were generated that harbor mutations showing phenotypes also in a heterozygous form, as observed in humans. R90W mutation in CRX has been found in an LCA patient in a homozygous form and ophthalmological assessment of other family members revealed mild abnormalities in a heterozygous form. Molecular analysis demonstrated reduced DNA binding and Rhodopsin promoter activation in cell lines (Swaroop et al., *Human molecular genetics,* 8, 299-305). A mouse model has been engineered to harbor the human mutation. These R90W knock-in mice represent a model for rare recessive LCA and mild cone dystrophy caused by CRX mutations. Consistent with human pathology heterozygous mice R90W/+ show mild cone function deficits, but the homozygous mutants R90W/R90W are completely blind from birth and show gross photoreceptor abnormalities (Tran et al., *PLOS Genet,* 10, e1004111). Mild phenotype in a heterozygous form suggests that indeed this is primarily a loss-of-function allele. Another mouse model of a mild retinopathy is the tvrm65 mouse strain containing L253× mutation in CRX, which truncates the protein removing OTX tail domain (Ruzycki et al., *Investigative ophthalmology & visual science,* 58, 4644-4653). In contrast to R90W/+, both rod and cone function are affected in L253X mice. However, the overall phenotype is also mild. Two mouse models are available for autosomal dominant CRX-LCA. E168d2 mouse knock-in contains a two base-pair deletion resulting in a truncation of CRX transactivation domain (Tran et al., *PLoS Genet,* 10, e1004111). Heterozygous E168d2 mice show functional impairments and show a significant reduction in numbers of cone photoreceptors at 1 month of age. Rod degeneration occurs later with majority of these cells lost by 6 months of age. Gene expression analysis revealed significant alterations in expression patterns of genes associated with phototransduction. Another model of severe autosomal dominant CRX-LCA is the $Crx^{Rip}$ mouse mutant (Roger et al., *J Clin Invest,* 124, 631-643). This mouse strain carries a frameshift deletion G255d1 leading to a 133 amino-acid non-homologous stretch of residues at the C terminus of the protein. $Crx^{Rip}$ protein does not bind to DNA and disrupts activation of Nrl expression by Otx2. As a consequence, there are major gene expression changes in $Crx^{Rip}$ mutant mice and their developmental phenotype is more severe than that of Crx knockout mice. Visual function is absent from birth as measured by electroretinogram in $Crx^{Rip}$ heterozygous mice, mimicking human autosomal dominant CRX-LCA clinical phenotype. Synapse development is also affected in $Crx^{Rip}$ mice highlighting deficits in signal transmission to second order neurons in the retina (Assawachananont et al., *Human molecular genetics,* 27, 3555-3567). Finally, a larger animal model of CRX retinopathy is also available in the form of Rdy cat (Occelli et al., *Investigative ophthalmology & visual science,* 57, 3780-3792). This spontaneous model carries a frameshift mutation A182d1 resulting in a truncated protein. Similar to the two autosomal dominant mouse models, impairment in retinal function measured by ERG is evident early and retinal degeneration occurs at later stages. Comparison of gene expression profiles in R90W, E168d2 and $Crx^{Rip}$ mouse strains suggested phenotype severity dependent on the extent of downregulation of key phototransduction-related genes in examined models (Ruzycki et al., *Genome Biology,* 16, 171). Downregulated genes were enriched for Crx binding sites and shown to undergo developmental regulation of epigenetic state during photoreceptor development. An interesting finding of the study is that differential dysregulation of a relatively small subset of genes could have a major phenotype-modifying effect. In conclusion, animal models of CRX retinopathies show a range of phenotypes consistent with the range observed in human disease and demonstrate divergent molecular mechanisms for individual mutations. The animal models can be used in further studies.

In view of the many possible embodiments to which the principles of our invention may be applied, it should be recognized that illustrated embodiments are only examples of the invention and should not be considered a limitation on the scope of the invention. Rather, the scope of the invention is defined by the following claims. We therefore claim as our invention all that comes within the scope and spirit of these claims.

We claim:

1. A method of treating a cone rod homeobox transcription factor (CRX) autosomal dominant retinopathy in a subject, comprising administering to the eye of the subject a nucleic acid molecule comprising a retinal specific promoter operably linked to a nucleic acid molecule encoding a CRX protein, wherein the human CRX promoter comprises SEQ ID NO: 1, thereby treating the CRX autosomal dominant retinopathy in the subject.

2. The method of claim 1, wherein the CRX autosomal dominant retinopathy is Leber congenital amaurosis (LCA), retinitis pigmentosa, or cone rod dystrophy.

3. The method of claim 2, wherein the CRX autosomal dominant retinopathy is the LCA.

4. The method of claim 1, comprising administering to the subject a viral vector comprising the retinal specific promoter operably linked to the nucleic acid molecule encoding the CRX protein.

5. The method of claim 4, wherein the viral vector is a lentivirus vector or an adeno-associated virus (AAV) vector.

6. The method of claim 5, wherein the viral vector is the AAV vector, and wherein the AAV vector is an AAV2, AAV5, or AAV8 virus vector.

7. The method of claim 1, comprising administering to the subject a nanoparticle or a dendrimer comprising the nucleic acid molecule.

8. The method of claim 1, wherein the CRX protein comprises an amino acid sequence at least 95% identical to SEQ ID NO: 2.

9. The method of claim 8, wherein the CRX protein comprises the amino acid sequence of SEQ ID NO: 2.

10. The method of claim 1, wherein the nucleic acid molecule is administered intra-vitreally, sub-retinally, or to the retina of the subject.

11. The method of claim 1, wherein the subject is a human.

* * * * *